US009394315B2

(12) United States Patent
Aicher et al.

(10) Patent No.: US 9,394,315 B2
(45) Date of Patent: Jul. 19, 2016

(54) TETRAHYDRO[1,8]NAPHTHYRIDINE SULFONAMIDE AND RELATED COMPOUNDS FOR USE AS AGONISTS OF RORγ AND THE TREATMENT OF DISEASE

(71) Applicant: Lycera Corporation, Ann Arbor, MI (US)

(72) Inventors: Thomas D. Aicher, Ann Arbor, MI (US); Peter L. Toogood, Ann Arbor, MI (US); Xiao Hu, Northville, MI (US)

(73) Assignee: Lycera Corporation, Ann Arbor, MI (US)

( * ) Notice: Subject to any disclaimer, the term of this patent is extended or adjusted under 35 U.S.C. 154(b) by 0 days.

(21) Appl. No.: 14/398,774

(22) PCT Filed: May 8, 2013

(86) PCT No.: PCT/US2013/040085
§ 371 (c)(1),
(2) Date: Nov. 4, 2014

(87) PCT Pub. No.: WO2013/169864
PCT Pub. Date: Nov. 14, 2013

(65) Prior Publication Data
US 2015/0133437 A1 May 14, 2015

Related U.S. Application Data

(60) Provisional application No. 61/644,104, filed on May 8, 2012.

(51) Int. Cl.
C07D 498/04 (2006.01)
C07D 471/04 (2006.01)
C07D 491/052 (2006.01)

(52) U.S. Cl.
CPC ............ *C07D 498/04* (2013.01); *C07D 471/04* (2013.01); *C07D 491/052* (2013.01)

(58) Field of Classification Search
CPC ............................ C07D 498/04; C07D 471/04
USPC ........................................ 544/105; 514/230.5
See application file for complete search history.

(56) References Cited

U.S. PATENT DOCUMENTS

| | | | |
|---|---|---|---|
| 5,985,903 A | 11/1999 | Assmann et al. |
| 6,020,354 A | 2/2000 | Assmann et al. |
| 6,037,367 A | 3/2000 | Christensen, IV et al. |
| 6,160,001 A | 12/2000 | Assmann et al. |
| 6,172,092 B1 | 1/2001 | Assmann et al. |
| 6,180,643 B1 | 1/2001 | Zablocki et al. |
| 6,348,032 B1 | 2/2002 | Sperl et al. |
| 6,352,985 B1 | 3/2002 | Yamasaki et al. |
| 6,387,939 B1 | 5/2002 | Assmann et al. |
| 6,440,973 B1 | 8/2002 | Zablocki et al. |
| 6,534,535 B1 | 3/2003 | Zhu et al. |
| 6,605,634 B2 | 8/2003 | Zablocki et al. |
| 6,638,960 B2 | 10/2003 | Assmann et al. |
| 6,683,091 B2 | 1/2004 | Asberom et al. |
| 6,828,344 B1 | 12/2004 | Seehra et al. |
| 7,084,176 B2 | 8/2006 | Morie et al. |
| 7,138,401 B2 | 11/2006 | Kasibhatla et al. |
| 7,329,675 B2 | 2/2008 | Cox et al. |
| 7,420,059 B2 | 9/2008 | O'Connor et al. |
| 7,482,342 B2 | 1/2009 | D'Orchymont et al. |
| 7,569,571 B2 | 8/2009 | Dong et al. |
| 7,696,200 B2 | 4/2010 | Ackermann et al. |
| 7,713,996 B2 | 5/2010 | Ackermann et al. |
| 7,741,495 B2 | 6/2010 | Liou et al. |
| 7,799,933 B2 | 9/2010 | Ceccarelli et al. |
| 2006/0004000 A1 | 1/2006 | D'Orchymont et al. |
| 2006/0100230 A1 | 5/2006 | Bischoff et al. |
| 2007/0010537 A1 | 1/2007 | Hamamura et al. |
| 2007/0010670 A1 | 1/2007 | Hirata et al. |
| 2007/0049556 A1 | 3/2007 | Zhang et al. |
| 2007/0060567 A1 | 3/2007 | Ackermann et al. |
| 2007/0154487 A1 | 7/2007 | Littman et al. |
| 2007/0191603 A1 | 8/2007 | Ackermann et al. |
| 2007/0281922 A1 | 12/2007 | Liu et al. |
| 2008/0027100 A1 | 1/2008 | McCormick et al. |
| 2008/0058386 A1 | 3/2008 | Liou et al. |
| 2008/0153805 A1 | 6/2008 | Ceccarelli et al. |
| 2009/0075973 A1 | 3/2009 | Newcom et al. |
| 2009/0247502 A1 | 10/2009 | Newcom et al. |
| 2009/0275586 A1 | 11/2009 | Govek et al. |
| 2010/0022515 A1 | 1/2010 | Alper et al. |
| 2010/0130484 A1 | 5/2010 | Ackermann et al. |
| 2010/0234340 A1 | 9/2010 | Schunk et al. |
| 2011/0053915 A1 | 3/2011 | Ivaschenko et al. |
| 2011/0112070 A1 | 5/2011 | Baldwin et al. |
| 2011/0118246 A1 | 5/2011 | Baldwin et al. |
| 2011/0178063 A1 | 7/2011 | Baldwin et al. |
| 2014/0088094 A1 | 3/2014 | Glick et al. |

FOREIGN PATENT DOCUMENTS

EP 0882718 A1 12/1998
EP 1820515 A1 8/2007

(Continued)

OTHER PUBLICATIONS

Boger et al., "Regiocontrolled Nucleophilic Addition to Selectively Activated p-Quinone Diimines: Alternative Preparation of a Key Intermediate Employed in the Preparation of the CC-1065 Left-Hand Subunit," J. Org. Chem., vol. 55, pp. 1379-1390 (1990).
Chang et al., "7-Aroyl-aminoindoline-1-sulfonamides as a Novel Class of Potent Antitubulin Agents," J. Med. Chem., vol. 49, pp. 6656-6659 (2006).
English Abstract JP6-250441 published 1994 (1 page).
English Abstract of JP2004307487A published 2004 (2 pages).
Guimond et al., "Rhodium(III)-Catalyzed Isoquinolone Synthesis: The N—O Bond as a Handle for C—N Bond Formation and Catalyst Turnover," J. Am. Chem. Soc., vol. 132, pp. 6908-6909 (2010).

(Continued)

*Primary Examiner* — Kahsay Habte
(74) *Attorney, Agent, or Firm* — Goodwin Procter LLP

(57) ABSTRACT

The invention provides tetrahydro[1,8]naphthyridine and related compounds, pharmaceutical compositions, methods of promoting RORγ activity, increasing the amount of IL-17 in a subject, and treating cancer, bacterial infections, and fungal infections using such tetrahydro[1,8]naphthyridine and related compounds.

30 Claims, No Drawings

(56) References Cited

FOREIGN PATENT DOCUMENTS

| | | |
|---|---|---|
| EP | 2181710 A1 | 5/2010 |
| JP | 6-250441 A | 9/1994 |
| JP | 2004307487 A | 11/2004 |
| WO | WO-92/13856 A1 | 8/1992 |
| WO | WO-97/01561 A1 | 1/1997 |
| WO | WO-97/48697 A1 | 12/1997 |
| WO | WO-98/22457 A1 | 5/1998 |
| WO | WO-00/17202 A1 | 3/2000 |
| WO | WO-01/12600 A9 | 9/2002 |
| WO | WO-02/100819 A1 | 12/2002 |
| WO | WO-03/014075 A2 | 2/2003 |
| WO | WO-2004/056830 A1 | 7/2004 |
| WO | WO-2005/028434 A2 | 3/2005 |
| WO | WO-2005/037834 A1 | 4/2005 |
| WO | WO-2006/007486 A2 | 1/2006 |
| WO | WO-2006/057460 A1 | 6/2006 |
| WO | WO-2007/031429 A1 | 3/2007 |
| WO | WO-2007/093507 A1 | 8/2007 |
| WO | WO-2007/125405 A2 | 11/2007 |
| WO | WO-2008/003703 A1 | 1/2008 |
| WO | WO-2008/045664 A2 | 4/2008 |
| WO | WO-2008/062740 A1 | 5/2008 |
| WO | WO-2008/074692 A1 | 6/2008 |
| WO | WO-2008/097428 A2 | 8/2008 |
| WO | WO-2009/032667 A1 | 3/2009 |
| WO | WO-2009/035997 A2 | 3/2009 |
| WO | WO-2009/077956 A2 | 6/2009 |
| WO | WO-2009/147187 A1 | 12/2009 |
| WO | WO-2009/157196 A1 | 12/2009 |
| WO | WO-2010/017827 A1 | 2/2010 |
| WO | WO-2010/038901 A1 | 4/2010 |
| WO | WO-2010/057101 A2 | 5/2010 |
| WO | WO-2010/059602 A2 | 5/2010 |
| WO | WO-2010/102958 A1 | 9/2010 |
| WO | WO-2010/117425 A1 | 10/2010 |
| WO | WO-2010/125082 A1 | 11/2010 |
| WO | WO-2011/019634 A2 | 2/2011 |
| WO | WO-2011/067364 A1 | 6/2011 |
| WO | WO-2011/067365 A1 | 6/2011 |
| WO | WO-2011/067366 A1 | 6/2011 |
| WO | WO-2011/109059 A1 | 9/2011 |
| WO | WO-2012/032065 A1 | 3/2012 |
| WO | WO-2012/032067 A1 | 3/2012 |
| WO | WO-2012/037108 A1 | 3/2012 |
| WO | WO-2012/064744 A2 | 5/2012 |
| WO | WO-2013/169588 A1 | 11/2013 |
| WO | WO-2013/169704 A2 | 11/2013 |

OTHER PUBLICATIONS

International Search Report and Written Opinion for PCT/US2011/059788 dated May 23, 2012 (23 pages).

International Search Report and Written Opinion for PCT/US2013/040085 dated Oct. 23, 2013 (9 pages).

International Search Report for PCT/US2013/039422 dated Oct. 11, 2013 (4 pages).

International Search Report for PCT/US2013/039839 dated Oct. 18, 2013 (3 pages).

Ishikura et al., "An Efficient Synthesis of 3-Heteroarylpyridines via Diethyl-(3-pyridyl)-borane," Synthesis, pp. 936-938 (1984).

Jiang et al., "Synthesis and Cytotoxicity Evaluation of Novel Indolylpyrimidines and Indolylpyrazines as Potential Antitumor Agents," Bioorg. Med. Chem., vol. 9, pp. 1149-1154 (2001).

Li et al., "Chemical Libraries via Sequential C—H Functionalization of Phenols," J. Comb. Chem., vol. 10, pp. 170-174 (2008).

Liu et al., "1-Sulfonylindazoles as potent and selective 5-$HT_6$ ligands," Bioorg. Med. Chem. Lett., vol. 19, pp. 2413-2415 (2009).

Murase et al., "A New Concise Synthesis of Arcyriacyanin A and Its Unique Inhibitory Activity against a Panel of Human Cancer Cell Line," Chem. Pharm. Bull., vol. 48, pp. 81-84 (2000).

STN Columbus, pp. 1-40, (2011).

Wang et al., "Synthesis of new carbon-11-labeled 7-aroyl-aminoindoline-1-sulfonamides as potential PET agents for imaging of tubulin polymerization in cancers," J. Label Compd. Radiopharm, vol. 51, pp. 6-11 (2008).

Yeh et al., "Practical Cu-catalyzed amination of functionalized heteroaryl halides," Tetrahedron Letters 47, pp. 6011-6016 (2006).

TETRAHYDRO[1,8]NAPHTHYRIDINE SULFONAMIDE AND RELATED COMPOUNDS FOR USE AS AGONISTS OF RORγ AND THE TREATMENT OF DISEASE

CROSS REFERENCE TO RELATED APPLICATIONS

This application is a national stage of International (PCT) Patent Application Serial No. PCT/US2013/040085, filed May 8, 2013, and published under PCT Article 21(2) in English, which claims the benefit of and priority to U.S. Provisional Patent Application Ser. No. 61/644,104, filed May 8, 2012, the contents of each of which are hereby incorporated by reference.

FIELD OF THE INVENTION

The invention provides tetrahydro[1,8]naphthyridine and related compounds, methods of promoting RORγ activity and/or increasing the amount of IL-17 in a subject, and therapeutic uses of the tetrahydro[1,8]naphthyridine and related compounds. In particular, the invention provides sulfonamide-tetrahydro[1,8]naphthyridine and related compounds, methods of using such compounds to promote RORγ activity and/or increase the amount of IL-17 in a subject, and treat medical conditions in which activation of immune response would be beneficial such as in cancer and infections.

BACKGROUND OF THE INVENTION

Retinoid-related orphan receptors (ROR) are reported to have an important role in numerous biological processes. See, for example, Dussault et al. in *Mech. Dev.* (1998) vol. 70, 147-153; and Andre et al. in *EMBO J.* (1998) vol. 17, 3867-3877. Scientific investigations relating to each of retinoid-related orphan receptors RORα, RORβ, and RORγ have been described in the literature. See, for example, Hirose et al. in *Biochem. Biophys. Res. Commun.* (1994) vol. 205, 1976-1983; Giguere et al. in *Genes. Dev.* (1994) vol. 8, 538-553; Medvedev et al. in *Gene* (1996) vol. 181, 199-206; Ortiz et al. in *Mol. Endocrinol.* (1995) vol. 9, 1679-1691; Jetten A M in *Curr Drug Targets Inflamm Allergy* (2004) vol. 3, 395-412). Continuing research in this field is spurred by the promise of developing new therapeutic agents to treat medical disorders associated with retinoid-related orphan receptor activity.

RORγ has been reported to be expressed in high concentration in various tissues, such as thymus, kidney, liver, muscle, and certain fat tissue. See, for example, Hirose et al. in *Biochem. Biophys. Res. Commun.* (1994) vol. 205, 1976-1983; Medvedev et al. in *Gene* (1996) vol. 181, 199-206; Ortiz et al. in *Mol. Endocrinol.* (1995) vol. 9, 1679-1691; and He et al. in *Immunity* (1998) vol. 9, 797-806. Two isoforms of RORγ have been identified and are referred to as γ1 and γ2 (also referred to as RORγt). See, for example, He et al. in *Immunity* (1998) vol. 9, 797-806. Expression of the γ2 isoform has been reported to appear in, for example, double-positive thymocytes. See, for example, He et al. in *Immunity* (1998) vol. 9, 797-806; and Villey et al. in *Eur. J. Immunol.* (1999) vol. 29, 4072-4080. RORγt plays a critical role in regulating differentiation of Th17 cells, a subset of T helper lymphocytes. See, for example, Ivanov et al. in Cell (2006) vol. 126, 1121-1133. Th17 cells are important for recruiting tumor-killing cytotoxic CD8+ T cells and natural killer cells into the tumor microenvironment. The level of Th17 cells correlated positively with patient survival or slower disease progression in certain cancers. See, for example, Kryczek et al. in *Blood* (2009) vol 114, 1141-1149; and Sfanos et al. in *Clinical Cancer Research* (2008) vol 14, 3254-3261. Compounds capable of enhancing RORγt activity are thus contemplated to provide a therapeutic benefit in the treatment of cancer.

Cancer continues to be a significant health problem despite the substantial research efforts and scientific advances reported in the literature for treating this disease. Some of the most frequently diagnosed cancers include prostate cancer, breast cancer, and lung cancer. Prostate cancer is the most common form of cancer in men. Breast cancer remains a leading cause of death in women. Current treatment options for these cancers are not effective for all patients and/or can have substantial adverse side effects.

Accordingly, a need exists for improved treatments for cancer. The present invention addresses this need and provides other related advantages.

SUMMARY

The invention provides 1,8-tetrahydro[1,8]naphthyridine and related compounds, pharmaceutical compositions, methods of promoting RORγ activity and/or increasing the amount of IL-17 in a subject, and methods of treating various medical disorders using such compounds. In particular, one aspect of the invention provides a collection of tetrahydro[1,8]naphthyridine and related compounds, such as a compound represented by Formula I:

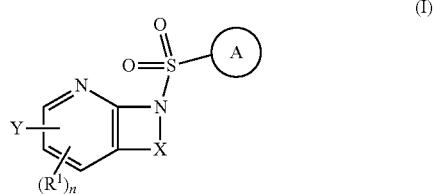

or a pharmaceutically acceptable salt or solvate thereof; wherein the variables are as defined in the detailed description. Further description of additional collections of tetrahydro[1,8]naphthyridine and related compounds, such as Formulae II-V, are described in the detailed description.

Another aspect of the invention provides a method of treating a subject suffering from a medical disorder. The method comprises administering to the subject a therapeutically effective amount of one or more tetrahydro[1,8]naphthyridine or related compounds described herein, e.g., a compound of Formula I, II, III, IV, or V, wherein Formulae I-V are as described in the detailed description. A large number of disorders can be treated using the tetrahydro[1,8]naphthyridine and related compounds described herein. For example, the compounds described herein can be used to treat cancer, a bacterial infection, a fungal infection, or an immune deficiency disorder.

Another aspect of the invention provides a method of promoting the activity of RORγ. The method comprises exposing a RORγ to an effective amount of one or more tetrahydro[1, 8]naphthyridine or related compounds described herein, e.g., a compound of Formula I, II, III, IV, or V, or a pharmaceutical composition described herein.

Another aspect of the invention provides a method of increasing the amount of IL-17 in a subject. The method comprises administering to a subject an effective amount of one or more tetrahydro[1,8]naphthyridine or related compounds described herein, e.g., a compound of Formula I, II, III, IV, or V, or a pharmaceutical composition described herein, to increase the amount of IL-17 in the subject.

DETAILED DESCRIPTION OF THE INVENTION

The invention provides tetrahydro[1,8]naphthyridine and related compounds, pharmaceutical compositions, methods of promoting RORγ activity and/or increasing the amount of IL-17 in a subject, and therapeutic uses of the tetrahydro[1,8]naphthyridine and related compounds. The practice of the present invention employs, unless otherwise indicated, conventional techniques of organic chemistry, pharmacology, molecular biology (including recombinant techniques), cell biology, biochemistry, and immunology. Such techniques are explained in the literature, such as in "Comprehensive Organic Synthesis" (B. M. Trost & I. Fleming, eds., 1991-1992); "Handbook of experimental immunology" (D. M. Weir & C. C. Blackwell, eds.); "Current protocols in molecular biology" (F. M. Ausubel et al., eds., 1987, and periodic updates); and "Current protocols in immunology" (J. E. Coligan et al., eds., 1991), each of which is herein incorporated by reference in its entirety.

Various aspects of the invention are set forth below in sections; however, aspects of the invention described in one particular section are not to be limited to any particular section. Further, when a variable is not accompanied by a definition, the previous definition of the variable controls.

Definitions

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "fluoroalkyl," "—O-alkyl," etc.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and include bicycloalkyls such as where two saturated carbocyclic rings are fused together. In certain embodiments, the cycloalkyls have about 5, 6 or 7 carbons in the ring structure. Exemplary alkyl groups include methyl, ethyl, n-propyl, isopropyl, n-butyl, sec-butyl, isobutyl, tert-butyl, cyclopropyl, and cyclobutyl.

The term "alkylene" refers to a diradical of an alkyl group. Exemplary alkylene groups include —$CH_2CH_2$—,

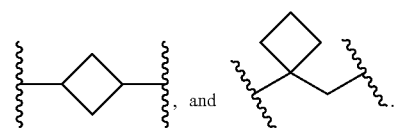

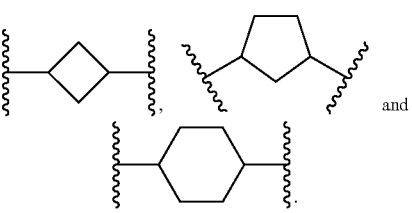

The term "cycloalkylene" refers to a diradical of a cycloalkyl group. Exemplary cycloalkylene groups include The term "haloalkyl" refers to an alkyl group that is substituted with at least one halogen. Exemplary haloalkyl groups include —$CH_2F$, —$CHF_2$, —$CF_3$, —$CH_2CF_3$, —$CF_2CF_3$, and the like.

The term "hydroxyalkyl" refers to an alkyl group that is substituted with at least one hydroxyl group. Exemplary hydroxyl alkyl groups include —$CH_2OH$, —$CH_2CH_2OH$, —$C(H)(OH)C(OH)H_2$, and the like.

The term "aralkyl" refers to an alkyl group substituted with an aryl group. Exemplary aralkyl groups include

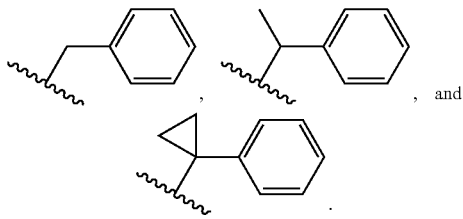

The term "heteroaralkyl" refers to an alkyl group substituted with a heteroaryl group.

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to a carbocyclic aromatic group. Representative aryl groups include phenyl, naphthyl, anthracenyl, and the like. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —$CO_2$alkyl, carbonyl, carboxyl, alkylthio, sulfonyl, sulfonamido, sulfonamide, ketone, aldehyde, ester, heterocyclyl, aryl or heteroaryl moieties, —$CF_3$, —CN, or the like. The term "aryl" also includes polycyclic aromatic ring systems having two or more carbocyclic rings in which two or more carbons are common to two adjoining rings (the rings are "fused rings") wherein all of the fused rings are aromatic rings, e.g., in a naphthyl group.

The term "heteroaryl" is art-recognized and refers to aromatic groups that include at least one ring heteroatom. In certain instances, a heteroaryl group contains 1, 2, 3, or 4 ring heteroatoms. Representative examples of heteroaryl groups include pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. Unless specified otherwise, the heteroaryl ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. The term "heteroaryl" also includes polycyclic aromatic ring systems having two or more rings in which two or more carbons are common to two adjoining rings (the rings are "fused rings") wherein all of the fused rings are heteroaromatic, e.g., in a naphthyridinyl group.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

As used herein, the terms "heterocyclic" and "heterocyclyl" represent, for example, an aromatic or nonaromatic ring (e.g., a monocyclic or bicyclic ring) containing one or more heteroatoms. The heteroatoms can be the same or different from each other. Examples of heteroatoms include, but are not limited to nitrogen, oxygen and sulfur. Aromatic and nonaromatic heterocyclic rings are well-known in the art. Some nonlimiting examples of aromatic heterocyclic rings include, but are not limited to, pyridine, pyrimidine, indole, purine, quinoline and isoquinoline. Nonlimiting examples of nonaromatic heterocyclic compounds include, but are not limited to, piperidine, piperazine, morpholine, pyrrolidine and pyrazolidine. Examples of oxygen containing heterocyclic rings include, but are not limited to, furan, oxirane, 2H-pyran, 4H-pyran, 2H-chromene, benzofuran, and 2,3-dihydrobenzo[b][1,4]dioxine. Examples of sulfur-containing heterocyclic rings include, but are not limited to, thiophene, benzothiophene, and parathiazine. Examples of nitrogen containing rings include, but are not limited to, pyrrole, pyrrolidine, pyrazole, pyrazolidine, imidazole, imidazoline, imidazolidine, pyridine, piperidine, pyrazine, piperazine, pyrimidine, indole, purine, benzimidazole, quinoline, isoquinoline, triazole, and triazine. Examples of heterocyclic rings containing two different heteroatoms include, but are not limited to, phenothiazine, morpholine, parathiazine, oxazine, oxazole, thiazine, and thiazole. The heterocyclic ring is optionally further substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the heterocyclyl group is a 3-7 membered ring that, unless specified otherwise, is substituted or unsubstituted.

The term "heterocycloalkyl" refers to a saturated heterocyclyl group having, for example, 3-7 ring atoms.

The terms "amine" and "amino" are art-recognized and refer to both unsubstituted and substituted amines, e.g., a moiety that may be represented by the general formulas:

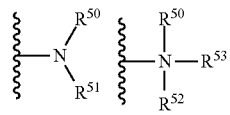

wherein $R^{50}$, $R^{51}$, $R^{52}$ and $R^{53}$ each independently represent a hydrogen, an alkyl, an alkenyl, —(CH$_2$)$_m$—R$^{61}$, or $R^{50}$ and $R^{51}$, taken together with the N atom to which they are attached complete a heterocycle having from 4 to 8 atoms in the ring structure; $R^{61}$ represents an aryl, a cycloalkyl, a cycloalkenyl, a heterocycle or a polycycle; and m is zero or an integer in the range of 1 to 8. In certain embodiments, only one of $R^{50}$ or $R^{51}$ may be a carbonyl, e.g., $R^{50}$, $R^{51}$ and the nitrogen together do not form an imide. In other embodiments, $R^{50}$ and $R^{51}$ (and optionally $R^{52}$) each independently represent a hydrogen, an alkyl, an alkenyl, or —(CH$_2$)$_m$—R$^{61}$.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and —O—(CH$_2$)$_m$—R$^{61}$, where m and $R^{61}$ are described above.

The term "oxo" is art-recognized and refers to a "=O" substituent. For example, a cyclopentane substituted with an oxo group is cyclopentanone.

The symbol "⌇" indicates a point of attachment.

The term "substituted" means that one or more hydrogens on the atoms of the designated group are replaced with a selection from the indicated group, provided that the atoms' normal valencies under the existing circumstances are not exceeded, and that the substitution results in a stable compound. Combinations of substituents and/or variables are permissible only if such combinations result in stable compounds. The terms "stable compound" or "stable structure" refer to a compound that is sufficiently robust to survive isolation to a useful degree of purity from a reaction mixture, and formulation into an efficacious therapeutic agent.

When any substituent or variable occurs more than one time in any constituent or the compound of the invention, its definition on each occurrence is independent of its definition at every other occurrence, unless otherwise indicated.

It should also be noted that any carbon as well as heteroatom with unsatisfied valences in the text, schemes, examples and tables herein is assumed to have the sufficient number of hydrogen atom(s) to satisfy the valences.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is H$_2$O.

Certain compounds contained in compositions of the present invention may exist in particular geometric or stereoisomeric forms. Further, certain compounds described herein may be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. The compounds may contain one or more stereogenic centers. For example, asymmetric carbon atoms may be present in a substituent such as an alkyl group. All such isomers, as well as mixtures thereof, are intended to be included in this invention, such as, for example, racemic mixtures, single enantiomers, diastereomeric mixtures and individual diastereomers. Additional asymmetric centers may be present depending upon the nature of the various substituents on the molecule. Each such asymmetric center will independently produce two optical isomers, and it is intended that all of the possible optical isomers, diastereomers in mixtures, and pure or partially purified compounds are included within the ambit of this invention.

Diastereomeric mixtures can be separated into their individual diastereomers on the basis of their physical chemical differences by methods known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Alternatively, a particular enantiomer of a compound of the present invention may be prepared by asymmetric synthesis. Still further, where the molecule contains a basic functional group (such as amino) or an acidic functional group (such as carboxylic acid) diastereomeric salts are formed with an appropriate optically-active acid or base, followed by resolution of the diastereomers thus formed by fractional crystallization or chromatographic means known in the art, and subsequent recovery of the pure enantiomers.

Individual stereoisomers of the compounds of the invention may, for example, be substantially free of other isomers, or may be admixed, for example, as racemates or with all other, or other selected, stereoisomers. Chiral center(s) in a compound of the present invention can have the S or R configuration as defined by the IUPAC 1974 Recommendations. Further, to the extent a compound described herein may exist as a atropisomer (e.g., substituted biaryls), all forms of such atropisomer are considered part of this invention.

As used herein, the terms "subject" and "patient" are used interchangeable and refer to organisms to be treated by the methods of the present invention. Such organisms preferably include, but are not limited to, mammals (e.g., murines, simians, equines, bovines, porcines, canines, felines, and the like), and most preferably includes humans.

The term "$IC_{50}$" is art-recognized and refers to the concentration of a compound that is required for 50% inhibition of its target.

As used herein, the term "effective amount" refers to the amount of a compound sufficient to effect beneficial or desired results (e.g., a therapeutic, ameliorative, inhibitory or preventative result). An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate (also known as toluenesulfonate), undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. Further examples of salts include, but are not limited to: ascorbate, borate, nitrate, phosphate, salicylate, and sulfate. Further, acids which are generally considered suitable for the formation of pharmaceutically useful salts from basic pharmaceutical compounds are discussed, for example, by P. Stahl et al., Camille G. (eds.) *Handbook of Pharmaceutical Salts. Properties, Selection and Use*. (2002) Zurich: Wiley-VCH; S. Berge et al., *Journal of Pharmaceutical Sciences* (1977) 66(1) 1-19; P. Gould, *International J. of Pharmaceutics* (1986) 33 201-217; Anderson et al., *The Practice of Medicinal Chemistry* (1996), Academic Press, New York; and in *The Orange Book* (Food & Drug Administration, Washington, D.C. on their website). These disclosures are incorporated herein by reference.

Additional exemplary basic salts include, but are not limited to ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

In addition, when a compound of the invention contains both a basic moiety (such as, but not limited to, a pyridine or imidazole) and an acidic moiety (such as, but not limited to, a carboxylic acid) zwitterions ("inner salts") may be formed. Such acidic and basic salts used within the scope of the invention are pharmaceutically acceptable (i.e., non-toxic, physiologically acceptable) salts. Such salts of the compounds of the invention may be formed, for example, by reacting a compound of the invention with an amount of acid or base, such as an equivalent amount, in a medium such as one in which the salt precipitates or in an aqueous medium followed by lyophilization.

The present invention includes the compounds of the invention in all their isolated forms (such as any solvates, hydrates, stereoisomers, and tautomers thereof). Further, the invention includes compounds in which one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques known to those skilled in the art or by processes analogous to those described in the Schemes and Examples herein using appropriate isotopically-enriched reagents and/or intermediates.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

The terms "a" and "an" as used herein mean "one or more" and include the plural unless the context is inappropriate.

The abbreviation "THF" is art-recognized and refers to tetrahydrofuran. The abbreviation "DCM" is art-recognized and refers to dichloromethane. The abbreviation "DMF" is art-recognized and refers to dimethylformamide. The abbreviation "DMA" is art-recognized and refers to dimethylacetamide. The abbreviation "EDTA" is art-recognized and refers to ethylenediaminetetraacetic acid. The abbreviation "TFA" is art-recognized and refers to trifluoroacetic acid.

As a general matter, compositions specifying a percentage are by weight unless otherwise specified.

I. Tetrahydro[1,8]naphthyridine and Related Compounds

One aspect of the invention provides a compound represented by Formula I:

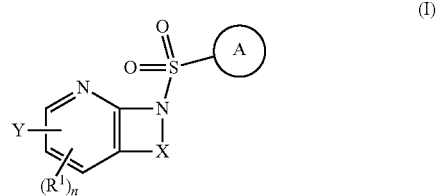

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkyl, $C_{1-6}$haloalkyl, $C_{1-6}$hydroxyalkyl, $C_{1-6}$alkoxy, $C_{1-6}$haloalkoxy, —N(R$^4$)(R$^5$), —CO$_2$R$^6$, —C(O)R$^6$, —CN, —C$_{1-4}$alkylene-C$_{1-4}$alkoxy, —C$_{1-4}$alkylene-N(R$^4$)(R$^5$), —C$_{1-4}$alkylene-CO$_2$R$^6$, —O—C$_{1-6}$alkylene-N(R$^4$)(R$^5$), —N(R$^4$)C(O)—C$_{1-6}$alkylene-N(R$^4$)(R$^5$), —S(O)$_p$C$_{1-6}$alkyl, —SO$_2$N(R$^4$)(R$^5$), —N(R$^4$)SO$_2$ (C$_{1-6}$alkyl), —C(O)N(R$^4$)(R$^5$), and —N(R$^4$)C(O)N(R$^4$)(R$^5$);

X is —O—[C(R$^6$)(R$^7$)]-[C(R$^6$)$_2$]$_m$-ψ, —O—C(R$^6$)$_2$—C(R$^6$)(R$^7$)—C(R$^6$)$_2$-ψ, —O—C(R$^6$)$_2$—C(R$^6$)(R$^7$)-ψ, —C(R$^6$)$_2$—[C(R$^6$)(R$^7$)]-[C(R$^6$)$_2$]$_m$-ψ, —C(O)—[C(R$^6$)(R$^7$)]-[C(R$^6$)$_2$]$_m$-ψ, —C(R$^6$)$_2$—N(R$^8$)—[C(R$^6$)(R$^7$)]-[C(R$^6$)$_2$]$_m$-ψ, —C(R$^6$)=N-ψ, —C(R$^6$)$_2$C(R$^6$)=N-ψ, —N=C(R$^6$)-ψ, or —N=C(R$^6$)C(R$^6$)$_2$—ψ; wherein ψ is a bond to the sulfonamide ring nitrogen atom in Formula I;

Y is —N(R$^2$)(R$^3$) or —O-aralkyl, wherein said aralkyl is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N(R$^4$)(R$^5$), —CN, —CO$_2$—C$_{1-6}$alkyl, —C(O)—C$_{1-6}$alkyl, —C(O)N(R$^4$)(R$^5$), —S(O)$_p$C$_{1-6}$alkyl, —SO$_2$N(R$^4$)(R$^5$), and —N(R$^4$)SO$_2$(C$_{1-6}$alkyl);

R$^1$ represents independently for each occurrence hydrogen, halogen, or $C_{1-6}$alkyl;

R$^2$ is —C(O)-aryl, —C(O)-aralkyl, —C(O)—[C(R$^6$)$_2$]$_m$-cycloalkyl, —C(O)—[C(R$^6$)$_2$]$_m$-heterocyclyl, —C(O)—C$_{1-8}$alkyl, —C(O)—C$_{1-6}$alkylene-C$_{1-6}$alkoxyl, —C(O)—C$_{1-6}$alkylene-cycloalkyl, or —C(O)—C$_{1-6}$alkylene-heterocycloalkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N(R$^4$)(R$^5$), —CN, —CO$_2$—C$_{1-6}$alkyl, —C(O)—C$_{1-6}$alkyl, —C(O)N(R$^4$)(R$^5$), —S(O)$_p$C$_{1-6}$alkyl, —SO$_2$N(R$^4$)(R$^5$), and —N(R$^4$)SO$_2$(C$_{1-6}$alkyl);

R$^3$ is hydrogen or $C_{1-6}$alkyl;

R$^4$ and R$^5$ each represent independently for each occurrence hydrogen or $C_{1-6}$alkyl; or R$^4$ and R$^5$ taken together with the nitrogen atom to which they are attached form a 3-7 membered heterocyclic ring;

R$^6$ represents independently for each occurrence hydrogen or $C_{1-6}$alkyl;

R$^7$ is hydrogen, hydroxyl, $C_{1-6}$hydroxyalkyl, $C_{1-6}$alkyl, $C_{1-6}$haloalkyl, —CO$_2$R$^6$, $C_{1-6}$alkylene-CO$_2$R$^6$, $C_{1-4}$hydroxyalkylene-CO$_2$R$^6$, —N(R$^4$)(R$^5$), $C_{1-6}$alkylene-N(R$^4$)(R$^5$), $C_{1-6}$hydroxyalkylene-N(R$^4$)(R$^5$), —N(R$^4$)C(O)R$^9$, $C_{1-6}$alkylene-N(R$^4$)C(O)R$^9$, $C_{1-6}$alkylene-C(O)N(R$^4$)(R$^5$), —N(R$^4$)CO$_2$—C$_{1-6}$alkyl, or $C_{1-6}$alkylene-N(R$^4$)(C(O)N(R$^4$)

($R^5$); or $R^7$ is heterocycloalkyl or $C_{1-4}$alkylene-heterocycloalkyl, wherein the heterocycloalkyl is optionally substituted with 1, 2, or 3 substituents independently selected from the group consisting of oxo, halogen, hydroxyl, $C_{1-6}$alkyl, $C_{1-6}$haloalkyl, $C_{1-6}$hydroxyalkyl, $C_{1-6}$alkoxy, and $C_{1-6}$haloalkoxy;

$R^8$ is hydrogen, $C_{1-6}$alkyl, or —C(O)—$C_{1-6}$alkyl;

$R^9$ is hydrogen, $C_{1-6}$alkyl, $C_{1-6}$hydroxyalkyl, $C_{1-6}$alkylene-N($R^4$)($R^5$), or $C_{1-6}$alkylene-N($R^4$)C(O)—$C_{1-6}$alkyl;

n is 1 or 2; and m and p each represent independently for each occurrence 0, 1, or 2.

In certain embodiments, A is aryl or heteroaryl; each of which is optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is aryl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is phenyl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is phenyl optionally substituted with 1, 2, or 3 substituents independently selected from the group consisting of halogen and $C_{1-6}$haloalkyl. In certain embodiments, at least one substituent is attached at the meta-position of the phenyl ring.

In certain other embodiments, A is heteroaryl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy.

In certain embodiments, A is heterocycloalkyl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain embodiments, A is piperidine or pyrrolidine, each of which is optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy.

In certain embodiments, X is —O—[C($R^6$)($R^7$)]-[C($R^6$)$_2$]$_m$-ψ. In certain other embodiments, X is —C($R^6$)$_2$—[C($R^6$)($R^7$)]-[C($R^6$)$_2$]$_m$-ψ. In certain other embodiments, X is —C(O)—[C($R^6$)($R^7$)]-[C($R^6$)$_2$]$_m$-ψ. In certain other embodiments, X is —C($R^6$)$_2$—N($R^8$)—[C($R^6$)($R^7$)]—[C($R^6$)$_2$]$_m$-ψ. In certain other embodiments, X is —C($R^6$)=N-ψ.

In certain embodiments, Y is —N($R^2$)($R^3$). In certain embodiments, Y is —O-aralkyl optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N($R^4$)($R^5$), —CN, —CO$_2$—$C_{1-6}$alkyl, —C(O)—$C_{1-6}$alkyl, —C(O)N($R^4$)($R^5$), —S(O)$_p$$C_{1-6}$alkyl, —SO$_2$N($R^4$)($R^5$), and —N($R^4$)SO$_2$($C_{1-6}$alkyl). In certain other embodiments, Y is —O-aralkyl optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N($R^4$)($R^5$), —CN, —CO$_2$—$C_{1-6}$alkyl, and —C(O)—$C_{1-6}$alkyl. In certain other embodiments, Y is —O— benzyl optionally substituted with 1, 2, or 3 substituents independently selected from the group consisting of halogen, $C_{1-6}$alkyl, and $C_{1-6}$haloalkyl.

In certain embodiments, $R^1$ is hydrogen.

In certain embodiments, $R^2$ is —C(O)-aryl or —C(O)-aralkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, and $C_{1-6}$haloalkyl. In certain other embodiments, $R^2$ is —C(O)-aryl or —C(O)-aralkyl; each of which is substituted with 2 substituents independently selected from the group consisting of halogen, hydroxyl, $C_{1-6}$alkoxy, $C_{1-6}$haloalkoxy, $C_{1-6}$alkyl, and $C_{1-6}$haloalkyl, and said substituents are located at the ortho-positions of the aromatic ring. In certain other embodiments, $R^2$ is —C(O)-phenyl or —C(O)-benzyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, and $C_{1-6}$haloalkyl. In certain other embodiments, $R^2$ is —C(O)-phenyl or —C(O)-benzyl; each of which is optionally substituted with 1, 2, or 3 substituents independently selected from the group consisting of halogen, $C_{1-6}$alkyl, and $C_{1-6}$haloalkyl. In certain other embodiments, $R^2$ is represented by:

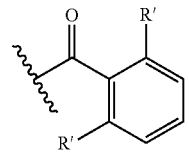

wherein each R' is independently halogen, hydroxyl, $C_{1-6}$alkoxy, $C_{1-6}$haloalkoxy, $C_{1-6}$alkyl, or $C_{1-6}$haloalkyl. In certain other embodiments, $R^2$ is represented by:

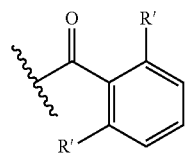

wherein each R' is independently halogen, $C_{1-6}$alkyl, or $C_{1-6}$haloalkyl.

In certain other embodiments, $R^2$ is represented by:

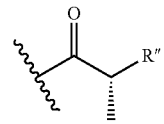

wherein R" is $C_{1-6}$alkyl, aryl, or heterocyclyl, each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N($R^4$)($R^5$), —CN, —CO$_2$—$C_{1-6}$alkyl, —C(O)—$C_{1-6}$alkyl, —C(O)N($R^4$)($R^5$), —S(O)$_p$$C_{1-6}$alkyl, —SO$_2$N($R^4$)($R^5$), and —N($R^4$)SO$_2$($C_{1-6}$alkyl). In certain embodiments, R" is phenyl optionally substituted with 1, 2, or 3 substituents independently selected from the group consisting of halogen, $C_{1-6}$alkyl, and $C_{1-6}$haloalkyl.

In certain embodiments, $R^3$ is hydrogen.

In certain embodiments, $R^7$ is hydrogen. In certain other embodiments, $R^7$ is hydroxyl, $C_{1-6}$hydroxyalkyl, $C_{1-6}$alkyl, $C_{1-6}$haloalkyl, —CO$_2$$R^6$, $C_{1-6}$alkylene-CO$_2$$R^6$, $C_{1-4}$hydroxyalkylene-CO$_2$$R^6$, —N($R^4$)($R^5$), $C_{1-6}$alkylene-N($R^4$)($R^5$), $C_{1-6}$hydroxyalkylene-N($R^4$)($R^5$), —N($R^4$)C(O)$R^9$, $C_{1-6}$alkylene-N($R^4$)C(O)$R^9$, $C_{1-6}$alkylene-C(O)N($R^4$)($R^5$), —N($R^4$)CO$_2$—$C_{1-6}$alkyl, or —N($R^4$)C(O)$R^9$. In certain other embodiments, $R^7$ is $C_{1-6}$hydroxyalkyl, $C_{1-6}$alkyl, $C_{1-6}$alkylene-$CO_2R^6$, —$N(R^4)(R^5)$, $C_{1-6}$alkylene-$N(R^4)$ $(R^5)$, or $C_{1-6}$alkylene-$N(R^4)C(O)R^9$. In certain other embodiments, $R^7$ is $C_{1-3}$hydroxyalkyl, methyl, ethyl, or $C_{1-3}$alkylene-$N(H)C(O)$—$C_{1-4}$alkyl.

In certain other embodiments, $R^7$ is heterocycloalkyl or $C_{1-4}$alkylene-heterocycloalkyl, wherein the heterocycloalkyl is optionally substituted with 1, 2, or 3 substituents independently selected from the group consisting of oxo, halogen, hydroxyl, $C_{1-6}$ alkyl, $C_{1-6}$haloalkyl, $C_{1-6}$hydroxyalkyl, $C_{1-6}$alkoxy, and $C_{1-6}$haloalkoxy.

Another aspect of the invention provides a compound represented by Formula I-A:

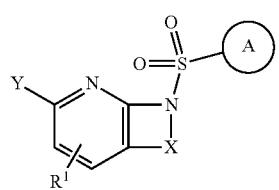

(I-A)

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkyl, $C_{1-6}$haloalkyl, $C_{1-6}$hydroxyalkyl, $C_{1-6}$alkoxy, $C_{1-6}$haloalkoxy, —$N(R^4)(R^5)$, —$CO_2R^6$, —$C(O)R^6$, —CN, —$C_{1-4}$alkylene-$C_{1-4}$alkoxy, —$C_{1-4}$alkylene-$N(R^4)(R^5)$, —$C_{1-4}$alkylene-$CO_2R^6$, —O—$C_{1-6}$alkylene-$N(R^4)(R^5)$, —$N(R^4)C(O)$—$C_{1-6}$alkylene-$N(R^4)(R^5)$, —$S(O)_pC_{1-6}$alkyl, —$SO_2N(R^4)(R^5)$, —$N(R^4)SO_2(C_{1-6}$alkyl$)$, —$C(O)N(R^4)(R^5)$, and —$N(R^4)C(O)N(R^4)(R^5)$;

X is —O—[C($R^6$)($R^7$)]-[C($R^6$)$_2$]$_m$-ψ, —O—C($R^6$)$_2$—C($R^6$)($R^7$)—C($R^6$)$_2$-ψ, —O—C($R^6$)$_2$—C($R^6$)($R^7$)-ψ, —C($R^6$)$_2$—[C($R^6$)($R^7$)]-[C($R^6$)$_2$]$_m$-ψ, —C(O)—[C($R^6$)($R^7$)]—[C($R^6$)$_2$]$_m$-ψ, —C($R^6$)$_2$—N($R^8$)—[C($R^6$)($R^7$)]-[C($R^6$)$_2$]$_m$-ψ, —C($R^6$)=N-ψ, —C($R^6$)$_2$C($R^6$)=N-ψ, —N=C($R^6$)-ψ, or —N=C($R^6$)C($R^6$)$_2$-ψ; wherein ψ is a bond to the sulfonamide ring nitrogen atom in Formula I-A;

Y is —$N(R^2)(R^3)$ or —O-aralkyl, wherein said aralkyl is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —$N(R^4)(R^5)$, —CN, —$CO_2$—$C_{1-6}$alkyl, —$C(O)$—$C_{1-6}$alkyl, —$C(O)N(R^4)(R^5)$, —$S(O)_pC_{1-6}$alkyl, —$SO_2N(R^4)(R^5)$, and —$N(R^4)SO_2(C_{1-6}$alkyl$)$; $R^1$ is hydrogen, halogen, or $C_{1-6}$alkyl;

$R^2$ is —C(O)-aryl, —C(O)-aralkyl, —C(O)—[C($R^6$)$_2$]$_m$-cycloalkyl, —C(O)—[C($R^6$)$_2$]$_m$-heterocyclyl, —C(O)—$C_{1-8}$alkyl, —C(O)—$C_{1-6}$alkylene-$C_{1-6}$alkoxyl, —C(O)—$C_{1-6}$alkylene-cycloalkyl, or —C(O)—$C_{1-6}$alkylene-heterocycloalkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —$N(R^4)(R^5)$, —CN, —$CO_2$—$C_{1-6}$alkyl, —$C(O)$—$C_{1-6}$alkyl, —$C(O)N(R^4)(R^5)$, —$S(O)_pC_{1-6}$alkyl, —$SO_2N(R^4)(R^5)$, and —$N(R^4)SO_2(C_{1-6}$alkyl$)$;

$R^3$ is hydrogen or $C_{1-6}$alkyl;

$R^4$ and $R^5$ each represent independently for each occurrence hydrogen or $C_{1-6}$alkyl; or $R^4$ and $R^5$ taken together with the nitrogen atom to which they are attached form a 3-7 membered heterocyclic ring;

$R^6$ represents independently for each occurrence hydrogen or $C_{1-6}$alkyl;

$R^7$ is hydrogen, hydroxyl, $C_{1-6}$hydroxyalkyl, $C_{1-6}$alkyl, $C_{1-6}$haloalkyl, —$CO_2R^6$, $C_{1-6}$alkylene-$CO_2R^6$, $C_{1-4}$hydroxyalkylene-$CO_2R^6$, —$N(R^4)(R^5)$, $C_{1-6}$alkylene-$N(R^4)(R^5)$, $C_{1-6}$hydroxyalkylene-$N(R^4)(R^5)$, —$N(R^4)C(O)R^9$, $C_{1-6}$alkylene-$N(R^4)C(O)R^9$, $C_{1-6}$alkylene-$C(O)N(R^4)(R^5)$, —$N(R^4)CO_2$—$C_{1-6}$alkyl, or $C_{1-6}$alkylene-$N(R^4)(C(O)N(R^4)(R^5)$; or $R^7$ is heterocycloalkyl or $C_{1-4}$alkylene-heterocycloalkyl, wherein the heterocycloalkyl is optionally substituted with 1, 2, or 3 substituents independently selected from the group consisting of oxo, halogen, hydroxyl, $C_{1-6}$alkyl, $C_{1-6}$haloalkyl, $C_{1-6}$hydroxyalkyl, $C_{1-6}$alkoxy, and $C_{1-6}$haloalkoxy;

$R^8$ is hydrogen, $C_{1-6}$alkyl, or —C(O)—$C_{1-6}$alkyl;

$R^9$ is hydrogen, $C_{1-6}$alkyl, $C_{1-6}$hydroxyalkyl, $C_{1-6}$alkylene-$N(R^4)(R^5)$, or $C_{1-6}$alkylene-$N(R^4)C(O)$—$C_{1-6}$alkyl; and m and p each represent independently for each occurrence 0, 1, or 2.

The definitions of variables in Formulae I-A above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where A is aryl, and $R^2$ is —C(O)-aryl. Further, the definitions of variables A, X, Y, $R^1$ to $R^9$, m, and p described in the preceding paragraphs in connection with Formula I are reiterated here for use in association with Formula I-A.

Another aspect of the invention provides a compound represented by Formula II:

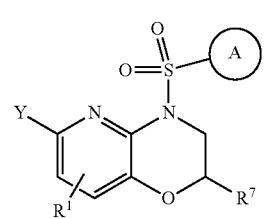

(II)

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkyl, $C_{1-6}$haloalkyl, $C_{1-6}$hydroxyalkyl, $C_{1-6}$alkoxy, $C_{1-6}$haloalkoxy, —$N(R^4)(R^5)$, —$CO_2R^6$, —$C(O)R^6$, —CN, —$C_{1-4}$alkylene-$C_{1-4}$alkoxy, and —$C_{1-4}$alkylene-$N(R^4)(R^5)$;

Y is —$N(R^2)(R^3)$ or —O-aralkyl, wherein said aralkyl is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —$N(R^4)(R^5)$, —CN, —$CO_2$—$C_{1-6}$alkyl, —$C(O)$—$C_{1-6}$alkyl, —$C(O)N(R^4)(R^5)$, —$S(O)_pC_{1-6}$alkyl, —$SO_2N(R^4)(R^5)$, and —$N(R^4)SO_2(C_{1-6}$alkyl$)$;

$R^1$ is hydrogen, halogen, or $C_{1-6}$alkyl;

$R^2$ is —C(O)-aryl, —C(O)-aralkyl, —C(O)—[C($R^6$)$_2$]$_m$-cycloalkyl, —C(O)—[C($R^6$)$_2$]$_m$-heterocyclyl, —C(O)—$C_{1-8}$alkyl, —C(O)—$C_{1-6}$alkylene-$C_{1-6}$alkoxyl, —C(O)—

$C_{1-6}$alkylene-cycloalkyl, or —C(O)—$C_{1-6}$alkylene-heterocycloalkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N($R^4$)($R^5$), —CN, —$CO_2$—$C_{1-6}$alkyl, —C(O)—$C_{1-6}$alkyl, —C(O)N($R^4$)($R^5$), —S(O)$_p$$C_{1-6}$alkyl, —$SO_2$N($R^4$)($R^5$), and —N($R^4$)$SO_2$($C_{1-6}$alkyl);

$R^3$ is hydrogen or $C_{1-6}$alkyl;

$R^4$ and $R^5$ each represent independently for each occurrence hydrogen or $C_{1-6}$alkyl; or $R^4$ and $R^5$ taken together with the nitrogen atom to which they are attached form a 3-7 membered heterocyclic ring;

$R^6$ represents independently for each occurrence hydrogen or $C_{1-6}$alkyl;

$R^7$ is hydrogen, hydroxyl, $C_{1-6}$hydroxyalkyl, $C_{1-6}$alkyl, $C_{1-6}$haloalkyl, —$CO_2R^6$, $C_{1-6}$alkylene-$CO_2R^6$, $C_{1-4}$hydroxyalkylene-$CO_2R^6$, —N($R^4$)($R^5$), $C_{1-6}$alkylene-N($R^4$)($R^5$), $C_{1-6}$hydroxyalkylene-N($R^4$)($R^5$), —N($R^4$)C(O)$R^9$, $C_{1-6}$alkylene-N($R^4$)C(O)$R^9$, $C_{1-6}$alkylene-C(O)N($R^4$)($R^5$), —N($R^4$)$CO_2$—$C_{1-6}$alkyl, or $C_{1-6}$alkylene-N($R^4$)(C(O)N($R^4$)($R^5$); or $R^7$ is heterocycloalkyl or $C_{1-4}$alkylene-heterocycloalkyl, wherein the heterocycloalkyl is optionally substituted with 1, 2, or 3 substituents independently selected from the group consisting of oxo, halogen, hydroxyl, $C_{1-6}$alkyl, $C_{1-6}$haloalkyl, $C_{1-6}$hydroxyalkyl, $C_{1-6}$alkoxy, and $C_{1-6}$haloalkoxy;

$R^9$ is hydrogen, $C_{1-6}$alkyl, $C_{1-6}$hydroxyalkyl, $C_{1-6}$alkylene-N($R^4$)($R^5$), or $C_{1-6}$alkylene-N($R^4$)C(O)—$C_{1-6}$alkyl; and m and p each represent independently for each occurrence 0, 1, or 2.

In certain embodiments, A is aryl or heteroaryl; each of which is optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is aryl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is phenyl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is phenyl optionally substituted with 1, 2, or 3 substituents independently selected from the group consisting of halogen and $C_{1-6}$haloalkyl. In certain embodiments, at least one substituent is attached at the meta-position of the phenyl ring.

In certain other embodiments, A is heterocycloalkyl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain embodiments, A is piperidine or pyrrolidine, each of which is optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy.

In certain embodiments, Y is —N($R^2$)($R^3$). In certain embodiments, Y is —O-aralkyl optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N($R^4$)($R^5$), —CN, —$CO_2$—$C_{1-6}$alkyl, —C(O)—$C_{1-6}$alkyl, —C(O)N($R^4$)($R^5$), —S(O)$_p$$C_{1-6}$alkyl, —$SO_2$N($R^4$)($R^5$), and —N($R^4$)$SO_2$($C_{1-6}$alkyl). In certain other embodiments, Y is —O-aralkyl optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N($R^4$)($R^5$), —CN, —$CO_2$—$C_{1-6}$alkyl, and —C(O)—$C_{1-6}$alkyl. In certain other embodiments, Y is —O-benzyl optionally substituted with 1, 2, or 3 substituents independently selected from the group consisting of halogen, $C_{1-6}$alkyl, and $C_{1-6}$haloalkyl.

In certain embodiments, $R^1$ is hydrogen.

In certain embodiments, $R^2$ is —C(O)-aryl or —C(O)-aralkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, and $C_{1-6}$haloalkyl. In certain other embodiments, $R^2$ is —C(O)-aryl or —C(O)-aralkyl; each of which is substituted with 2 substituents independently selected from the group consisting of halogen, hydroxyl, $C_{1-6}$alkoxy, $C_{1-6}$haloalkoxy, $C_{1-6}$alkyl, and $C_{1-6}$haloalkyl, and said substituents are located at the ortho-positions of the aromatic ring. In certain other embodiments, $R^2$ is —C(O)-phenyl or —C(O)-benzyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, and $C_{1-6}$haloalkyl. In certain other embodiments, $R^2$ is —C(O)-phenyl or —C(O)-benzyl; each of which is optionally substituted with 1, 2, or 3 substituents independently selected from the group consisting of halogen, $C_{1-6}$alkyl, and $C_{1-6}$haloalkyl. In certain other embodiments, $R^2$ is represented by:

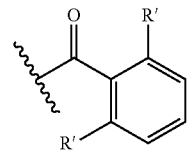

wherein each R' is independently halogen, hydroxyl, $C_{1-6}$alkoxy, $C_{1-6}$haloalkoxy, $C_{1-6}$alkyl, or $C_{1-6}$haloalkyl. In certain other embodiments, $R^2$ is represented by:

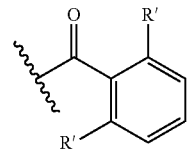

wherein each R' is independently halogen, $C_{1-6}$alkyl, or $C_{1-6}$haloalkyl.

In certain embodiments, $R^2$ is represented by:

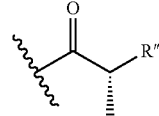

wherein R" is $C_{1-6}$alkyl, aryl, or heterocyclyl, each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N($R^4$)($R^5$), —CN, —$CO_2$—$C_{1-6}$alkyl, —C(O)—$C_{1-6}$alkyl, —C(O)N($R^4$)($R^5$), —S(O)$_p$$C_{1-6}$alkyl, —$SO_2$N($R^4$)($R^5$), and —N($R^4$)$SO_2$($C_{1-6}$alkyl). In certain embodiments, R" is phenyl optionally substituted with 1, 2, or 3 substituents independently selected from the group consisting of halogen, $C_{1-6}$alkyl, and $C_{1-6}$haloalkyl.

In certain embodiments, $R^3$ is hydrogen.

In certain embodiments, $R^7$ is hydrogen. In certain other embodiments, $R^7$ is hydroxyl, $C_{1-6}$hydroxyalkyl, $C_{1-6}$alkyl, $C_{1-6}$haloalkyl, —$CO_2R^6$, $C_{1-6}$alkylene-$CO_2R^6$, $C_{1-4}$hydroxyalkylene-$CO_2R^6$, —$N(R^4)(R^5)$, $C_{1-6}$alkylene-$N(R^4)(R^5)$, $C_{1-6}$hydroxyalkylene-$N(R^4)(R^5)$, —$N(R^4)C(O)R^9$, $C_{1-6}$alkylene-$N(R^4)C(O)R^9$, $C_{1-6}$alkylene-$C(O)N(R^4)(R^5)$, —$N(R^4)CO_2$—$C_{1-6}$alkyl, or —$N(R^4)C(O)R^9$. In certain other embodiments, $R^7$ is $C_{1-6}$hydroxyalkyl, $C_{1-6}$alkyl, $C_{1-6}$alkylene-$CO_2R^6$, $C_{1-6}$alkylene-$N(R^4)(R^5)$, or $C_{1-6}$alkylene-$N(R^4)C(O)R^9$. In certain other embodiments, $R^7$ is $C_{1-3}$hydroxyalkyl, methyl, ethyl, or $C_{1-3}$alkylene-$N(H)C(O)$—$C_{1-4}$alkyl.

Another aspect of the invention provides a compound represented by Formula II-A:

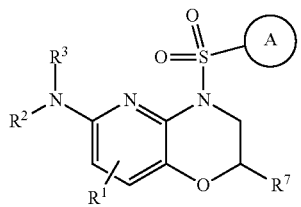

(II-A)

or a pharmaceutically acceptable salt or solvate thereof;
wherein:
A is aryl, heteroaryl, or heterocycloalkyl; each of which is optionally substituted with 1, 2, or 3 substituents independently selected from the group consisting of halogen, hydroxyl, $C_{1-6}$alkyl, $C_{1-6}$haloalkyl, $C_{1-6}$alkoxy, and $C_{1-6}$haloalkoxy; $R^1$ is hydrogen;

$R^2$ is —C(O)-phenyl substituted with 2 substituents independently selected from the group consisting of halogen, $C_{1-6}$alkyl, and $C_{1-6}$haloalkyl, wherein the substituents are located at the ortho positions of the phenyl ring;

$R^3$ is hydrogen;

$R^4$ and $R^5$ each represent independently for each occurrence hydrogen or $C_{1-6}$alkyl; or $R^4$ and $R^5$ taken together with the nitrogen atom to which they are attached form a 3-7 membered heterocyclic ring;

$R^6$ represents independently for each occurrence hydrogen or $C_{1-6}$alkyl;

$R^7$ is hydrogen, hydroxyl, $C_{1-6}$hydroxyalkyl, $C_{1-6}$alkyl, $C_{1-6}$haloalkyl, —$CO_2R^6$, $C_{1-6}$alkylene-$CO_2R^6$, $C_{1-4}$hydroxyalkylene-$CO_2R^6$, —$N(R^4)(R^5)$, $C_{1-6}$alkylene-$N(R^4)(R^5)$, $C_{1-6}$hydroxyalkylene-$N(R^4)(R^5)$, —$N(R^4)C(O)R^9$, $C_{1-6}$alkylene-$N(R^4)C(O)R^9$, $C_{1-6}$alkylene-$C(O)N(R^4)(R^5)$, —$N(R^4)CO_2$—$C_{1-6}$alkyl, or $C_{1-6}$alkylene-$N(R^4)(C(O)N(R^4)(R^5)$; or $R^7$ is heterocycloalkyl or $C_{1-4}$alkylene-heterocycloalkyl, wherein the heterocycloalkyl is optionally substituted with 1, 2, or 3 substituents independently selected from the group consisting of oxo, halogen, hydroxyl, $C_{1-6}$alkyl, $C_{1-6}$haloalkyl, $C_{1-6}$hydroxyalkyl, $C_{1-6}$alkoxy, and $C_{1-6}$haloalkoxy;

$R^9$ is hydrogen, $C_{1-6}$alkyl, $C_{1-6}$hydroxyalkyl, $C_{1-6}$alkylene-$N(R^4)(R^5)$, or $C_{1-6}$alkylene-$N(R^4)C(O)$—$C_{1-6}$alkyl; and m and p each represent independently for each occurrence 0, 1, or 2.

In certain embodiments, A is aryl or heteroaryl; each of which is optionally substituted with 1, 2, or 3 substituents independently selected from the group consisting of halogen, hydroxyl, $C_{1-6}$alkyl, $C_{1-6}$haloalkyl, $C_{1-6}$alkoxy, and $C_{1-6}$haloalkoxy. In certain other embodiments, A is aryl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is phenyl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is phenyl optionally substituted with 1, 2, or 3 substituents independently selected from the group consisting of halogen and $C_{1-6}$haloalkyl. In certain embodiments, at least one substituent is attached at the meta-position of the phenyl ring.

In certain other embodiments, A is heterocycloalkyl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain embodiments, A is piperidine or pyrrolidine, each of which is optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy.

In certain embodiments, $R^2$ is represented by:

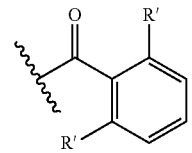

wherein each R' is independently fluoro, chloro, or $C_{1-6}$haloalkyl.

In certain embodiments, $R^7$ is hydrogen. In certain other embodiments, $R^7$ is $C_{1-6}$hydroxyalkyl, $C_{1-6}$alkyl, $C_{1-6}$haloalkyl, —$CO_2R^6$, $C_{1-6}$alkylene-$CO_2R^6$, $C_{1-4}$hydroxyalkylene-$CO_2R^6$, —$N(R^4)(R^5)$, $C_{1-6}$alkylene-$N(R^4)(R^5)$, $C_{1-6}$hydroxyalkylene-$N(R^4)(R^5)$, —$N(R^4)C(O)R^9$, $C_{1-6}$alkylene-$N(R^4)C(O)R^9$, $C_{1-6}$alkylene-$C(O)N(R^4)(R^5)$, —$N(R^4)CO_2$—$C_{1-6}$alkyl, or —$N(R^4)C(O)R^9$. In certain other embodiments, $R^7$ is $C_{1-6}$hydroxyalkyl, $C_{1-6}$alkyl, $C_{1-6}$ alkylene-$CO_2R^6$, $C_{1-6}$alkylene-$N(R^4)(R^5)$, or $C_{1-6}$alkylene-$N(R^4)C(O)R^9$. In certain other embodiments, $R^7$ is $C_{1-3}$hydroxyalkyl, methyl, ethyl, or $C_{1-3}$alkylene-$N(H)C(O)$—$C_{1-4}$alkyl.

Another aspect of the invention provides a compound represented by Formula III:

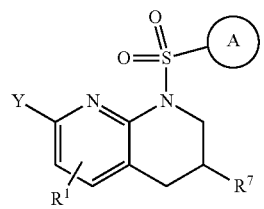

(III)

or a pharmaceutically acceptable salt or solvate thereof;
wherein:
A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkyl, $C_{1-6}$haloalkyl, $C_{1-6}$hydroxyalkyl, $C_{1-6}$alkoxy, $C_{1-6}$haloalkoxy, —$N(R^4)(R^5)$, —$CO_2R^6$, —$C(O)R^6$, —$CN$, —$C_{1-4}$alkylene-$C_{1-4}$alkoxy, and —$C_{1-4}$alkylene-$N(R^4)(R^5)$;

Y is —N(R²)(R³) or —O-aralkyl, wherein said aralkyl is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N(R⁴)(R⁵), —CN, —CO₂—$C_{1-6}$alkyl, —C(O)—$C_{1-6}$alkyl, —C(O)N(R⁴)(R⁵), —S(O)$_p$$C_{1-6}$alkyl, —SO₂N(R⁴)(R⁵), and —N(R⁴)SO₂($C_{1-6}$alkyl);

R¹ is hydrogen, halogen, or $C_{1-6}$alkyl;

R² is —C(O)-aryl, —C(O)-aralkyl, —C(O)—[C(R⁶)₂]$_m$-cycloalkyl, —C(O)—[C(R⁶)₂]$_m$-heterocyclyl, —C(O)—$C_{1-8}$alkyl, —C(O)—$C_{1-6}$alkylene-$C_{1-6}$alkoxyl, —C(O)—$C_{1-6}$alkylene-cycloalkyl, or —C(O)—$C_{1-6}$alkylene-heterocycloalkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N(R⁴)(R⁵), —CN, —CO₂—$C_{1-6}$alkyl, —C(O)—$C_{1-6}$alkyl, —C(O)N(R⁴)(R⁵), —S(O)$_p$$C_{1-6}$alkyl, —SO₂N(R⁴)(R⁵), and —N(R⁴)SO₂($C_{1-6}$alkyl);

R³ is hydrogen or $C_{1-6}$alkyl;

R⁴ and R⁵ each represent independently for each occurrence hydrogen or $C_{1-6}$alkyl; or R⁴ and R⁵ taken together with the nitrogen atom to which they are attached form a 3-7 membered heterocyclic ring;

R⁶ represents independently for each occurrence hydrogen or $C_{1-6}$alkyl;

R⁷ is hydrogen, hydroxyl, $C_{1-6}$hydroxyalkyl, $C_{1-6}$alkyl, $C_{1-6}$haloalkyl, —CO₂R⁶, $C_{1-6}$alkylene-CO₂R⁶, $C_{1-4}$hydroxyalkylene-CO₂R⁶, —N(R⁴)(R⁵), $C_{1-6}$alkylene-N(R⁴)(R⁵), $C_{1-6}$hydroxyalkylene-N(R⁴)(R⁵), —N(R⁴)C(O)R⁹, $C_{1-6}$alkylene-N(R⁴)C(O)R⁹, $C_{1-6}$alkylene-C(O)N(R⁴)(R⁵), —N(R⁴)CO₂—$C_{1-6}$alkyl, or $C_{1-6}$alkylene-N(R⁴)(C(O)N(R⁴)(R⁵); or R⁷ is heterocycloalkyl or $C_{1-4}$alkylene-heterocycloalkyl, wherein the heterocycloalkyl is optionally substituted with 1, 2, or 3 substituents independently selected from the group consisting of oxo, halogen, hydroxyl, $C_{1-6}$alkyl, $C_{1-6}$haloalkyl, $C_{1-6}$hydroxyalkyl, $C_{1-6}$alkoxy, and $C_{1-6}$haloalkoxy;

R⁹ is hydrogen, $C_{1-6}$alkyl, $C_{1-6}$hydroxyalkyl, $C_{1-6}$alkylene-N(R⁴)(R⁵), or $C_{1-6}$alkylene-N(R⁴)C(O)—$C_{1-6}$alkyl; and m and p each represent independently for each occurrence 0, 1, or 2.

In certain embodiments, A is aryl or heteroaryl; each of which is optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is aryl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is phenyl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is phenyl optionally substituted with 1, 2, or 3 substituents independently selected from the group consisting of halogen and $C_{1-6}$haloalkyl. In certain embodiments, at least one substituent is attached at the meta-position of the phenyl ring.

In certain other embodiments, A is heterocycloalkyl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain embodiments, A is piperidine or pyrrolidine, each of which is optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy.

In certain embodiments, Y is —N(R²)(R³). In certain embodiments, Y is —O-aralkyl optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N(R⁴)(R⁵), —CN, —CO₂—$C_{1-6}$alkyl, —C(O)—$C_{1-6}$alkyl, —C(O)N(R⁴)(R⁵), —S(O)$_p$$C_{1-6}$alkyl, —SO₂N(R⁴)(R⁵), and —N(R⁴)SO₂($C_{1-6}$alkyl). In certain other embodiments, Y is —O-aralkyl optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N(R⁴)(R⁵), —CN, —CO₂—$C_{1-6}$alkyl, and —C(O)—$C_{1-6}$alkyl. In certain other embodiments, Y is —O-benzyl optionally substituted with 1, 2, or 3 substituents independently selected from the group consisting of halogen, $C_{1-6}$alkyl, and $C_{1-6}$haloalkyl.

In certain embodiments, R¹ is hydrogen.

In certain embodiments, R² is —C(O)-aryl or —C(O)-aralkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, and $C_{1-6}$haloalkyl. In certain other embodiments, R² is —C(O)-aryl or —C(O)-aralkyl; each of which is substituted with 2 substituents independently selected from the group consisting of halogen, hydroxyl, $C_{1-6}$alkoxy, $C_{1-6}$haloalkoxy, $C_{1-6}$alkyl, and $C_{1-6}$haloalkyl, and said substituents are located at the ortho-positions of the aromatic ring. In certain other embodiments, R² is —C(O)-phenyl or —C(O)-benzyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, and $C_{1-6}$haloalkyl. In certain other embodiments, R² is —C(O)-phenyl or —C(O)-benzyl; each of which is optionally substituted with 1, 2, or 3 substituents independently selected from the group consisting of halogen, $C_{1-6}$alkyl, and $C_{1-6}$haloalkyl. In certain other embodiments, R² is represented by:

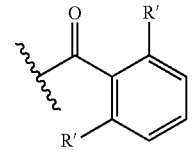

wherein each R' is independently halogen, hydroxyl, $C_{1-6}$alkoxy, $C_{1-6}$haloalkoxy, $C_{1-6}$alkyl, or $C_{1-6}$haloalkyl. In certain other embodiments, R² is represented by:

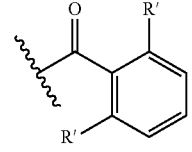

wherein each R' is independently halogen, $C_{1-6}$alkyl, or $C_{1-6}$haloalkyl.

In certain embodiments, R² is represented by:

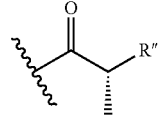

wherein R" is $C_{1-6}$alkyl, aryl, or heterocyclyl, each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N(R⁴)(R⁵), —CN, —CO₂—C₁₋₆alkyl, —C(O)—C₁₋₆alkyl, —C(O)N(R⁴)(R⁵), —S(O)ₚC₁₋₆alkyl, —SO₂N(R⁴)(R⁵), and —N(R⁴)SO₂(C₁₋₆alkyl). In certain embodiments, R" is phenyl optionally substituted with 1, 2, or 3 substituents independently selected from the group consisting of halogen, C₁₋₆alkyl, and C₁₋₆haloalkyl.

In certain embodiments, R³ is hydrogen.

In certain embodiments, R⁷ is hydrogen. In certain other embodiments R⁷ is hydroxyl, C₁₋₆hydroxyalkyl, C₁₋₆alkyl, C₁₋₆haloalkyl, —CO₂R⁶, C₁₋₆alkylene-CO₂R⁶, C₁₋₄hydroxyalkylene-CO₂R⁶, —N(R⁴)(R⁵), C₁₋₆alkylene-N(R⁴)(R⁵), C₁₋₆hydroxyalkylene-N(R⁴)(R⁵), —N(R⁴)C(O)R⁹, C₁₋₆alkylene-N(R⁴)C(O)R⁹, C₁₋₆alkylene-C(O)N(R⁴)(R⁵), —N(R⁴)CO₂—C₁₋₆alkyl, or —N(R⁴)C(O)R⁹. In certain other embodiments, R⁷ is C₁₋₆hydroxyalkyl, C₁₋₆alkyl, C₁₋₆alkylene-CO₂R⁶, —N(R⁴)(R⁵), C₁₋₆alkylene-N(R⁴)(R⁵), or C₁₋₆alkylene-N(R⁴)C(O)R⁹. In certain other embodiments, R⁷ is C₁₋₃hydroxyalkyl, methyl, ethyl, or C₁₋₃alkylene-N(H)C(O)—C₁₋₄alkyl.

Another aspect of the invention provides a compound represented by Formula III-A:

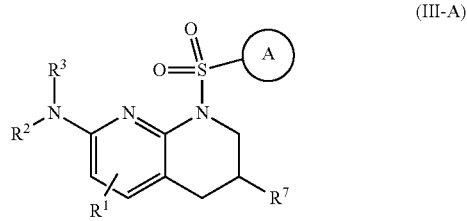

(III-A)

or a pharmaceutically acceptable salt or solvate thereof;
wherein:
A is aryl, heteroaryl, or heterocycloalkyl; each of which is optionally substituted with 1, 2, or 3 substituents independently selected from the group consisting of halogen, hydroxyl, C₁₋₆alkyl, C₁₋₆haloalkyl, C₁₋₆alkoxy, and C₁₋₆haloalkoxy;

R¹ is hydrogen;

R² is —C(O)-phenyl substituted with 2 substituents independently selected from the group consisting of halogen, C₁₋₆alkyl, and C₁₋₆haloalkyl, wherein the substituents are located at the ortho positions of the phenyl ring;

R³ is hydrogen;

R⁴ and R⁵ each represent independently for each occurrence hydrogen or C₁₋₆alkyl; or R⁴ and R⁵ taken together with the nitrogen atom to which they are attached form a 3-7 membered heterocyclic ring;

R⁶ represents independently for each occurrence hydrogen or C₁₋₆alkyl;

R⁷ is hydrogen, hydroxyl, C₁₋₆hydroxyalkyl, C₁₋₆alkyl, C₁₋₆haloalkyl, —CO₂R⁶, C₁₋₆alkylene-CO₂R⁶, C₁₋₄hydroxyalkylene-CO₂R⁶, —N(R⁴)(R⁵), C₁₋₆alkylene-N(R⁴)(R⁵), C₁₋₆hydroxyalkylene-N(R⁴)(R⁵), —N(R⁴)C(O)R⁹, C₁₋₆alkylene-N(R⁴)C(O)R⁹, C₁₋₆alkylene-C(O)N(R⁴)(R⁵), —N(R⁴)CO₂—C₁₋₆alkyl, or C₁₋₆alkylene-N(R⁴)(C(O)N(R⁴)(R⁵); or R⁷ is heterocycloalkyl or C₁₋₄alkylene-heterocycloalkyl, wherein the heterocycloalkyl is optionally substituted with 1, 2, or 3 substituents independently selected from the group consisting of oxo, halogen, hydroxyl, C₁₋₆alkyl, C₁₋₆haloalkyl, C₁₋₆hydroxyalkyl, C₁₋₆alkoxy, and C₁₋₆haloalkoxy;

R⁹ is hydrogen, C₁₋₆alkyl, C₁₋₆hydroxyalkyl, C₁₋₆alkylene-N(R⁴)(R⁵), or C₁₋₆alkylene-N(R⁴)C(O)—C₁₋₆alkyl; and m and p each represent independently for each occurrence 0, 1, or 2.

In certain embodiments, A is aryl or heteroaryl; each of which is optionally substituted with 1, 2, or 3 substituents independently selected from the group consisting of halogen, hydroxyl, C₁₋₆alkyl, C₁₋₆haloalkyl, C₁₋₆alkoxy, and C₁₋₆haloalkoxy. In certain other embodiments, A is aryl optionally substituted with 1, 2, or 3 substituents independently selected from the group consisting of halogen, C₁₋₆alkyl, C₁₋₆haloalkyl, C₁₋₆alkoxy, and C₁₋₆haloalkoxy. In certain other embodiments, A is phenyl optionally substituted with 1, 2, or 3 substituents independently selected from the group consisting of halogen, C₁₋₆alkyl, C₁₋₆haloalkyl, C₁₋₆alkoxy, and C₁₋₆haloalkoxy. In certain other embodiments, A is phenyl optionally substituted with 1, 2, or 3 substituents independently selected from the group consisting of halogen and C₁₋₆haloalkyl. In certain embodiments, at least one substituent is attached at the meta-position of the phenyl ring.

In certain other embodiments, A is heterocycloalkyl optionally substituted with 1, 2, or 3 substituents independently selected from the group consisting of halogen, C₁₋₆alkyl, C₁₋₆haloalkyl, C₁₋₆alkoxy, and C₁₋₆haloalkoxy. In certain embodiments, A is piperidine or pyrrolidine, each of which is optionally substituted with 1, 2, or 3 substituents independently selected from the group consisting of halogen, C₁₋₆alkyl, C₁₋₆haloalkyl, C₁₋₆alkoxy, and C₁₋₆ haloalkoxy.

In certain embodiments, R² is represented by:

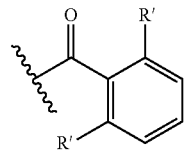

wherein each R' is independently fluoro, chloro, or C₁₋₆haloalkyl.

In certain embodiments, R⁷ is hydrogen. In certain other embodiments, R⁷ is C₁₋₆hydroxyalkyl, C₁₋₆alkyl, C₁₋₆haloalkyl, —CO₂R⁶, C₁₋₆alkylene-CO₂R⁶, C₁₋₄hydroxyalkylene-CO₂R⁶, —N(R⁴)(R⁵), C₁₋₆alkylene-N(R⁴)(R⁵), C₁₋₆hydroxyalkylene-N(R⁴)(R⁵), —N(R⁴)C(O)R⁹, C₁₋₆alkylene-N(R⁴)C(O)R⁹, C₁₋₆alkylene-C(O)N(R⁴)(R⁵), —N(R⁴)CO₂—C₁₋₆alkyl, or —N(R⁴)C(O)R⁹. In certain other embodiments, R⁷ is C₁₋₆hydroxyalkyl, C₁₋₆alkyl, C₁₋₆ alkylene-CO₂R⁶, C₁₋₆alkylene-N(R⁴)(R⁵), or C₁₋₆alkylene-N(R⁴)C(O)R⁹. In certain other embodiments, R⁷ is C₁₋₃hydroxyalkyl, methyl, ethyl, or C₁₋₃alkylene-N(H)C(O)—C₁₋₄alkyl.

Another aspect of the invention provides a compound represented by Formula IV:

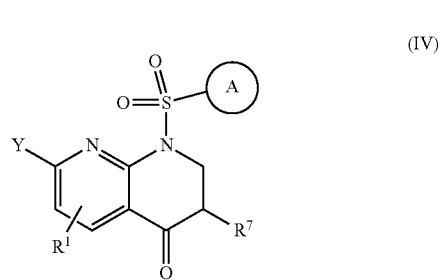

(IV)

or a pharmaceutically acceptable salt or solvate thereof;
wherein:
A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkyl, $C_{1-6}$haloalkyl, $C_{1-6}$hydroxyalkyl, $C_{1-6}$alkoxy, $C_{1-6}$haloalkoxy, —N(R$^4$)(R$^5$), —CO$_2$R$^6$, —C(O)R$^6$, —CN, —C$_{1-4}$alkylene-C$_{1-4}$alkoxy, and —C$_{1-4}$alkylene-N(R$^4$)(R$^5$);

Y is —N(R$^2$)(R$^3$) or —O-aralkyl, wherein said aralkyl is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N(R$^4$)(R$^5$), —CN, —CO$_2$—C$_{1-6}$alkyl, —C(O)—C$_{1-6}$alkyl, —C(O)N(R$^4$)(R$^5$), —S(O)$_p$C$_{1-6}$alkyl, —SO$_2$N(R$^4$)(R$^5$), and —N(R$^4$)SO$_2$(C$_{1-6}$alkyl);

R$^1$ is hydrogen, halogen, or C$_{1-6}$alkyl;

R$^2$ is —C(O)-aryl, —C(O)-aralkyl, —C(O)—[C(R$^6$)$_2$]$_m$-cycloalkyl, —C(O)—[C(R$^6$)$_2$]$_m$-heterocyclyl, —C(O)—C$_{1-8}$alkyl, —C(O)—C$_{1-6}$alkylene-C$_{1-6}$alkoxyl, —C(O)—C$_{1-6}$alkylene-cycloalkyl, or —C(O)—C$_{1-6}$alkylene-heterocycloalkyl; each of which is optionally substituted with 1, 2, or 3 substituents independently selected from the group consisting of halogen, hydroxyl, $C_{1-6}$alkoxy, $C_{1-6}$ haloalkoxy, $C_{1-6}$alkyl, $C_{1-6}$haloalkyl, —N(R$^4$)(R$^5$), —CN, —CO$_2$—C$_{1-6}$alkyl, —C(O)—C$_{1-6}$alkyl, —C(O)N(R$^4$)(R$^5$), —S(O)$_p$C$_{1-6}$alkyl, —SO$_2$N(R$^4$)(R$^5$), and —N(R$^4$)SO$_2$(C$_{1-6}$alkyl);

R$^3$ is hydrogen or C$_{1-6}$alkyl;

R$^4$ and R$^5$ each represent independently for each occurrence hydrogen or C$_{1-6}$alkyl; or R$^4$ and R$^5$ taken together with the nitrogen atom to which they are attached form a 3-7 membered heterocyclic ring;

R$^6$ represents independently for each occurrence hydrogen or C$_{1-6}$alkyl;

R$^7$ is hydrogen, hydroxyl, C$_{1-6}$hydroxyalkyl, C$_{1-6}$alkyl, C$_{1-6}$haloalkyl, —CO$_2$R$^6$, C$_{1-6}$alkylene-CO$_2$R$^6$, C$_{1-4}$hydroxyalkylene-CO$_2$R$^6$, —N(R$^4$)(R$^5$), C$_{1-6}$alkylene-N(R$^4$)(R$^5$), C$_{1-6}$hydroxyalkylene-N(R$^4$)(R$^5$), —N(R$^4$)C(O)R$^9$, C$_{1-6}$alkylene-N(R$^4$)C(O)R$^9$, C$_{1-6}$alkylene-C(O)N(R$^4$)(R$^5$), —N(R$^4$)CO$_2$—C$_{1-6}$alkyl, or C$_{1-6}$alkylene-N(R$^4$)(C(O)N(R$^4$)(R$^5$); or R$^7$ is heterocycloalkyl or C$_{1-4}$alkylene-heterocycloalkyl, wherein the heterocycloalkyl is optionally substituted with 1, 2, or 3 substituents independently selected from the group consisting of oxo, halogen, hydroxyl, C$_{1-6}$alkyl, C$_{1-6}$haloalkyl, C$_{1-6}$hydroxyalkyl, C$_{1-6}$alkoxy, and C$_{1-6}$haloalkoxy;

R$^9$ is hydrogen, C$_{1-6}$alkyl, C$_{1-6}$hydroxyalkyl, C$_{1-6}$alkylene-N(R$^4$)(R$^5$), or C$_{1-6}$alkylene-N(R$^4$)C(O)—C$_{1-6}$alkyl; and m and p each represent independently for each occurrence 0, 1, or 2.

In certain embodiments, A is aryl or heteroaryl; each of which is optionally substituted with 1, 2, or 3 substituents independently selected from the group consisting of halogen, C$_{1-6}$alkyl, C$_{1-6}$haloalkyl, C$_{1-6}$alkoxy, and C$_{1-6}$haloalkoxy. In certain other embodiments, A is aryl optionally substituted with 1, 2, or 3 substituents independently selected from the group consisting of halogen, C$_{1-6}$alkyl, C$_{1-6}$haloalkyl, C$_{1-6}$alkoxy, and C$_{1-6}$haloalkoxy. In certain other embodiments, A is phenyl optionally substituted with 1, 2, or 3 substituents independently selected from the group consisting of halogen, C$_{1-6}$alkyl, C$_{1-6}$haloalkyl, C$_{1-6}$alkoxy, and C$_{1-6}$haloalkoxy. In certain other embodiments, A is phenyl optionally substituted with 1, 2, or 3 substituents independently selected from the group consisting of halogen and C$_{1-6}$haloalkyl. In certain embodiments, at least one substituent is attached at the meta-position of the phenyl ring.

In certain other embodiments, A is heterocycloalkyl optionally substituted with 1, 2, or 3 substituents independently selected from the group consisting of halogen, C$_{1-6}$alkyl, C$_{1-6}$ haloalkyl, C$_{1-6}$alkoxy, and C$_{1-6}$haloalkoxy. In certain embodiments, A is piperidine or pyrrolidine, each of which is optionally substituted with 1, 2, or 3 substituents independently selected from the group consisting of halogen, C$_{1-6}$alkyl, C$_{1-6}$haloalkyl, C$_{1-6}$alkoxy, and C$_{1-6}$haloalkoxy.

In certain embodiments, Y is —N(R$^2$)(R$^3$). In certain embodiments, Y is —O-aralkyl optionally substituted with 1, 2, or 3 substituents independently selected from the group consisting of halogen, hydroxyl, C$_{1-6}$alkoxy, C$_{1-6}$haloalkoxy, C$_{1-6}$alkyl, C$_{1-6}$haloalkyl, —N(R$^4$)(R$^5$), —CN, —CO$_2$—C$_{1-6}$alkyl, —C(O)—C$_{1-6}$alkyl, —C(O)N(R$^4$)(R$^5$), —S(O)$_p$C$_{1-6}$alkyl, —SO$_2$N(R$^4$)(R$^5$), and —N(R$^4$)SO$_2$(C$_{1-6}$alkyl). In certain other embodiments, Y is —O-aralkyl optionally substituted with 1, 2, or 3 substituents independently selected from the group consisting of halogen, hydroxyl, C$_{1-6}$alkoxy, C$_{1-6}$haloalkoxy, C$_{1-6}$alkyl, C$_{1-6}$haloalkyl, —N(R$^4$)(R$^5$), —CN, —CO$_2$—C$_{1-6}$alkyl, and —C(O)—C$_{1-6}$alkyl. In certain other embodiments, Y is —O-benzyl optionally substituted with 1, 2, or 3 substituents independently selected from the group consisting of halogen, C$_{1-6}$alkyl, and C$_{1-6}$haloalkyl.

In certain embodiments, R$^1$ is hydrogen.

In certain embodiments, R$^2$ is —C(O)-aryl or —C(O)-aralkyl; each of which is optionally substituted with 1, 2, or 3 substituents independently selected from the group consisting of halogen, hydroxyl, C$_{1-6}$alkoxy, C$_{1-6}$haloalkoxy, C$_{1-6}$alkyl, and C$_{1-6}$haloalkyl. In certain other embodiments, R$^2$ is —C(O)-aryl or —C(O)-aralkyl; each of which is substituted with 2 substituents independently selected from the group consisting of halogen, hydroxyl, C$_{1-6}$alkoxy, C$_{1-6}$haloalkoxy, C$_{1-6}$alkyl, and C$_{1-6}$haloalkyl, and said substituents are located at the ortho-positions of the aromatic ring. In certain other embodiments, R$^2$ is —C(O)-phenyl or —C(O)-benzyl; each of which is optionally substituted with 1, 2, or 3 substituents independently selected from the group consisting of halogen, hydroxyl, C$_{1-6}$alkoxy, C$_{1-6}$haloalkoxy, C$_{1-6}$alkyl, and C$_{1-6}$haloalkyl. In certain other embodiments, R$^2$ is —C(O)-phenyl or —C(O)-benzyl; each of which is optionally substituted with 1, 2, or 3 substituents independently selected from the group consisting of halogen, C$_{1-6}$alkyl, and C$_{1-6}$haloalkyl. In certain other embodiments, R$^2$ is represented by:

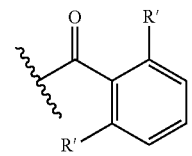

wherein each R' is independently halogen, hydroxyl, C$_{1-6}$alkoxy, C$_{1-6}$haloalkoxy, C$_{1-6}$alkyl, or C$_{1-6}$haloalkyl. In certain other embodiments, R$^2$ is represented by:

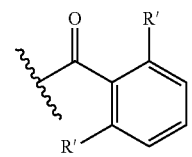

wherein each R' is independently halogen, C$_{1-6}$alkyl, or C$_{1-6}$haloalkyl.

In certain embodiments, $R^2$ is represented by:

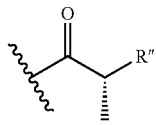

wherein R" is $C_{1-6}$alkyl, aryl, or heterocyclyl, each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —$N(R^4)(R^5)$, —CN, —$CO_2$—$C_{1-6}$alkyl, —C(O)—$C_{1-6}$alkyl, —C(O)$N(R^4)(R^5)$, —$S(O)_pC_{1-6}$alkyl, —$SO_2N(R^4)(R^5)$, and —$N(R^4)SO_2(C_{1-6}$alkyl). In certain embodiments, R" is phenyl optionally substituted with 1, 2, or 3 substituents independently selected from the group consisting of halogen, $C_{1-6}$alkyl, and $C_{1-6}$haloalkyl.

In certain embodiments, $R^3$ is hydrogen.

In certain embodiments, $R^7$ is hydrogen. In certain other embodiments $R^7$ is hydroxyl, $C_{1-6}$hydroxyalkyl, $C_{1-6}$alkyl, $C_{1-6}$haloalkyl, —$CO_2R^6$, $C_{1-6}$alkylene-$CO_2R^6$, $C_{1-4}$hydroxyalkylene-$CO_2R^6$, —$N(R^4)(R^5)$, $C_{1-6}$alkylene-$N(R^4)(R^5)$, $C_{1-6}$hydroxyalkylene-$N(R^4)(R^5)$, —$N(R^4)C(O)R^9$, $C_{1-6}$alkylene-$N(R^4)C(O)R^9$, $C_{1-6}$alkylene-$C(O)N(R^4)(R^5)$, —$N(R^4)CO_2$—$C_{1-6}$alkyl, or —$N(R^4)C(O)R^9$. In certain other embodiments, $R^7$ is $C_{1-6}$hydroxyalkyl, $C_{1-6}$alkyl, $C_{1-6}$alkylene-$CO_2R^6$, —$N(R^4)(R^5)$, $C_{1-6}$alkylene-$N(R^4)(R^5)$, or $C_{1-6}$alkylene-$N(R^4)C(O)R^9$. In certain other embodiments, $R^7$ is $C_{1-3}$hydroxyalkyl, methyl, ethyl, or $C_{1-3}$alkylene-$N(H)C(O)$—$C_{1-4}$alkyl.

Another aspect of the invention provides a compound of Formula V:

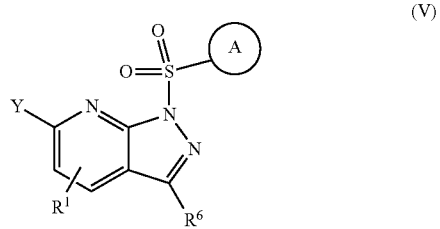

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkyl, $C_{1-6}$haloalkyl, $C_{1-6}$hydroxyalkyl, $C_{1-6}$alkoxy, $C_{1-6}$haloalkoxy, —$N(R^4)(R^5)$, —$CO_2R^6$, —$C(O)R^6$, —CN, —$C_{1-4}$alkylene-$C_{1-4}$alkoxy, and —$C_{1-4}$alkylene-$N(R^4)(R^5)$;

Y is —$N(R^2)(R^3)$ or —O-aralkyl, wherein said aralkyl is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —$N(R^4)(R^5)$, —CN, —$CO_2$—$C_{1-6}$alkyl, —C(O)—$C_{1-6}$alkyl, —C(O)$N(R^4)(R^5)$, —$S(O)_pC_{1-6}$alkyl, —$SO_2N(R^4)(R^5)$, and —$N(R^4)SO_2(C_{1-6}$alkyl);

$R^1$ is hydrogen, halogen, or $C_{1-6}$alkyl;

$R^2$ is —C(O)-aryl, —C(O)-aralkyl, —C(O)—$[C(R^6)_2]_m$-cycloalkyl, —C(O)—$[C(R^6)_2]_m$-heterocyclyl, —C(O)—$C_{1-8}$alkyl, —C(O)—$C_{1-6}$alkylene-$C_{1-6}$alkoxyl, —C(O)—$C_{1-6}$alkylene-cycloalkyl, or —C(O)—$C_{1-6}$alkylene-heterocycloalkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —$N(R^4)(R^5)$, —CN, —$CO_2$—$C_{1-6}$alkyl, —C(O)—$C_{1-6}$alkyl, —C(O)$N(R^4)(R^5)$, —$S(O)_pC_{1-6}$alkyl, —$SO_2N(R^4)(R^5)$, and —$N(R^4)SO_2(C_{1-6}$alkyl);

$R^3$ is hydrogen or $C_{1-6}$alkyl;

$R^4$ and $R^5$ each represent independently for each occurrence hydrogen or $C_{1-6}$alkyl; or $R^4$ and $R^5$ taken together with the nitrogen atom to which they are attached form a 3-7 membered heterocyclic ring;

$R^6$ represents independently for each occurrence hydrogen or $C_{1-6}$alkyl; and m and p each represent independently for each occurrence 0, 1, or 2.

In certain embodiments, A is aryl or heteroaryl; each of which is optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is aryl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is phenyl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is phenyl optionally substituted with 1, 2, or 3 substituents independently selected from the group consisting of halogen and $C_{1-6}$haloalkyl. In certain embodiments, at least one substituent is attached at the meta-position of the phenyl ring.

In certain other embodiments, A is heterocycloalkyl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain embodiments, A is piperidine or pyrrolidine, each of which is optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy.

In certain embodiments, Y is —$N(R^2)(R^3)$. In certain embodiments, Y is —O-aralkyl optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —$N(R^4)(R^5)$, —CN, —$CO_2$—$C_{1-6}$alkyl, —C(O)—$C_{1-6}$alkyl, —C(O)$N(R^4)(R^5)$, —$S(O)_pC_{1-6}$alkyl, —$SO_2N(R^4)(R^5)$, and —$N(R^4)SO_2(C_{1-6}$alkyl). In certain other embodiments, Y is —O-aralkyl optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —$N(R^4)(R^5)$, —CN, —$CO_2$—$C_{1-6}$alkyl, and —C(O)—$C_{1-6}$alkyl. In certain other embodiments, Y is —O-benzyl optionally substituted with 1, 2, or 3 substituents independently selected from the group consisting of halogen, $C_{1-6}$alkyl, and $C_{1-6}$haloalkyl.

In certain embodiments, $R^1$ is hydrogen.

In certain embodiments, $R^2$ is —C(O)-aryl or —C(O)-aralkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, and $C_{1-6}$haloalkyl. In certain other embodiments, $R^2$ is —C(O)-aryl or —C(O)-aralkyl; each of which is substituted with 2 substituents independently selected from the group consisting of halogen, hydroxyl, $C_{1-6}$alkoxy, $C_{1-6}$haloalkoxy, $C_{1-6}$alkyl, and $C_{1-6}$haloalkyl, and said substituents are located at the ortho-positions of the aromatic ring. In certain other embodiments, $R^2$ is —C(O)-phenyl or —C(O)-benzyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, and $C_{1-6}$haloalkyl. In certain other embodiments, $R^2$ is —C(O)-phenyl or —C(O)-benzyl; each of which is optionally substituted with 1, 2, or 3 substituents independently selected from the group consisting of halogen, $C_{1-6}$alkyl, and $C_{1-6}$haloalkyl. In certain other embodiments, $R^2$ is represented by:

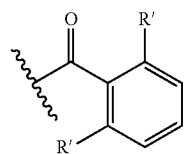

wherein each R' is independently halogen, hydroxyl, $C_{1-6}$alkoxy, $C_{1-6}$haloalkoxy, $C_{1-6}$alkyl, or $C_{1-6}$haloalkyl. In certain other embodiments, $R^2$ is represented by:

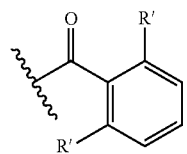

wherein each R' is independently halogen, $C_{1-6}$alkyl, or $C_{1-6}$haloalkyl.

In certain embodiments, $R^2$ is represented by:

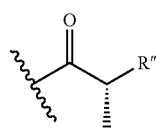

wherein R" is $C_{1-6}$alkyl, aryl, or heterocyclyl, each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N($R^4$)($R^5$), —CN, —$CO_2$—$C_{1-6}$alkyl, —C(O)—$C_{1-6}$alkyl, —C(O)N($R^4$)($R^5$), —S(O)$_p$$C_{1-6}$alkyl, —$SO_2$N($R^4$)($R^5$), and —N($R^4$)$SO_2$($C_{1-6}$alkyl). In certain embodiments, R" is phenyl optionally substituted with 1, 2, or 3 substituents independently selected from the group consisting of halogen, $C_{1-6}$alkyl, and $C_{1-6}$haloalkyl.

In certain embodiments, $R^3$ is hydrogen.

In certain embodiments, $R^7$ is hydrogen. In certain other embodiments $R^7$ is hydroxyl, $C_{1-6}$hydroxyalkyl, $C_{1-6}$alkyl, $C_{1-6}$haloalkyl, —$CO_2R^6$, $C_{1-6}$alkylene-$CO_2R^6$, $C_{1-4}$hydroxyalkylene-$CO_2R^6$, —N($R^4$)($R^5$), $C_{1-6}$alkylene-N($R^4$)($R^5$), $C_{1-6}$hydroxyalkylene-N($R^4$)($R^5$), —N($R^4$)C(O)$R^9$, $C_{1-6}$alkylene-N($R^4$)C(O)$R^9$, $C_{1-6}$alkylene-C(O)N($R^4$)($R^5$), —N($R^4$)$CO_2$—$C_{1-6}$alkyl, or —N($R^4$)C(O)$R^9$. In certain other embodiments, $R^7$ is $C_{1-6}$hydroxyalkyl, $C_{1-6}$alkyl, $C_{1-6}$alkylene-$CO_2R^6$, —N($R^4$)($R^5$), $C_{1-6}$alkylene-N($R^4$)($R^5$), or $C_{1-6}$alkylene-N($R^4$)C(O)$R^9$. In certain other embodiments, $R^7$ is $C_{1-3}$hydroxyalkyl, methyl, ethyl, or $C_{1-3}$alkylene-N(H)C(O)—$C_{1-4}$alkyl.

The definitions of variables in Formulae I through V above encompass multiple chemical groups. The application contemplates embodiments where, for example, i) the definition of a variable is a single chemical group selected from those chemical groups set forth above, ii) the definition is a collection of two or more of the chemical groups selected from those set forth above, and iii) the compound is defined by a combination of variables in which the variables are defined by (i) or (ii).

In certain other embodiments, the compound is one of the compounds listed in Tables 1-3 below or a pharmaceutically acceptable salt thereof.

TABLE 1

| No. | Y | Z |
|---|---|---|
| I-1 | | |
| I-2 | | |
| I-3 | | |

TABLE 1-continued
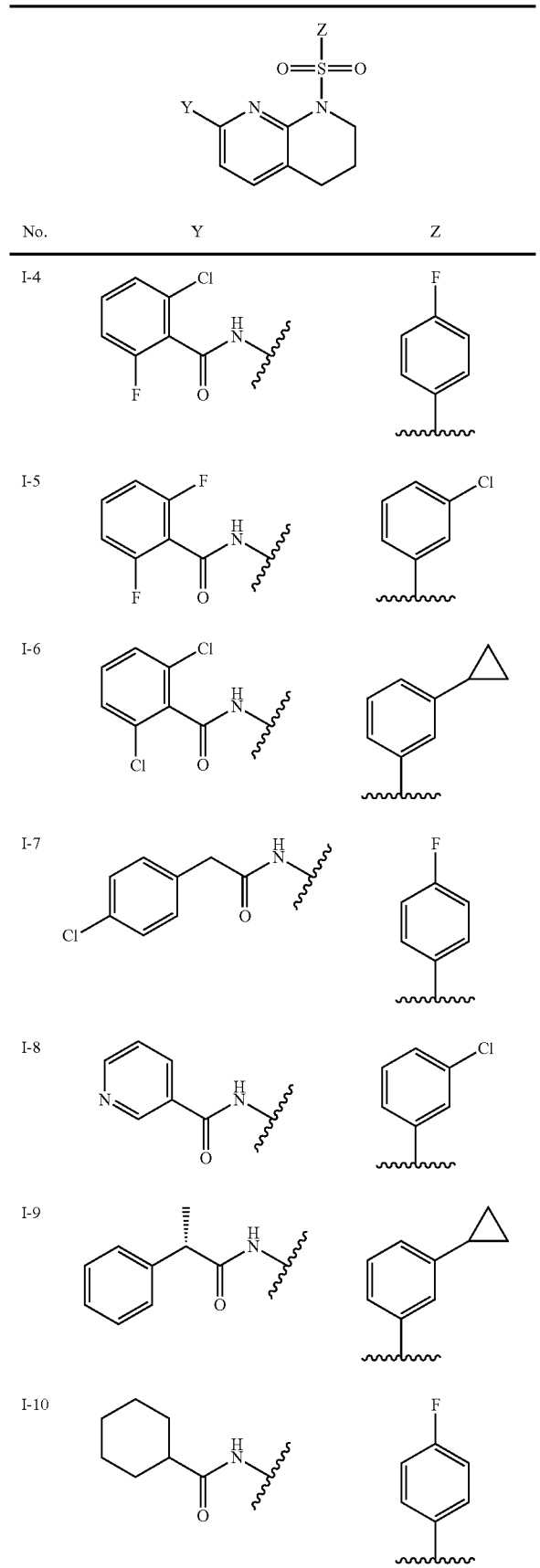
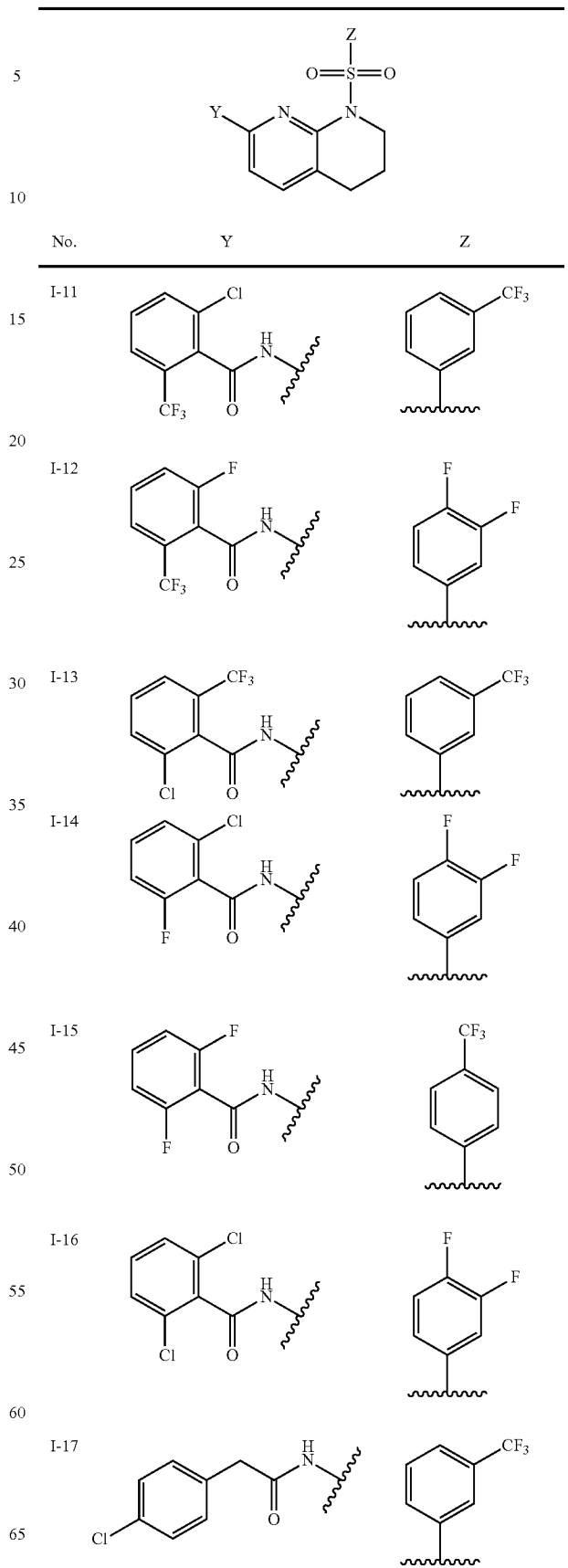

TABLE 1-continued

| No. | Y | Z |
|-----|---|---|
| I-18 | pyridin-3-ylcarbonylamino | 3,4-difluorophenyl |
| I-19 | (S)-2-phenylpropanoylamino | 3-(trifluoromethyl)phenyl |
| I-20 | cyclohexylcarbonylamino | 3,4-difluorophenyl |
| I-21 | 2-chloro-6-(trifluoromethyl)benzoylamino | 1-methyl-1H-pyrazol-4-yl |
| I-22 | 2-fluoro-6-(trifluoromethyl)benzoylamino | 1-methyl-1H-imidazol-4-yl |
| I-23 | 2-chloro-6-(trifluoromethyl)benzoylamino | 5-fluoropyridin-2-yl |
| I-24 | 2-chloro-6-fluorobenzoylamino | piperidin-1-yl |
| I-25 | 2,6-difluorobenzoylamino | 1-methylpyrrolidin-3-yl |
| I-26 | 2,6-dichlorobenzoylamino | 1-methyl-1H-pyrazol-4-yl |
| I-27 | 2-(4-chlorophenyl)acetylamino | 1-methyl-1H-imidazol-4-yl |
| I-28 | pyridin-3-ylcarbonylamino | 5-fluoropyridin-2-yl |
| I-29 | (S)-2-phenylpropanoylamino | piperidin-1-yl |
| I-30 | cyclohexylcarbonylamino | 1-methylpyrrolidin-3-yl |
| I-31 | isobutyrylamino | 3-methoxyphenyl |
| I-32 | isobutyrylamino | 4-fluorophenyl |

TABLE 1-continued

![Structure with Y-pyridine-N-SO2-Z core]

| No. | Y | Z |
|---|---|---|
| I-33 | isobutyramide (iPr-C(O)NH-) | 3-chlorophenyl |
| I-34 | (R)-2-methoxypropanamide (MeO-CH(Me)-C(O)NH-) | 3-methoxypyridin-5-yl |
| I-35 | (R)-2-methoxypropanamide (MeO-CH(Me)-C(O)NH-) | 3-chlorophenyl |
| I-36 | 2-(bicyclo[3.3.0]octan-2-yl)propanamide | 3-chlorophenyl |
| I-37 | 2-(bicyclo[3.3.0]octan-2-yl)propanamide | 3-methoxyphenyl |
| I-38 | 2-chloro-6-(trifluoromethyl)benzamide | 3-methoxyphenyl |
| I-39 | 2-fluoro-6-(trifluoromethyl)benzamide | octahydrocyclopenta[c]pyrrol-2-yl |
| I-40 | 2-chloro-6-(trifluoromethyl)benzamide | (2S,5R)-2-(hydroxymethyl)-5-methylpiperidin-1-yl |
| I-41 | 2,6-dichlorobenzyloxy | 4-fluorophenyl |
| I-42 | 2,6-dichlorobenzyloxy | 4-(trifluoromethyl)phenyl |
| I-43 | 2,6-dichlorobenzyloxy | 3,4-difluorophenyl |
| I-44 | benzyloxy | 1-methyl-1H-pyrazol-4-yl |
| I-45 | benzyloxy | octahydrocyclopenta[c]pyrrol-2-yl |

TABLE 2

| No. | Y | | Z |
|---|---|---|---|
| II-1 | 2-Cl, 6-CF3 benzamide | 5,6,7,8-tetrahydro-1,8-naphthyridin-2-yl (N1-attached to SO2) | 4-fluorophenyl |
| II-2 | 2-F, 6-CF3 benzamide | 5,6,7,8-tetrahydro-1,8-naphthyridin-2-yl | 3-CF3-phenyl |
| II-3 | 2,6-difluoro benzamide | 5,6,7,8-tetrahydro-1,8-naphthyridin-2-yl | 3,4-difluorophenyl |
| II-4 | 2-Cl, 6-F benzamide | 5,6,7,8-tetrahydro-1,8-naphthyridin-2-yl | 1-methyl-1H-pyrazol-4-yl |
| II-5 | 2,6-dichloro benzamide | 5,6,7,8-tetrahydro-1,8-naphthyridin-2-yl | 1-methylpiperidin-4-yl |
| II-6 | 2-Cl, 6-CF3 benzamide | 5,6,7,8-tetrahydro-1,8-naphthyridin-2-yl | 1-methylpyrrolidin-3-yl |
| II-7 | 2-Cl, 6-CF3 benzamide | 3-(hydroxymethyl)-5,6,7,8-tetrahydro-1,8-naphthyridin-2-yl | 4-fluorophenyl |

TABLE 2-continued

| No. | Y | | Z |
|---|---|---|---|
| II-8 | 2-F, 6-CF3 benzamide | 7-substituted-3-(hydroxymethyl)-1,2,3,4-tetrahydro-1,8-naphthyridine | 3-CF3 phenyl |
| II-9 | 2,6-difluorobenzamide | 7-substituted-3-(acetamidomethyl)-1,2,3,4-tetrahydro-1,8-naphthyridine | 3,4-difluorophenyl |
| II-10 | 2-Cl, 6-F benzamide | 7-substituted-3-(acetamidomethyl)-1,2,3,4-tetrahydro-1,8-naphthyridine | 1-methyl-1H-pyrazol-4-yl |
| II-11 | 2-Cl, 6-CF3 benzamide | 6-substituted-2,3-dihydro-1H-pyrido[2,3-b][1,4]oxazine | piperidin-1-yl |
| II-12 | 2-F, 6-CF3 benzamide | 6-substituted-2,3-dihydro-1H-pyrido[2,3-b][1,4]oxazine | 4-fluorophenyl |
| II-13 | 2,6-difluorobenzamide | 6-substituted-2,3-dihydro-1H-pyrido[2,3-b][1,4]oxazine | 3-CF3 phenyl |
| II-14 | 2-Cl, 6-F benzamide | 6-substituted-2,3-dihydro-1H-pyrido[2,3-b][1,4]oxazine | 3,4-difluorophenyl |

TABLE 2-continued
| No. | Y | | Z |
|---|---|---|---|
| II-15 | 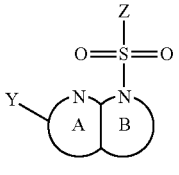 | 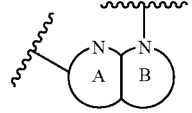 | 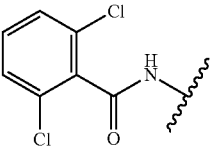 |
| II-16 | 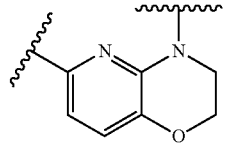 [SMILES: *c1ccc2c(n1)N(*)CCO2] | 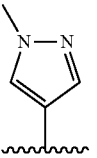 | 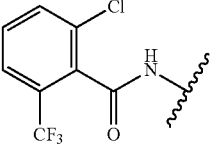 |
| II-17 | 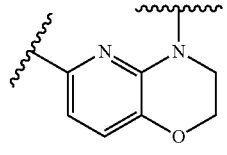 [SMILES: *c1ccc2c(n1)N(*)CCO2] | 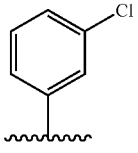 | 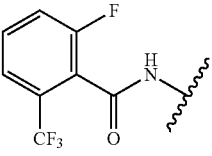 |
| II-18 | 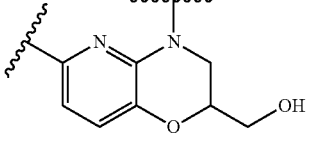 | 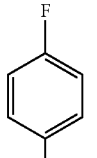 | 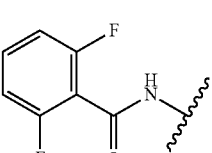 |
| II-19 | 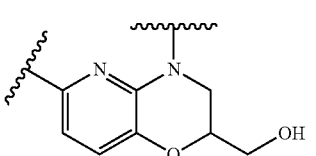 | 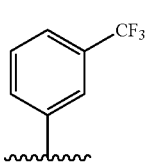 [SMILES: *c1cccc(C(F)(F)F)c1] | 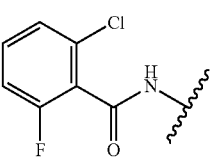 [SMILES: *NC(=O)c1c(F)cccc1Cl] |
| II-20 | 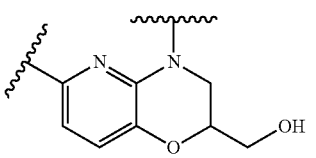 [SMILES: *c1ccc2c(n1)N(*)CC(CO)O2] | 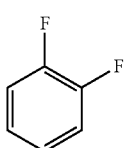 | 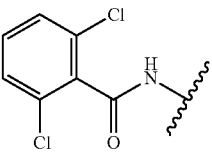 |
| II-21 | 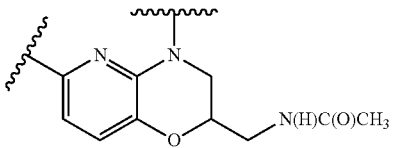 | 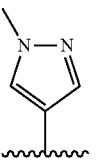 | 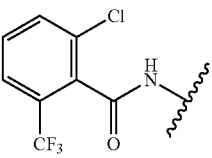 |

TABLE 2-continued

| No. | Y | (central bicycle) | Z |
|---|---|---|---|
| II-22 | 2-F, 6-CF₃ benzamide | pyrido-oxazine with CH₂N(H)C(O)CH₃ | 4-F-phenyl |
| II-23 | 2,6-diF benzamide | methyl-pyrido-oxazine | 3-CF₃-phenyl |
| II-24 | 2-Cl, 6-F benzamide | methyl-pyrido-oxazine | 3,4-diF-phenyl |
| II-25 | 2,6-diCl benzamide | methyl-pyrido-oxazine | 1-methyl-1H-pyrazol-4-yl |
| II-26 | 2-Cl, 6-CF₃ benzamide | 4-oxo-tetrahydro-1,8-naphthyridine | piperidinyl |
| II-27 | 2-F, 6-CF₃ benzamide | 4-oxo-tetrahydro-1,8-naphthyridine | 4-F-phenyl |
| II-28 | 2,6-diF benzamide | 4-oxo-tetrahydro-1,8-naphthyridine | 3-CF₃-phenyl |

TABLE 2-continued
| No. | Y | | Z |
|---|---|---|---|
| II-29 | 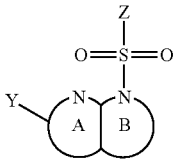 | 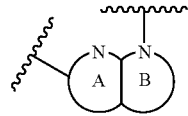 | 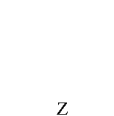 |
| II-30 | 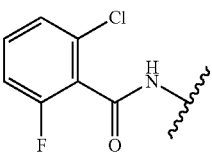 | 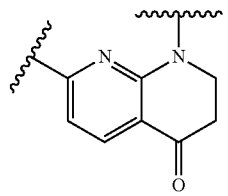 [SMILES: *c1ccc2c(n1)N(*)CCC2=O] | 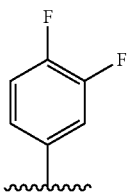 [SMILES: *c1ccc(F)c(F)c1] |
| II-31 | 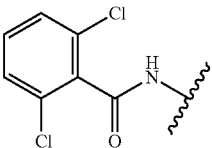 [SMILES: *NC(=O)c1c(Cl)cccc1Cl] | 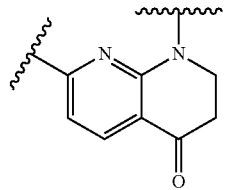 [SMILES: *c1ccc2c(n1)N(*)CCC2=O] | 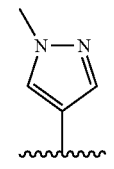 [SMILES: *c1cnn(C)c1] |
| II-32 | 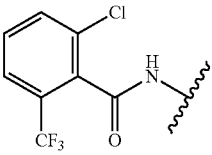 [SMILES: *NC(=O)c1c(Cl)cccc1C(F)(F)F] | 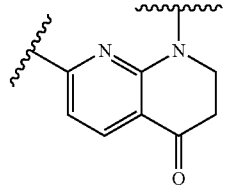 [SMILES: *c1ccc2c(n1)N(*)CCC2=O] | 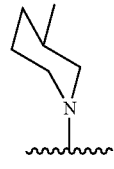 [SMILES: *N1CCCC(C)C1] |
| II-33 | 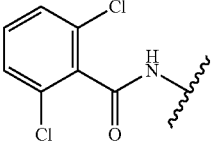 [SMILES: *NC(=O)c1c(Cl)cccc1Cl] | 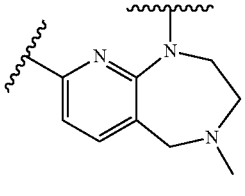 [SMILES: *c1ccc2c(n1)N(*)CCN(C)C2] | 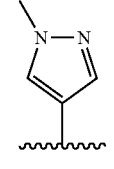 [SMILES: *c1cnn(C)c1] |
| II-34 | 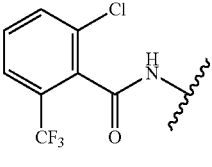 [SMILES: *NC(=O)c1c(Cl)cccc1C(F)(F)F] | 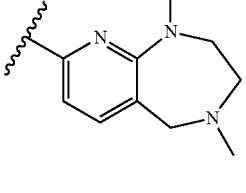 | 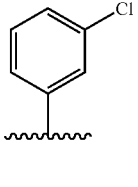 [SMILES: *c1cccc(Cl)c1] |

TABLE 2-continued
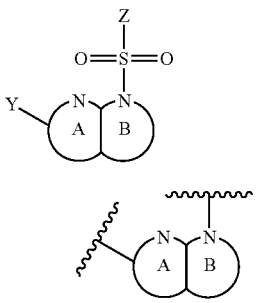
| No. | Y | | Z |
|---|---|---|---|
| II-35 | 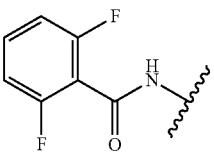 [SMILES: *NC(=O)c1c(F)cccc1F] | 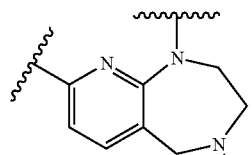 | 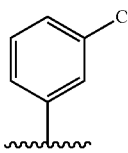 |
TABLE 3
| No. | Compound |
|---|---|
| III-1 | 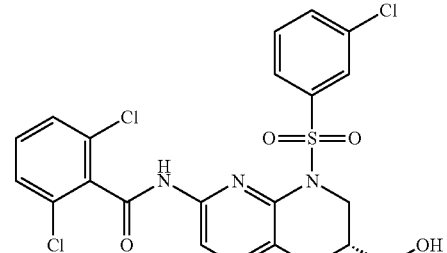 |
| III-2 | 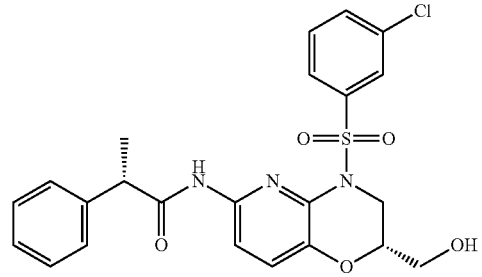 [SMILES: C[C@H](C(=O)Nc1ccc2c(n1)N(S(=O)(=O)c1cccc(Cl)c1)C[C@H](CO)O2)c1ccccc1] |
| III-3 | 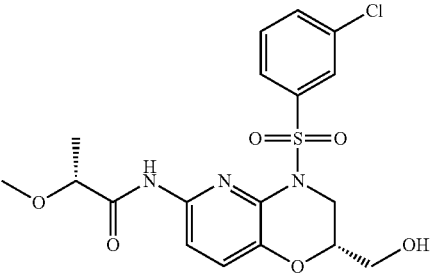 [SMILES: CO[C@H](C)C(=O)Nc1ccc2c(n1)N(S(=O)(=O)c1cccc(Cl)c1)C[C@H](CO)O2] |
TABLE 3-continued
| No. | Compound |
|---|---|
| III-4 | 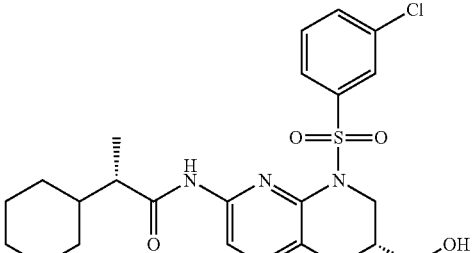 |
| III-5 | 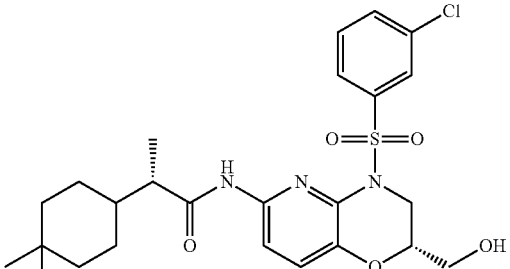 |
| III-6 |  |

TABLE 3-continued

| No. | Compound |
|---|---|
| III-7 | |
| III-8 | |
| III-9 | |
| III-10 | |
| III-11 | |
| III-12 | |
| III-13 | |
| III-14 | |
| III-15 | |
| III-16 | |

TABLE 3-continued

| No. | Compound |
|---|---|
| III-17 | |
| III-18 | |
| III-19 | |
| III-20 | |
| III-21 | |
| III-22 | |
| III-23 | |
| III-24 | |
| III-25 | |
| III-26 | |

TABLE 3-continued

| No. | Compound |
|---|---|
| III-27 | (structure) |
| III-28 | (structure) |
| III-29 | (structure) |
| III-30 | (structure) |
| III-31 | (structure) |
| III-32 | (structure) |
| III-33 | (structure) |
| III-34 | (structure) |
| III-35 | (structure) |

TABLE 3-continued

| No. | Compound |
|---|---|
| III-36 | (structure) |
| III-37 | (structure) |
| III-38 | (structure) |
| III-39 | (structure) |
| III-40 | (structure) |
| III-41 | (structure) |
| III-42 | (structure) |
| III-43 | (structure) |
| III-44 | (structure) |
| III-45 | (structure) |

TABLE 3-continued

| No. | Compound |
|---|---|
| III-46 | (structure) |
| III-47 | (structure) |
| III-48 | (structure) |
| III-49 | (structure) |
| III-50 | (structure) |
| III-51 | (structure) |
| III-52 | (structure) |

Methods for preparing compounds described herein are illustrated in the following synthetic schemes. The schemes are given for the purpose of illustrating the invention, and are not intended to limit the scope or spirit of the invention. Starting materials shown in the schemes can be obtained from commercial sources or be prepared based on procedures described in the literature.

The synthetic route illustrated in Scheme 1 is a general method for preparing amide-substituted 5,6,7,8-tetrahydro[1,8]naphthyridine compounds. Reaction of diaminopyridine A with a mixture of an acid and substituted dimethylaminoacrolein B provides amino-1,8-naphthyridine C. Alternatively, amino-1,8-naphthyridine C can be prepared by reacting diaminopyridine A with 1,3-dicarbonyl compound B1 (See, for example, Reichart et al. in *Tet. Lett.* 1977, 24, 2087-90; Eva, E. et al. *J. Het. Chem.* 1976, 13, 841-844, and Bernstein et al. *J. Amer. Chem. Soc.* 1947, 69, 1151-1158) or substituted vinamidinium salt B2 (See, for example, Norma et al. in *Synthesis* 2001, 9, 1351-1355).

Reaction of amino-1,8-naphthyridine C with an acylating reagent (e.g., an acid chloride) provides amido-1,8-naphthyridine D. Reduction of amido-1,8-naphthyridine D by hydrogenation provides amido-tetrahydro-1,8-naphthyridine E, which can be reacted with a sulphonyl chloride or sulfamoyl chloride to provide the final sulfonamide-tetrahydro-1,8-naphthyridine F.

The reaction procedures in Scheme 1 are contemplated to be amenable to preparing a wide variety of amide-substituted tetrahydro[1,8]naphthyridine compounds having different substituents at the R through $R^V$ positions. For example, numerous substituted 2,6-diaminopyridines are known in the literature and/or are commercially available. Furthermore, if a functional group that is part of the R—$R^V$ group would not be amenable to a reaction condition described in Scheme 1, it is contemplated that the functional group can first be protected using standard protecting group chemistry and strategies, and then the protecting group is removed after completing the desired synthetic transformation. See, for example, Greene, T. W.; Wuts, P. G. M. Protective Groups in Organic Synthesis, 2nd ed.; Wiley: New York, 1991, for further description of protecting chemistry and strategies. In certain other embodiments, a functional group in substituent R through $R^V$ in tetrahydro[1,8]naphthyridine F can converted to another functional group using standard functional group manipulation procedures known in the art. See, for example, "Comprehensive Organic Synthesis" (B. M. Trost & I. Fleming, eds., 1991-1992)

carbamate (Bhagwanth et al. in J. Org Chem. 2009, 74, 4634-4637) followed by deprotection; (3) Pd-mediated addition of hexamethyldisilazide (Stefko et al. in J. Org. Chem. 2011, 76, 6619-6635), and (4) Pd-mediated addition of diphenylmethanimine followed by deprotection with acid (Grasa et al. in J. Org. Chem. 2001, 66, 7729-7737). Reaction of amine F with an acid chloride provides amide G. It is understood that an acid ($R^I CO_2 H$) and amide-coupling reagent can be used in lieu of the acid chloride in the step used to produce amide G.

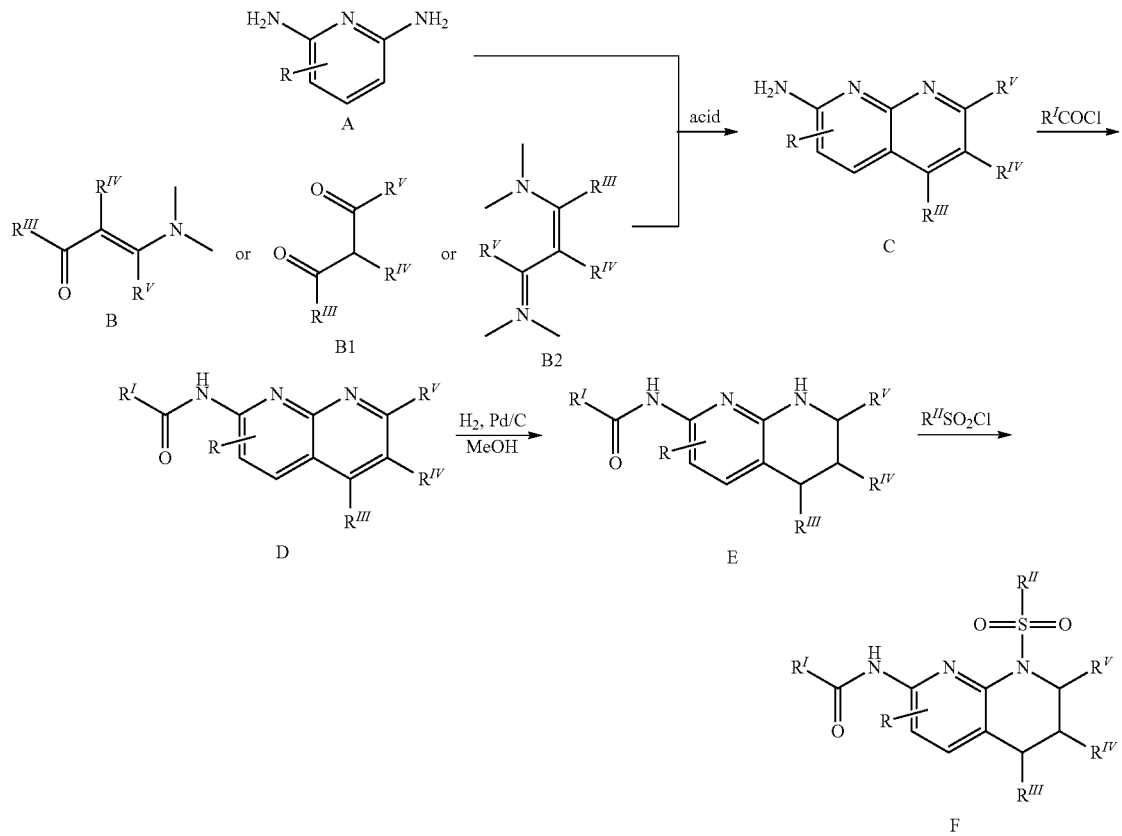

R and $R^{III}$ to $R^V$ may be, for example. hydrogen or a substituent, such as methyl; and $R^I$ and $R^{II}$ may be, for example, a cyclic group, such as phenyl.

Scheme 2 illustrates a general method for preparing amido-dihydro-2H-pyrido[3,2-b][1,4]oxazines. Alkylation of nitro-hydroxy-pyridine A with a 2-haloester provides pyridinyl ether B. Conversion of nitro-hydroxy-pyridine A to pyridinyl ether B can also be carried out by Mitsunobu alkylation of a 2-hydroxyester. Next, reductive cyclization of pyridinyl ether B affords 4H-pyrido[3,2-b][1,4]oxazine-3-one C. Reduction of the amide using, for example, a hydride (e.g., a borane or lithium aluminum hydride) provides dihydro-2H-pyrido[3,2-b][1,4]oxazine D. Treatment of oxazine D with a sulphonyl chloride or sulfamoyl chloride provides sulfonamido-bromo-dihydro-2H-pyrido[3,2-b][1,4]oxazine E.

Bromo-dihydro-2H-pyrido[3,2-b][1,4]oxazine E can be converted to amino-dihydro-2H-pyrido[3,2-b][1,4]oxazine F using procedures known in the art, such as (1) Ullmann $CuSO_4$ mediated addition of ammonia (Hauser et al. in J. Org. Chem. 1950, 15, 1224-1232); (2) Pd-mediated addition of a

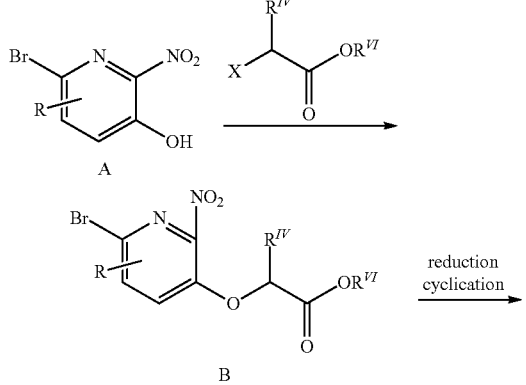

-continued

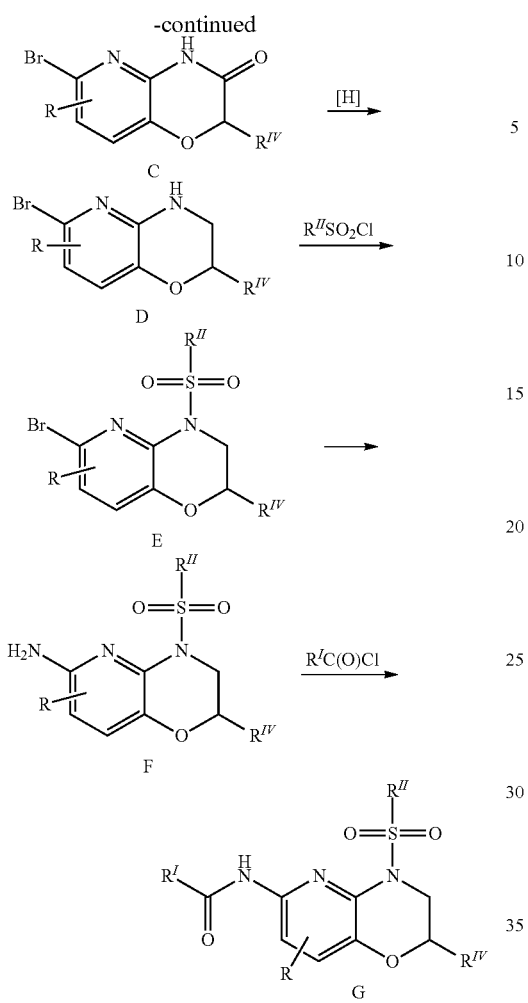

R may be, for example, hydrogen or a substituent, such as methyl;
$R^I$ abd $R^{II}$ may be, for example, a cyclic group, such as phenyl;
$R^{IV}$ and $R^{VI}$ may be, for example, a substituent, such as methyl; and
X is a leaving group, such as halogen.

Reacting halo-amino-pyridine A with a Negishi reagent (formed from a 2-((tert-butoxycarbonyl)amino)-3-iodopropanoate) provides amino acid B. Then, intramolecular cyclization of amino acid B promoted by heat or a base provides dihydro-1,8-naphthyridin-2(1H)-one C. Reacting dihydro-1,8-naphthyridin-2(1H)-one C with benzylchloroformate affords bis-carbamate D. Selective reduction of the amide group in bis-carbamate D using borane or lithium aluminum hydride provides tetrahydro-1,8-naphthyridine E. Reaction of tetrahydro-1,8-naphthyridine E with a sulphonyl chloride or sulfamoyl chloride provides sulfonamide F. Next, the benzylcarbamate protecting group is removed from sulfonamide F to provide an amino-tetrahydro-1,8-naphthyridine (not shown) that can be subjected to amide coupling conditions using a carboxylic acid and an amide coupling agent to provide amido-tetrahydro-1,8-naphthyridine G. The remaining Boc protecting group on amido-tetrahydro-1,8-naphthyridine G can be removed by treatment with acid to provide amino-tetrahydro-1,8-naphthyridine H. It is understood that the amino group on amino-tetrahydro-1,5-naphthyridine H can be converted to other functional groups (e.g., by reaction with an alkylating agent(s), aldehyde (reductive alkylations), acyl halide, sulphonyl chloride, isocyanate, and the like) to afford the compound I.

SCHEME 3.

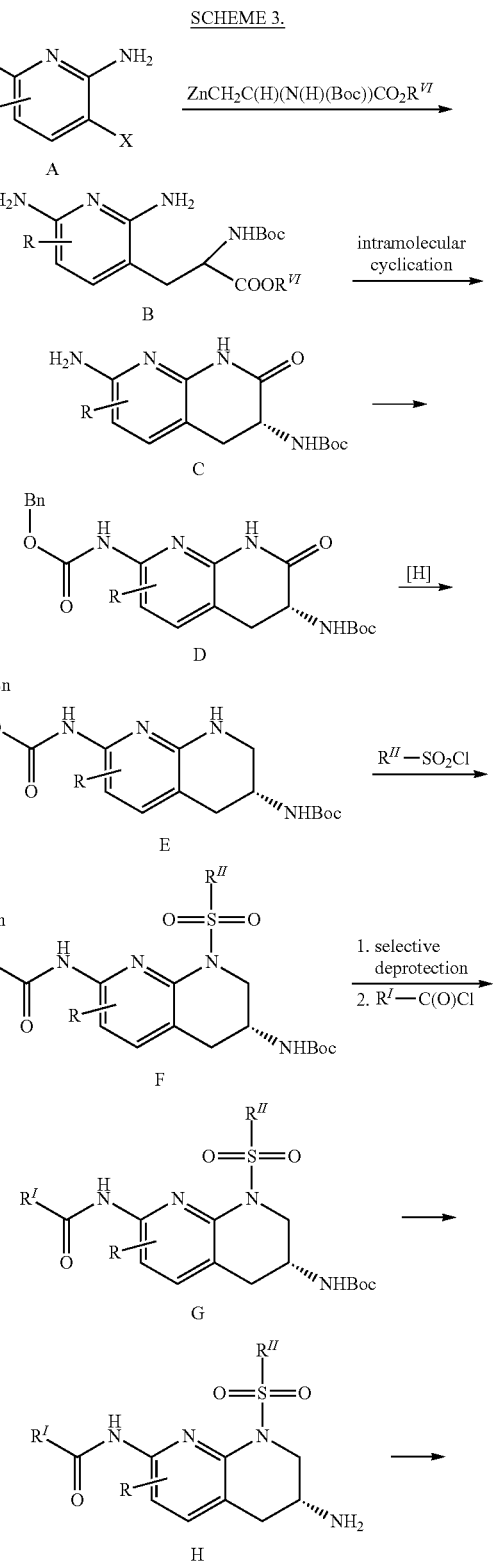

-continued

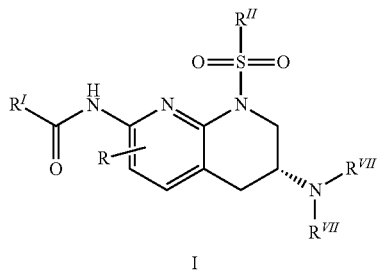

I

R may be, for example, hydrogen or a substituent, such as methyl;
$R^I$ and $R^{II}$ may be, for example, a cyclic group, such as phenyl;
$R^{VI}$-$R^{VIII}$ are substituents, such as methyl; and
X is, for example, halogen.

Scheme 4 illustrates an alternative general method for preparing amido-dihydro-2H-pyrido[3,2-b][1,4]oxazines. Alkylation of hydroxy-pyridine A with 2-halo-alkanone B affords pyridinyl ether C. Exhaustive reduction (e.g., using Raney Nickel) with in situ intramolecular cyclization provides bromo-dihydro-2H-pyrido[3,2-b]oxazine D. Reaction of oxazine D with a sulphonyl chloride or sulfamoyl chloride provides bromo-sulfonamido-dihydro-2H-pyrido[3,2-b]oxazine E. Bromo-sulfonamido-dihydro-2H-pyrido[3,2-b]oxazine E can be converted to amine F using procedures known in the art, such as (1) Ullmann $CuSO_4$ mediated addition of ammonia (Hauser et al. in *J. Org. Chem.* 1950, 15, 1224-1232); (2) Pd-mediated addition of a carbamate (Bhagwanth et al. in *J. Org Chem.* 2009, 74, 4634-4637) followed by deprotection; (3) Pd-mediated addition of hexamethyldisilazide (Stefko et al. in *J. Org. Chem.* 2011, 76, 6619-6635), and (4) Pd-mediated addition of diphenylmethanimine followed by deprotection with acid (Grasa et al. in *J. Org. Chem.* 2001, 66, 7729-7737). Reaction of amine F with an acid chloride provides amide G. It is understood that an acid ($R^{I}CO_2H$) and amide-coupling reagent can be used in lieu of the acid chloride in the step used to produce amide G.

SCHEME 4.

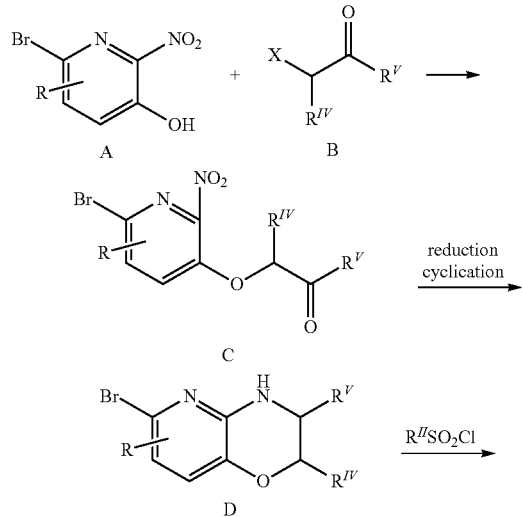

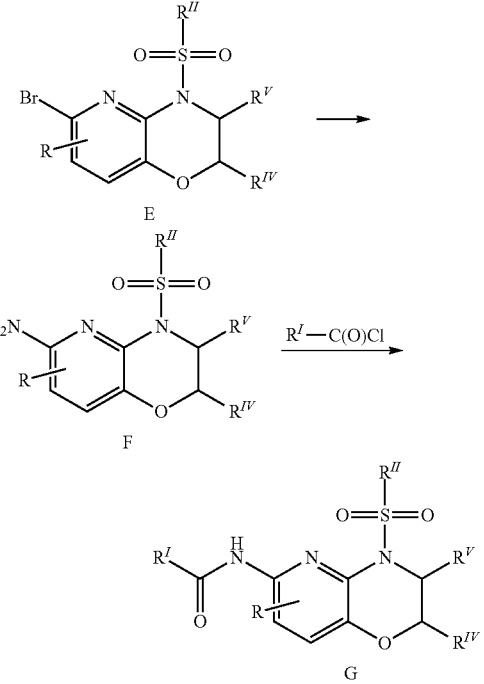

$R^I$ and $R^{II}$ may be, for example, a cyclic group, such as phenyl; and
R, $R^{IV}$, and $R^V$ may be, for example, hydrogen or a substituent, such as methyl.

Scheme 5 illustrates another general procedure for preparing amido-tetrahydro-1,8-naphthyridines with a hydroxyl or alkoxyl group at the 6-position. Reacting halo-amino-pyridine A with a Negishi reagent (formed from a 2-alkoxy-3-iodopropanoate) provides pyridinyl ester B. Then, intramolecular cyclization of pyridinyl ester B promoted by heat or a base provides dihydro-1,8-naphthyridin-2(1H)-one C. Reacting dihydro-1,8-naphthyridin-2(1H)-one C with benzylchloroformate affords bis-carbamate D. Selective reduction of the amide group in bis-carbamate D using borane or lithium aluminum hydride provides tetrahydro-1,8-naphthyridine E. Reaction of tetrahydro-1,8-naphthyridine E with a sulphonyl chloride or sulfamoyl chloride provides sulfonamide F. Next, the benzylcarbamate protecting group is removed from sulfonamide F to provide an amino-tetrahydro-1,8-naphthyridine (not shown) that can be subjected to amide coupling conditions using a carboxylic acid and an amide coupling agent to provide amido-tetrahydro-1,8-naphthyridine G. To the extent a hydroxy-tetrahydro-1,8-naphthyridine is desired, variable $R^{IV}$ may be a trialkylsilyl group, which may be removed by reacting amido-tetrahydro-1,8-naphthyridine G with a silyl group deprotecting agent, such as tetrabutylammonium fluoride.

SCHEME 5.

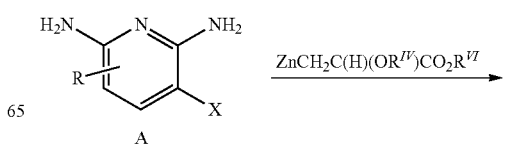

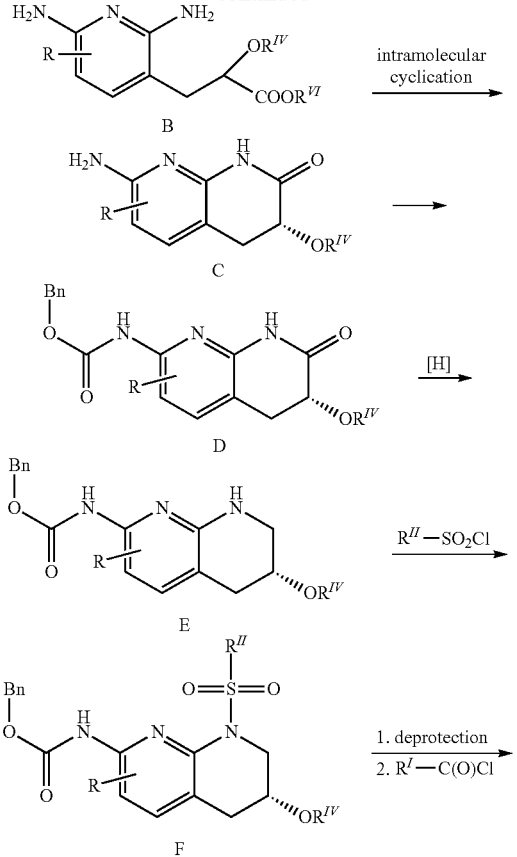

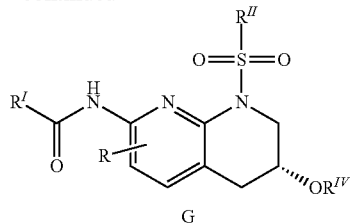

R may be, for example, hydrogen or a substituent, such as methyl;
$R^I$ and $R^{II}$ may be, for example, a cyclic group, such as phenyl;
$R^{IV}$ is a hydroxyl protecting group or alkyl;
$R^{VI}$ is a substituent, such as methyl; and
X may be, for example, halogen.

Scheme 6 illustrates another general procedure for preparing aralkyloxy-tetrahydro-1,8-naphthyridine compounds. Reaction of aralkyloxy-aminopyridine A with a mixture of an acid and substituted dimethylaminoacrolein B provides 1,8-naphthyridine C. Alternatively, 1,8-naphthyridine C can be prepared by reacting aralkyloxy-aminopyridine with 1,3-dicarbonyl compound B1 (See, for example, Reichart et al. in *Tet. Lett.* 1977, 24, 2087-90; Eva, E. et al. *J. Het. Chem.* 1976, 13, 841-844, and Bernstein et al. *J. Amer. Chem. Soc.* 1947, 69, 1151-1158) or substituted vinamidinium salt B2 (See, for example, Norma et al. in *Synthesis* 2001, 9, 1351-1355). Reduction of 1,8-naphthyridine C by hydrogenation (e.g., using $H_2$ with Pd/C in methanol) provides tetrahydro-1,8-naphthyridine D, which can be reacted with a sulphonyl chloride or sulfamoyl chloride to provide the final aralkyloxy-sulfonamide-tetrahydro-1,8-naphthyridine E.

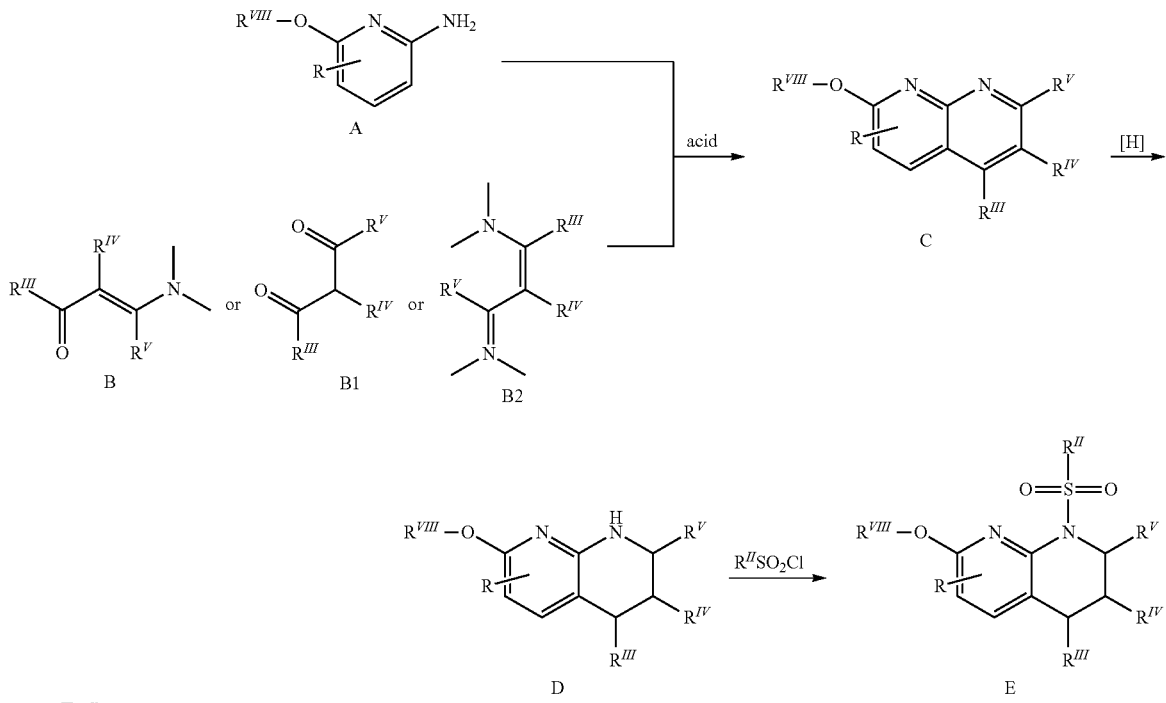

R and $R^{III}$-$R^V$ may be, for example, hydrogen or a substituent, such as methyl;
$R^{II}$ may be, for example, a cyclic group, such as phenyl; and
$R^{VIII}$ is aralkyl, such as benzyl.

Scheme 7 illustrates an alternative general procedure for preparing aralkyloxy-dihydro-2H-pyrido[3,2-b][1,4]oxazines. Ullman coupling of an alcohol ($R^{VIII}$—OH) with bromide A provides aralkyloxy-dihydro-2H-pyrido[3,2-b][1,4] oxazine B.

SCHEME 7.

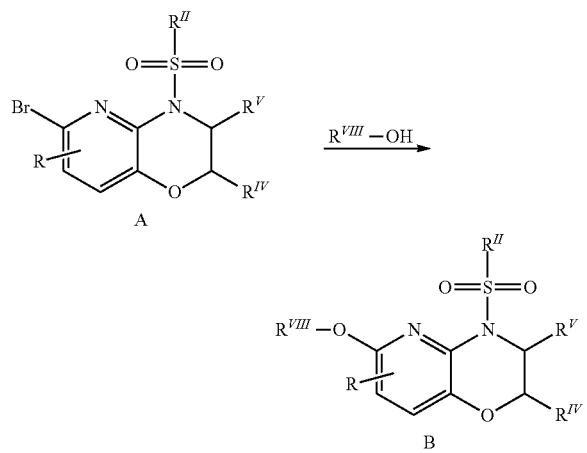

R, $R^{IV}$, and $R^{V}$ may be, for example, hydrogen or a substituent, such as methyl;
$R^{II}$ may be, for example, a cyclic group, such as phenyl; and
$R^{VIII}$ is aralkyl, such as benzyl.

II. Therapeutic Applications of Tetrahydro[1,8]naphthyridine and Related Compounds It is contemplated that the tetrahydro[1,8]naphthyridine and related compounds described herein, such as a compound of Formula I, II, III, IV, or V, provide therapeutic benefits to subjects suffering from a cancer, bacterial infection, fungal infection, or immune deficiency disorder. Accordingly, one aspect of the invention provides a method of treating a disorder selected from the group consisting of cancer, bacterial infection, fungal infection, and immune deficiency disorder. The method comprises administering a therapeutically effective amount of a tetrahydro[1,8]naphthyridine or related compound described herein, such as a compound of Formula I, II, III, IV, or V, to a subject in need thereof to ameliorate a symptom of the disorder, wherein Formula I, II, III, IV, and V are as described above. In certain embodiments, the particular compound of Formula I, II, III, IV, or V is a compound defined by one of the embodiments described above.

In certain embodiments, the disorder is cancer. In certain embodiments, the cancer is a solid tumor or leukemia. In certain other embodiments, the cancer is colon cancer, pancreatic cancer, breast cancer, ovarian cancer, prostate cancer, squamous cell carcinoma, basal cell carcinoma, adenocarcinoma, sweat gland carcinoma, sebaceous gland carcinoma, lung cancer, leukemia, bladder cancer, stomach cancer, cervical cancer, testicular cancer, skin cancer, rectal cancer, thyroid cancer, kidney cancer, uterus cancer, espophagus cancer, liver cancer, an acoustic neuroma, oligodendroglioma, meningioma, neuroblastoma, or retinoblastoma. In certain other embodiments, the cancer is small cell lung cancer, non-small cell lung cancer, melanoma, cancer of the central nervous system tissue, brain cancer, Hodgkin's lymphoma, non-Hodgkin's lymphoma, cutaneous T-Cell lymphoma, cutaneous B-Cell lymphoma, or diffuse large B-Cell lymphoma. In certain other embodiments, the cancer is breast cancer, colon cancer, small-cell lung cancer, non-small cell lung cancer, prostate cancer, renal cancer, ovarian cancer, leukemia, melanoma, or cancer of the central nervous system tissue. In certain other embodiments, the cancer is colon cancer, small-cell lung cancer, non-small cell lung cancer, renal cancer, ovarian cancer, renal cancer, or melanoma.

Additional exemplary cancers include fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, epithelial carcinoma, glioma, astrocytoma, medulloblastoma, and hemangioblastoma.

In certain embodiments, the caner is a neuroblastoma, meningioma, hemangiopericytoma, multiple brain metastase, glioblastoma multiforms, glioblastoma, brain stem glioma, poor prognosis malignant brain tumor, malignant glioma, anaplastic astrocytoma, anaplastic oligodendroglioma, neuroendocrine tumor, rectal adeno carcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, metastatic melanoma, localized melanoma, malignant mesothelioma, malignant pleural effusion mesothelioma syndrome, peritoneal carcinoma, papillary serous carcinoma, gynecologic sarcoma, soft tissue sarcoma, scelroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waidenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, or leiomyoma.

In certain embodiments, the disorder is a bacterial infection. The bacterial infection can be characterized according to classifications known in the art. For example, in certain embodiments, the bacterial infection is a gram-positive bacterial infection, such as a gram-positive cocci bacterial infection or a gram-positive bacilli bacterial infection. In other embodiments, the bacterial infection is a gram-negative bacterial infection, such as a gram-negative cocci bacterial infection or a gram-negative bacilli bacterial infection. The bacterial infection can also be characterized according to whether it is caused by anaerobic or aerobic bacteria. Accordingly, in certain embodiments, the bacterial infection is an anaerobic bacterial infection. In certain other embodiments, the bacterial infection is an aerobic bacterial infection.

A variety of bacteria are contemplated to be susceptible to the tetrahydro[1,8]naphthyridine compounds. Representative bacteria include Staphylococci species, e.g., *S. aureus; Enterococci* species, e.g., *E. faecalis* and *E. faecium; Streptococci* species, e.g., *S. pyogenes* and *S. pneumoniae; Escherichia* species, e.g., *E. coli,* including enterotoxigenic, enteropathogenic, enteroinvasive, enterohemorrhagic and enteroaggregative *E. coli* strains; *Haemophilus* species, e.g., *H. influenza;* and *Moraxella* species, e.g., *M. catarrhalis.*

Other examples include *Mycobacteria* species, e.g., *M. tuberculosis, M. avian-intracellulare, M. kansasii, M. bovis, M. africanum, M. genavense, M. leprae, M. xenopi, M. simiae, M. scrofulaceum, M. malmoense, M. celatum, M. abscessus, M. chelonae, M. szulgai, M. gordonae, M. haemophilum, M. fortuni* and *M. marinum; Corynebacteria* species, e.g., *C. diphtheriae; Vibrio* species, e.g., *V. cholerae; Campylobacter* species, e.g., *C. jejuni; Helicobacter* species, e.g., *H. pylori; Pseudomonas* species, e.g., *P. aeruginosa; Legionella* species, e.g., *L. pneumophila; Treponema* species, e.g., *T. pallidum; Borrelia* species, e.g., *B. burgdorferi; Listeria* species, e.g., *L. monocytogenes; Bacillus* species, e.g., *B. cereus; Bordatella* species, e.g., *B. pertussis; Clostridium* species, e.g., *C. perfringens, C. tetani, C. difficile* and *C. botulinum; Neisseria* species, e.g., *N. meningitidis* and *N. gonorrhoeae; Chlamydia* species, e.g., *C. psittaci, C. pneumoniae* and *C. trachomatis; Rickettsia* species, e.g., *R. rickettsii* and *R. prowazekii; Shigella* species, e.g., *S. sonnei; Salmonella* species, e.g., *S. typhimurium; Yersinia* species, e.g., *Y. enterocolitica* and *Y. pseudotuberculosis; Klebsiella* species, e.g., *K. pneumoniae; Mycoplasma* species, e.g., *M. pneumoniae*; and *Trypanosoma brucei*. In certain embodiments, the compounds described herein are used to treat a subject suffering from a bacterial infection selected from the group consisting of *S. aureus, E. faecalis, E. faecium, S. pyogenes, S. pneumonia*, and *P. aeruginosa*.

The antibacterial activity of compounds described herein may be evaluated using assays known in the art, such as the microbroth dilution minimum inhibition concentration (MIC) assay, as further described in National Committee for Clinical Laboratory Standards. Performance Standards for Antimicrobial Susceptibility Testing; Fourteenth Informational Supplement. NCCLS document M100-S14 {ISBN 1-56238-516-X}. This assay may be used to determine the minimum concentration of a compound necessary to prevent visible bacterial growth in a solution. In general, the drug to be tested is serially diluted into wells, and aliquots of liquid bacterial culture are added. This mixture is incubated under appropriate conditions, and then tested for growth of the bacteria. Compounds with low or no antibiotic activity (a high MIC) will allow growth at high concentrations of compound, while compounds with high antibiotic activity will allow bacterial growth only at lower concentrations (a low MIC).

The assay uses stock bacterial culture conditions appropriate for the chosen strain of bacteria. Stock cultures from the permanent stock culture collection can be stored as frozen suspensions at −70° C. Cultures may be suspended in 10% skim milk (BD) prior to snap freezing in dry ice/ethanol and then placed in a −70° C. freezer. Cultures may be maintained on Tryptic Soy Agar containing 5% Sheep Blood at room temperature (20° C.), and each culture may be recovered from frozen form and transferred an additional time before MIC testing. Fresh plates are inoculated the day before testing, incubated overnight, and checked to confirm purity and identity.

The identity and purity of the cultures recovered from the stock culture can be confirmed to rule out the possibility of contamination. The identity of the strains may be confirmed by standard microbiological methods (See, e.g., Murray et al., Manual of Clinical Microbiology, Eighth Edition. ASM Press {ISBN 1-55581-255-4}). In general, cultures are streaked onto appropriate agar plates for visualization of purity, expected colony morphology, and hemolytic patterns. Gram stains can also be utilized. The identities are confirmed using a MicroScan WalkAway 40 SI Instrument (Dade Behring, West Sacramento, Calif.). This device utilizes an automated incubator, reader, and computer to assess for identification purposes the biochemical reactions carried out by each organism. The MicroScan WalkAway can also be used to determine a preliminary MIC, which may be confirmed using the method described below.

Frozen stock cultures may be used as the initial source of organisms for performing microbroth dilution minimum inhibition concentration (MIC) testing. Stock cultures are passed on their standard growth medium for at least 1 growth cycle (18-24 hours) prior to their use. Most bacteria may be prepared directly from agar plates in 10 mL aliquots of the appropriate broth medium. Bacterial cultures are adjusted to the opacity of a 0.5 McFarland Standard (optical density value of 0.28-0.33 on a Perkin-Elmer Lambda EZ150 Spectrophotometer, Wellesley, Mass., set at a wavelength of 600 nm). The adjusted cultures are then diluted 400 fold (0.25 mL inoculum+100 mL broth) in growth media to produce a starting suspension of approximately $5 \times 10^5$ colony forming units (CFU)/mL. Most bacterial strains may be tested in cation adjusted Mueller Hinton Broth (CAMHB).

Test compounds ("drugs") are solubilized in a solvent suitable for the assay, such as DMSO. Drug stock solutions may be prepared on the day of testing. Microbroth dilution stock plates may be prepared in two dilution series, 64 to 0.06 µg drug/mL and 0.25 to 0.00025 µg drug/mL. For the high concentration series, 200 µL of stock solution (2 mg/mL) is added to duplicate rows of a 96-well microtiter plate. This is used as the first well in the dilution series. Serial two-fold decremental dilutions are made using a BioMek FX robot (Beckman Coulter Inc., Fullerton, Calif.) with 10 of the remaining 11 wells, each of which will contain 100 µL of the appropriate solvent/diluent. Row 12 contains solvent/diluent only and serves as the control. For the first well of the low concentration series, 200 µL of an 8 µg/mL stock are added to duplicate rows of a 96-well plate. Serial two-fold dilutions are made as described above.

Daughter 96-well plates may be spotted (3.2 µL/well) from the stock plates listed above using the BioMek FX robot and used immediately or frozen at −70° C. until use. Aerobic organisms are inoculated (100 µL volumes) into the thawed plates using the BioMek FX robot. The inoculated plates are be placed in stacks and covered with an empty plate. These plates are then incubated for 16 to 24 hours in ambient atmosphere according to CLSI guidelines (National Committee for Clinical Laboratory Standards, Methods for Dilution, Antimicrobial Tests for Bacteria that Grow Aerobically; Approved Standard-Sixth Edition. NCCLS document M7-A6 {ISBN 1-56238-486-4}).

After inoculation and incubation, the degree of bacterial growth can be estimated visually with the aid of a Test Reading Mirror (Dynex Technologies 220 16) in a darkened room with a single light shining directly through the top of the microbroth tray. The MIC is the lowest concentration of drug that prevents macroscopically visible growth under the conditions of the test.

In certain embodiments, the disorder is a fungal infection. Exemplary fungi that may be treated include, for example, *Acremonium, Absidia* (e.g., *Absidia corymbifera*), *Alternaria, Aspergillus* (e.g., *Aspergillus clavatus, Aspergillus flavus, Aspergillus fumigatus, Aspergillus nidulans, Aspergillus niger, Aspergillus terreus*, and *Aspergillus versicolor*), *Aureobasidium, Basidiobolus, Blastomyces* (e.g., *Blastomyces dermatitidis*), *Candida* (e.g., *Candida albicans, Candida glabrata, Candida guilliermondii, Candida kefyr, Candida krusei, Candida lusitaniae, Candida parapsilosis, Candida pseudotropicalis, Candida stellatoidea, Candida tropicalis, Candida utilis, Candida lipolytica, Candida famata* and *Candida rugosa*), *Cephalosporium, Chaetomium, Chrysospo-* rium, *Cladosporium* (e.g., *Cladosporium carrionii* and *Cladosporium trichloides*), *Coccidioides* (e.g., *Coccidioides immitis*), *Conidiobolus, Coprinus, Corynespora, Cryptococcus* (e.g., *Cryptococcus neoformans*), *Curvularia, Cunninghamella* (e.g., *Cunninghamella elegans*), *Exophiala* (e.g., *Exophiala dermatitidis* and *Exophiala spinifera*), *Epidermophyton* (e.g., *Epidermophyton floccosum*), *Fonsecaea* (e.g., *Fonsecaea pedrosoi*), *Fusarium* (e.g., *Fusarium solani*), *Geotrichum* (e.g., *Geotrichum candiddum* and *Geotrichum clavatum*), *Hendersonula, Histoplasma, Leptosphaeria, Loboa, Madurella, Malassezia* (e.g., *Malassezia furfur*), *Microsporum* (e.g., *Microsporum canis* and *Microsporum gypseum*), *Mycocentrospora, Mucor, Neotestudina, Paecilomyces, Paracoccidioides* (e.g., *Paracoccidioides brasiliensis*), *Penicillium* (e.g., *Penicillium marneffei*), *Phialophora, Pneumocystis* (e.g., *Pneumocystis carinii*), *Pseudallescheria* (e.g., *Pseudallescheria boydii*), *Rhinosporidium, Rhizomucor, Rhizopus* (e.g., *Rhizopus microsporus* var. *rhizopodiformis* and *Rhizopus oryzae*), *Saccharomyces* (e.g., *Saccharomyces cerevisiae*), *Scopulariopsis, Sporothrix* (e.g., *Sporothrix schenckii*), *Trichophyton* (e.g., *Trichophyton mentagrophytes* and *Trichophyton rubrum*), *Trichosporon* (e.g., *Trichosporon asahii, Trichosporon beigelii* and *Trichosporon cutaneum*), and *Wangiella*.

In certain embodiments, the disorder is an immune deficiency disorder. Exemplary immune deficiency disorders include, for example, a human immunodeficiency viral infection, a patient with a deficient immune system due to chemotherapy, or a patient recovering from surgery who has a deficient immune system.

In certain embodiments, the subject is a human.

Another aspect of the invention provides for the use of a compound described herein (such as a compound of Formula I, II, III, IV, or V) in the manufacture of a medicament. In certain embodiments, the medicament is for treating a disorder described herein, such as cancer.

Another aspect of the invention provides for the use of a compound described herein (such as a compound of Formula I, II, III, IV, or V) for treating a medical disorder, such a medical disorder described herein (e.g., cancer).

Further, it is contemplated that tetrahydro[1,8]naphthyridine and related compounds described herein, such as a compound of Formula I, II, III, IV, or V, can promote the activity of RORγ. Accordingly, another aspect of the invention provides a method of promoting the activity of RORγ. The method comprises exposing a RORγ to an effective amount of a tetrahydro[1,8]naphthyridine or related compound described herein, such as a compound of Formula I, II, III, IV, or V, to promote RORγ activity, wherein Formula I, II, III, IV, and V are as described above. In certain embodiments, the particular compound of Formula I, II, III, IV, or V is the compound defined by one of the embodiments described above. Promoting the activity of RORγ means to increase the activity of RORγ. In certain embodiments, exposing a RORγ to an effective amount of a tetrahydro[1,8]naphthyridine or related compound described herein (such as a compound of Formula I, II, III, IV, or V) results in an increase in RORγ activity of at least 5%, 10%, 20%, or 50% relative to the activity of RORγ under substantially the same conditions but without the presence of the tetrahydro[1,8]naphthyridine or related compound.

Further, it is contemplated that tetrahydro[1,8]naphthyridine and related compounds described herein, such as a compound of Formula I, II, III, IV, or V, can increase the amount of interleukin-17 (IL-17) in a subject. IL-17 is a cytokine that affects numerous biological functions. Accordingly, another aspect of the invention provides a method of increasing the amount of IL-17 in a subject. The method comprises administering to a subject an effective amount of a tetrahydro[1,8]naphthyridine or related compound described herein, such as a compound of Formula I, II, III, IV, or V, to increase the amount of IL-17 in the subject, wherein Formula I, II, III, IV, and V are as described above. In certain embodiments, the particular compound of Formula I, II, III, IV, or V is the compound defined by one of the embodiments described above.

In certain embodiments, the subject is a human. In certain embodiments, administering the compound increases the amount of IL-17 produced by Th-17 cells in the subject. A change in the amount of IL-17 produced by, for example, Th-17 cells can be measured using procedures described in the literature, such as an ELISA assay or intracellular staining assay.

Further, it is contemplated that tetrahydro[1,8]naphthyridine and related compounds described herein, such as a compound of Formula I, II, III, IV, or V, may increase the synthesis of IL-17 in a subject. Accordingly, another aspect of the invention provides a method of increasing the synthesis of IL-17 in a subject. The method comprises administering to a subject an effective amount of a compound described herein, e.g., a compound of Formula I, II, III, IV, or V, to increase the synthesis of IL-17 in the subject, wherein Formula I, II, III, IV, and V are as described above. In certain embodiments, the particular compound of Formula I, II, III, IV, or V is a compound defined by one of the embodiments described above.

The description above describes multiple embodiments providing definitions for variables used herein. The application specifically contemplates all combinations of such variables, e.g., particular combinations of the definitions set forth for variables A and X.

III. Combination Therapy

Another aspect of the invention provides for combination therapy. Tetrahydro[1,8]naphthyridine and related compounds (e.g., a compound of Formula I, II, III, IV, or V) or their pharmaceutically acceptable salts may be used in combination with additional therapeutic agents to treat medical disorders, such as a cancer, bacterial infection, fungal infection, and immune deficiency disorder.

Exemplary therapeutic agents that may be used as part of a combination therapy in treating cancer, include, for example, mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, lisuride, oxymetholone, tamoxifen, progesterone, mepitiostane, epitiostanol, formestane, interferon-alpha, interferon-2 alpha, interferon-beta, interferon-gamma, colony stimulating factor-1, colony stimulating factor-2, denileukin diftitox, interleukin-2, and leutinizing hormone releasing factor.

Exemplary therapeutic agents that may be used as part of a combination therapy in treating a bacterial infection, include, for example, amoxicillin, azithromycin, cefazolin, ceftriaxone, cefuroxime, cephalexin, ciprofloxacin, clindamycin, doxycycline, levofloxacin, linezolid, metronidazole, moxifloxacin, and penicillin.

Exemplary therapeutic agents that may be used as part of a combination therapy in treating a fungal infection, include, for example, 2-phenylphenol; 8-hydroxyquinoline sulphate; acibenzolar-S-methyl; aldimorph; amidoflumet; ampropyl-fos; ampropylfos-potassium; andoprim; anilazine; azaconazole; azoxystrobin; benalaxyl; benodanil; benomyl; benthiavalicarb-isopropyl; benzamacril; benzamacril-isobutyl; bilanafos; binapacryl; biphenyl; bitertanol; blasticidin-S; bromuconazole; butylamine; calcium polysulphide; capsimycin; captafol; captan; carbendazim; carboxin; carpropamid; carvone; chinomethionat; chlobenthiazone; chlorfenazole; chloroneb; chlorothalonil; chlozolinate; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulphamide; hexaconazole; hymexazole; imazalil; imibenconazole; iminoctadine triacetate; iminoctadine tris(albesil); iodocarb; ipconazole; iprobenfos; iprodione; iprovalicarb; irumamycin; isoprothiolane; isovaledione; kasugamycin; kresoxim-methyl; oxyfenthiin; paclobutrazole; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolenitrine; tetraconazole; thiabendazole; thicyofen; thifluzamide; thiophanate-methyl; thiram; tioxymid; tricyclazole; tridemorph; trifloxystrobin; triflumizole; triforine; tritiraconazole; uniconazole; validamycin A; vinclozolin; zineb; ziram; and zoxamide.

The amount of tetrahydro[1,8]naphthyridine or related compound (e.g., a compound of Formula I, II, III, IV, or V) and additional therapeutic agent and the relative timing of administration may be selected in order to achieve a desired combined therapeutic effect. For example, when administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. Further, for example, a tetrahydro[1,8] naphthyridine or related compound (e.g., a compound of any one of Formula I, II, III, IV, or V) may be administered during a time when the additional therapeutic agent(s) exerts its prophylactic or therapeutic effect, or vice versa.

The doses and dosage regimen of the active ingredients used in the combination therapy may be determined by an attending clinician. In certain embodiments, the tetrahydro[1,8]naphthyridine or related compound (e.g., a compound of any one of Formula I, II, III, IV, or V) and the additional therapeutic agent(s) are administered in doses commonly employed when such agents are used as monotherapy for treating the disorder. In other embodiments, the tetrahydro[1,8]naphthyridine or related compound (e.g., a compound of any one of Formula I, II, III, IV, or V) and the additional therapeutic agent(s) are administered in doses lower than the doses commonly employed when such agents are used as monotherapy for treating the disorder. In certain embodiments, the tetrahydro[1,8]naphthyridine or related compound (e.g., a compound of any one of Formula I, II, III, IV, or V) and the additional therapeutic agent(s) are present in the same composition, which is suitable for oral administration.

In certain embodiments, the tetrahydro[1,8]naphthyridine or related compound (e.g., a compound of any one of Formula I, II, III, IV, or V) and the additional therapeutic agent(s) may act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

Another aspect of this invention is a kit comprising a therapeutically effective amount of the tetrahydro[1,8]naphthyridine or related compound (e.g., a compound of any one of Formula I, II, III, IV, or V), a pharmaceutically acceptable carrier, vehicle or diluent, and optionally at least one additional therapeutic agent listed above.

IV. Pharmaceutical Compositions and Dosing Considerations

As indicated above, the invention provides pharmaceutical compositions, which comprise a therapeutically-effective amount of one or more of the compounds described above, formulated together with one or more pharmaceutically acceptable carriers (additives) and/or diluents. The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

If desired, the effective daily dose of the active compound may be administered as two, three, four, five, six or more sub-doses administered separately at appropriate intervals throughout the day, optionally, in unit dosage forms. Preferred dosing is one administration per day.

The invention further provides a unit dosage form (such as a tablet or capsule) comprising a tetrahydro[1,8]naphthyridine or related compound described herein (such as a compound of any one of Formulae I-V or a specific compound described herein, such as in Tables 1-3) in a therapeutically effective amount for the treatment of an immune or inflammatory disorder, such as one of the particular immune disorders or inflammatory disorders described herein.

EXAMPLES

The invention now being generally described, will be more readily understood by reference to the following examples, which are included merely for purposes of illustration of certain aspects and embodiments of the present invention, and are not intended to limit the invention.

Example 1

Synthesis of 2,6-Difluoro-N-(8-(4-fluorobenzenesulfonyl)-5,6,7,8-tetrahydro[1,8]naphthyridin-2-yl)benzamide (1)

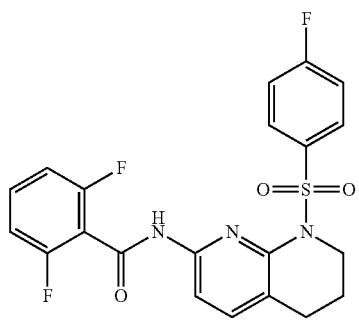 [SMILES: O=C(Nc1ccc2c(n1)N(S(=O)(=O)c1ccc(F)cc1)CCC2)c1c(F)cccc1F]

The title compound was prepared according to the procedures described below.

Part I—Synthesis of [1,8]-Naphthyridin-2-ylamine

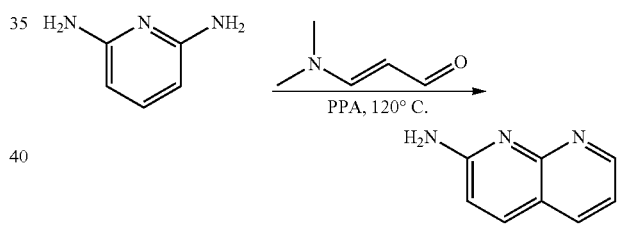

Pyridine-2,6-diamine (0.30 g, 2.8 mmol), 3-dimethylaminoacrolein (90%, 0.30 g, 2.8 mmol), and polyphosphoric acid (PPA) (2.7 mL) were combined and the reaction mixture was heated to 120° C. for 10 hours. Then, the reaction mixture was poured on ice water and neutralized with solid sodium carbonate. The resulting aqueous mixture was extracted three times with ethyl acetate and the combined organic extracts were washed with brine, concentrated, and purified by column chromatography (EtOAc/hexanes) to give [1,8]-naphthyridin-2-ylamine Yield 85 mg (21%). LCMS (ESI): calc. $C_8H_7N_3=145$; obs. M+H=146.

Part II—Synthesis of 2,6-Difluoro-N-[1,8]naphthyridin-2-ylbenzamide

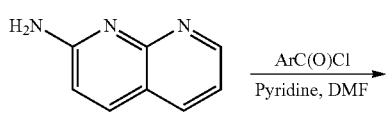

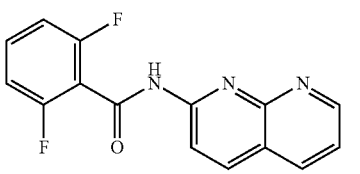

[1,8]-Naphthyridin-2-ylamine (85 mg, 0.59 mmol) was dissolved in dichloromethane (2 mL) and pyridine (0.10 mL, 1.2 mmol). 2,6-Difluorobenzoyl chloride (0.068 mL, 0.76 mmol) was then added and the reaction mixture was stirred at room temperature for 30 minutes. Next, the reaction mixture was diluted with ethyl acetate and washed with water followed by brine. The resulting organic solution was purified by column chromatography (EtOAc/hexanes) to give 2,6-difluoro-N-[1,8]naphthyridin-2-ylbenzamide. Yield 35 mg (21%). LCMS (ESI): calc. $C_{15}H_9F_2N_3O$=285; obs. M+H=286.

Part III—Synthesis of 2,6-Difluoro-N-(5,6,7,8-tetrahydro[1,8]naphthyridin-2-yl)benzamide

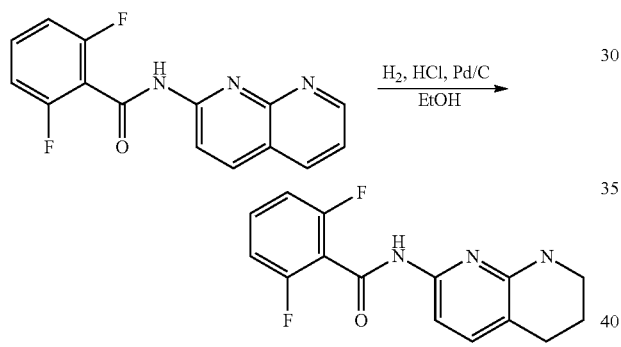

2,6-Difluoro-N-[1,8]naphthyridin-2-ylbenzamide (35 mg, 0.12 mmol) and 10% Pd/C (15 mg) were suspended in ethanol (5 mL). Concentrated HCl (0.02 mL, 0.24 mmol) was then added and the reaction mixture was stirred under hydrogen (1 atmosphere) for three hours. Next, the reaction mixture was filtered through Celite and concentrated to give 2,6-difluoro-N-(5,6,7,8-tetrahydro[1,8]naphthyridin-2-yl)benzamide. Yield 33 mg (95%). LCMS (ESI): calc. $C_{15}H_{13}F_2N_3O$=289; obs. M+H=290.

Part IV—Synthesis of 2,6-Difluoro-N-(8-(4-fluorobenzenesulfonyl)-5,6,7,8-tetrahydro[1,8]naphthyridin-2-yl)benzamide

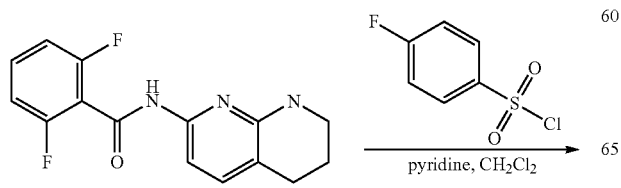

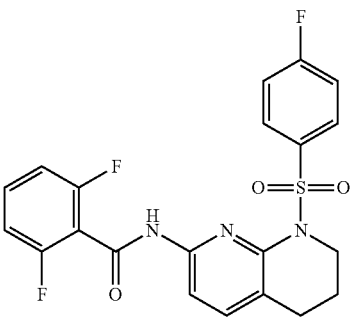

2,6-Difluoro-N-(5,6,7,8-tetrahydro[1,8]naphthyridin-2-yl)benzamide (30 mg, 0.10 mmol) was dissolved in dichloromethane (0.3 mL) and pyridine (0.025 mL, 0.31 mmol). 4-Fluorobenzenesulfonyl chloride (23 mg, 0.12 mmol) was then added and the reaction mixture was stirred at room temperature for 12 hours. Next, the reaction mixture was washed with 1M HCl(aq), sat'd NaHCO$_3$(aq), and brine. The resulting organic solution was concentrated, dissolved in DMSO, and purified by HPLC to give 2,6-difluoro-N-(8-(4-fluorobenzenesulfonyl)-5,6,7,8-tetrahydro[1,8]naphthyridin-2-yl)benzamide. $^1$H NMR 250 MHz CDCl$_3$ δ 8.13 (bs, 1H), 8.03 (dd, J=7.9, 4.3 Hz, 2H), 7.83 (d, J=7.9 Hz, 1H), 7.48 (p, J=6.5 Hz, 1H), 7.38 (d, J=7.9 Hz, 1H), 7.15 (t, J=7.9 Hz, 2H), 7.06 (t, J=7.8 Hz, 2H), 4.07 (dd, J=5.8, 4.3 Hz, 2H), 2.76 (t, J=6.5 Hz, 2H), 2.06 (p, J=5.8 Hz, 2H). LCMS (ESI): calc. $C_{21}H_{16}F_3N_3O_3S$=447; obs. M+H=448.

Example 2

Synthesis of 2,6-Dichloro-N-[4-(toluene-3-sulfonyl)-3,4-dihydro-2H-pyrido[3,2-b][1,4]oxazin-6-yl]-benzamide (2)

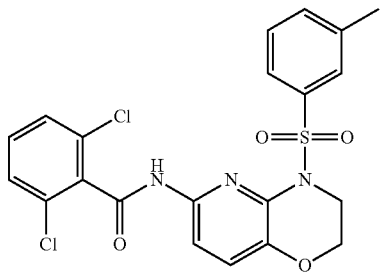 [SMILES: Cc1cccc(S(=O)(=O)N2CCOc3ccc(NC(=O)c4c(Cl)cccc4Cl)nc32)c1]

Part I—Synthesis of (6-Bromo-2-nitropyridin-3-yloxy)acetic acid methyl ester

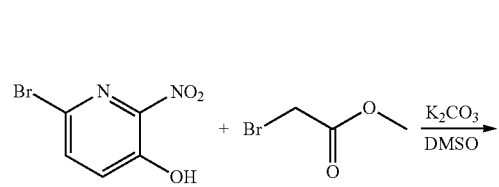

-continued

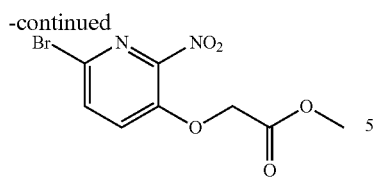

6-Bromo-2-nitropyridin-3-ol (10.8 g, 49.1 mmol) was dissolved in dimethylsulfoxide (DMSO) (30 mL). Potassium carbonate (13.6 g, 98.6 mmol) and bromoacetic acid methyl ester (7.0 mL, 74 mmol) were added and the reaction mixture was stirred at 60° C. for two hours. Then, the reaction mixture was cooled to room temperature and neutralized with 1N HCl(aq). The aqueous solution was extracted twice with ethyl acetate, and the combined organic extracts were washed with brine. The product was purified by column chromatography (SiO$_2$, EtOAc/hexanes) to afford (6-bromo-2-nitropyridin-3-yloxy)acetic acid methyl ester. Yield 10.9 g (37.5 mmol, 76%). LCMS (ESI): calc. C$_8$H$_7$BrN$_2$O$_5$=290, 292; obs. Low ionization.

Part II—Synthesis of (2-Amino-6-bromopyridin-3-yloxy)acetic acid methyl ester

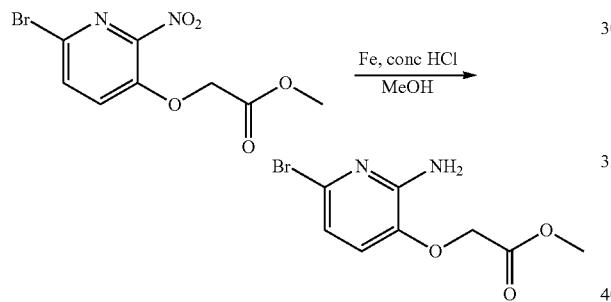

(6-Bromo-2-nitropyridin-3-yloxy)acetic acid methyl ester (10.9 g, 37.5 mmol) was dissolved in methanol (90 mL). Concentrated HCl (10 mL) was then added followed by iron (6.4 g, 110 mmol). The reaction mixture was stirred at 60° C. for 1 hour. Then, the reaction mixture was cooled to room temperature and neutralized with solid sodium bicarbonate. The insoluble iron salts were removed by centrifugation. Silica gel was then added to the supernatant and the solvents were removed under reduced pressure. The resulting crude material was purified by column chromatography (SiO$_2$, EtOAc/hexanes) to give (2-amino-6-bromopyridin-3-yloxy)acetic acid methyl ester. Yield 4.0 g (15 mmol, 40%). LCMS (ESI): calc. C$_8$H$_9$BrN$_2$O$_3$=260, 262; obs. M+H=261, 263.

Part III—Synthesis of 6-Bromo-4H-pyrido[3,2-b][1,4]oxazine-3-one

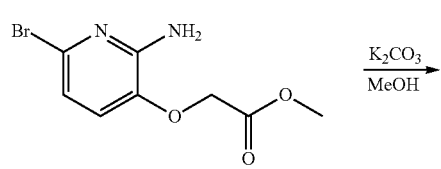

-continued

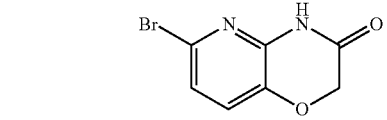

(2-Amino-6-bromopyridin-3-yloxy)acetic acid methyl ester (4.0 g, 15 mmol) was dissolved in MeOH (40 mL). K$_2$CO$_3$ (3.0 g, 22 mmol) was added and the reaction was stirred at 70° C. for 1 hour. Then, the solvent was removed under reduced pressure and the resulting slurry was suspended in dichloromethane (DCM) and washed with H$_2$O and then brine. The organic layer was dried (Na$_2$SO$_4$) and the product was precipitated from DCM/Et$_2$O to give 6-bromo-4H-pyrido[3,2-b][1,4]oxazin-3-one. Yield 1.9 g (8.3 mmol, 55%). LCMS (ESI): calc. C$_7$H$_5$BrN$_2$O$_2$=228, 230; obs. M+H=229, 231.

Part IV—Synthesis of 6-Bromo-3,4-dihydro-2H-pyrido[3,2-b][1,4]oxazine

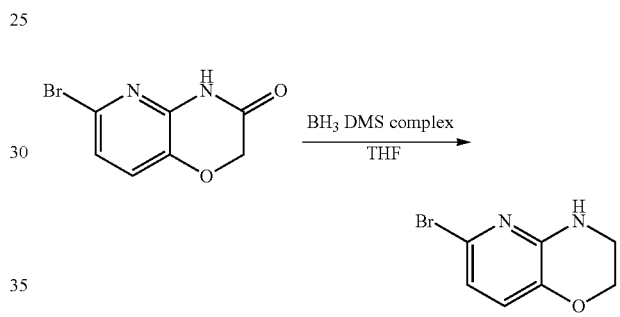

6-Bromo-4H-pyrido[3,2-b][1,4]oxazin-3-one (1.35 g, 5.89 mmol) was dissolved in THF (40 mL). Boranedimethylsulphide complex (2.0 M in THF, 5.89 mL, 11.79 mmol) was added and the resulting mixture heated to 70° C. under nitrogen for 15 minutes. Next, the reaction mixture was cooled to room temperature, quenched with methanol (~5 mL), and then dried under vacuum to obtain a white solid. The crude material was dissolved in dichloromethane and washed with H$_2$O. The aqueous phase was discarded and the organic phase was dried under vacuum to give 6-bromo-3,4-dihydro-2H-pyrido[3,2-b][1,4]oxazine. Yield: 1.1 g (87%). LCMS (ESI): calc. C$_7$H$_7$BrN$_2$O=214, 216; obs. M+H=215, 217.

Part V—Synthesis of 6-Bromo-4-(toluene-3-sulfonyl)-3,4-dihydro-2H-pyrido[3,2-b][1,4]oxazine

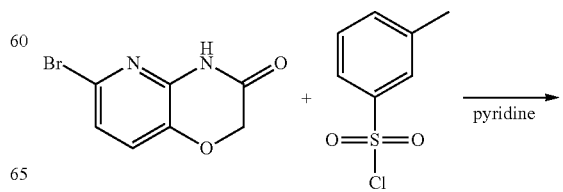

83
-continued

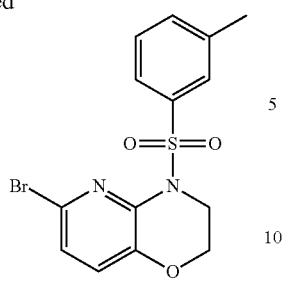

6-Bromo-3,4-dihydro-2H-pyrido[3,2-b][1,4]oxazine (1.0 g, 4.65 mmol) and m-tolylsulfonyl chloride were dissolved in pyridine (10 mL). The resulting mixture was stirred at 80° C. for one hour. An additional portion of m-tolylsulfonyl chloride (0.98 g, 5.12 mmol) was added and the reaction mixture was stirred at 80° C. for 16 hours. Next, excess solvent was removed under vacuum, and the resulting oil was triturated with water to obtain a tan solid, which was collected by vacuum filtration and washed with water and diethyl ether to give 6-bromo-4-(toluene-3-sulfonyl)-3,4-dihydro-2H-pyrido[3,2-b][1,4]oxazine. Yield 1.3 g (76%). LCMS (ESI): calc. $C_{14}H_{13}BrN_2O_3S$=368, 370; obs. M+H=369, 371.

Part VI—Synthesis of 4-(Toluene-3-sulfonyl)-3,4-dihydro-2H-pyrido[3,2-b][1,4]oxazin-6-ylamine

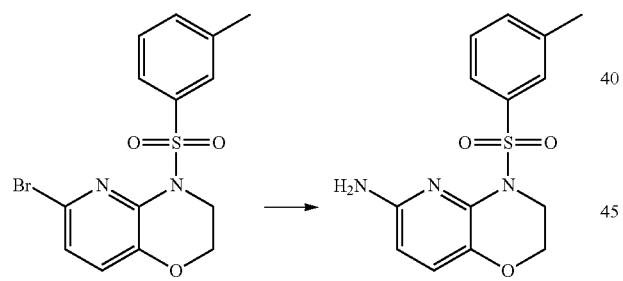

6-Bromo-4-(toluene-3-sulfonyl)-3,4-dihydro-2H-pyrido[3,2-b][1,4]oxazine (300 mg, 0.81 mmol) was dissolved in p-dioxane (10 mL), followed by benzophenone imine (409 µL, 2.44 mmol), sodium tert-butoxide (207 mg, 2.15 mmol), XantPhos (70 mg, 0.12 mmol), and finally $Pd_2(dba)_3$ (74 mg, 0.08 mmol). The resulting mixture was heated to 100° C. for 2.5 hours. Then, the reaction mixture was concentrated under vacuum and partitioned in a mixture of ethyl acetate and water. The aqueous phase was discarded, and the organic phase was concentrated and purified by flash chromatography (12 g silica column, 0-60% EtOAc/Hexane) to give 4-(toluene-3-sulfonyl)-3,4-dihydro-2H-pyrido[3,2-b][1,4]oxazin-6-ylamine Yield 80 mg (32%). LCMS (ESI): calc. $C_{14}H_{15}N_3O_3S$=305; obs. M+H=306.

84
Part VII—Synthesis of 2,6-Dichloro-N-[4-(toluene-3-sulfonyl)-3,4-dihydro-2H-pyrido[3,2-b][1,4]oxazin-6-yl]-benzamide

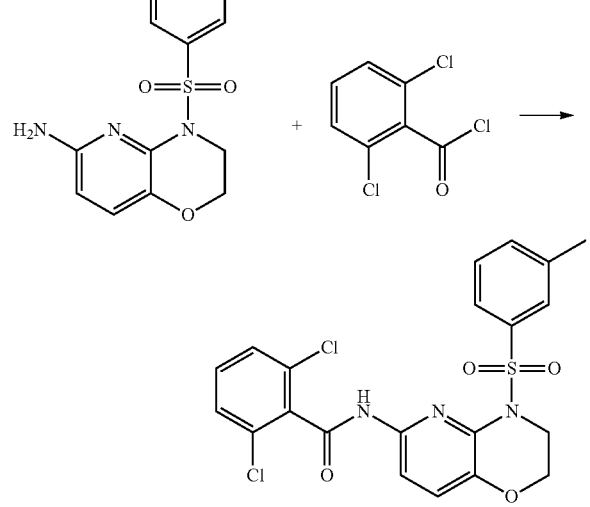

4-(Toluene-3-sulfonyl)-3,4-dihydro-2H-pyrido[3,2-b][1,4]oxazin-6-ylamine (20 mg, 0.065 mmol) was dissolved in p-dioxane (0.400 mL) and water (0.100 mL), followed by 2,6-dichlorobenzoyl chloride (21 µL, 0.098 mmol) and NaHCO₃ (11 mg, 0.13 mmol). The resulting mixture was stirred at room temperature for 15 hours, concentrated under vacuum, and purified by HPLC to give 2,6-dichloro-N-[4-(toluene-3-sulfonyl)-3,4-dihydro-2H-pyrido[3,2-b][1,4]oxazin-6-yl]-benzamide. LCMS (ESI): calc. $C_{21}H_{17}Cl_2N_3O_4S$=477; obs. M+H=478.

Example 3

Synthesis of 2-Phenyl-N-[4-(toluene-3-sulfonyl)-3,4-dihydro-2H-pyrido[3,2-b][1,4]oxazin-6-yl]-propionamide (3)

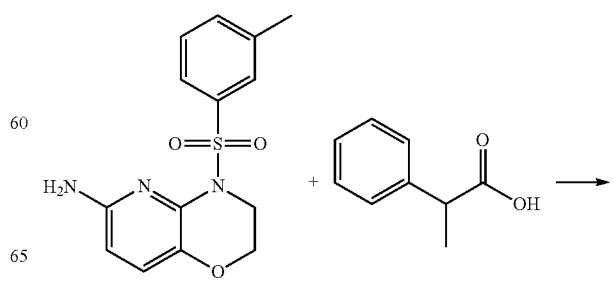

-continued

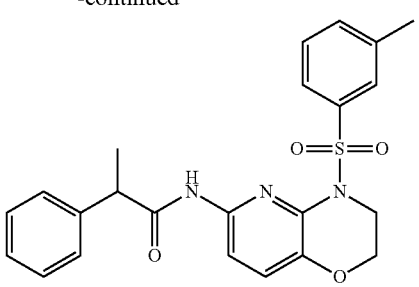

4-(Toluene-3-sulfonyl)-3,4-dihydro-2H-pyrido[3,2-b][1,4]oxazin-6-ylamine (20 mg, 0.065 mmol) was dissolved in N-methylpyrrolidinone (0.5 mL), followed by (d,l)-2-phenylpropionic acid (30 μL, 0.11 mmol), HATU (45 mg, 0.12 mmol), and diisopropyl ethylamine (23 μL, 0.13 mmol). The reaction mixture was stirred at room temperature for 18 hours. Then, the reaction mixture was then purified by HPLC to give 2-phenyl-N-[4-(toluene-3-sulfonyl)-3,4-dihydro-2H-pyrido[3,2-b][1,4]oxazin-6-yl]-propionamide. LCMS (ESI): calc. $C_{23}H_{23}N_3O_4S=437$; obs. M+H=438.

Example 4

Synthesis of 6-(Benzyloxy)-4-m-tolylsulfonyl)-3,4-dihydro-2H-pyrido[3,2-b][1,4]oxazine (4)

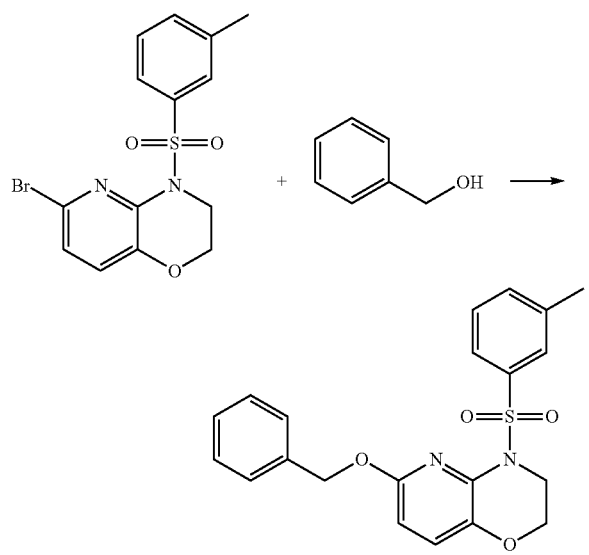

To 6-bromo-4-(toluene-3-sulfonyl)-3,4-dihydro-2H-pyrido[3,2-b][1,4]oxazine (50 mg, 140 mmol) in benzyl alcohol (400 μL) was added CuI (15 mg, 79 mmol), 1,10-phenanthroline (15 mg, 83 mmol), and $Cs_2CO_3$ (70 mg, 210 mmol). The resulting mixture was heated to 130° C. for 2 hours. Next, the reaction mixture was cooled to room temperature and quenched with a small amount of water, then extracted with ethyl acetate. The aqueous phase was discarded and the organic phase concentrated under reduced pressure. The resulting residue was purified by HPLC to afford 6-benzyloxy-4-(toluene-3-sulfonyl)-3,4-dihydro-2H-pyrido[3,2-b][1,4]oxazine. LCMS (ESI): calc. $C_{21}H_{20}N_2O_4S=396$; obs. M+H=397.

Example 5

Synthesis of 6-(2,6-Dichlorobenzyloxy)-4-m-tolylsulfonyl)-3,4-dihydro-2H-pyrido[3,2-b][1,4]oxazine (5)

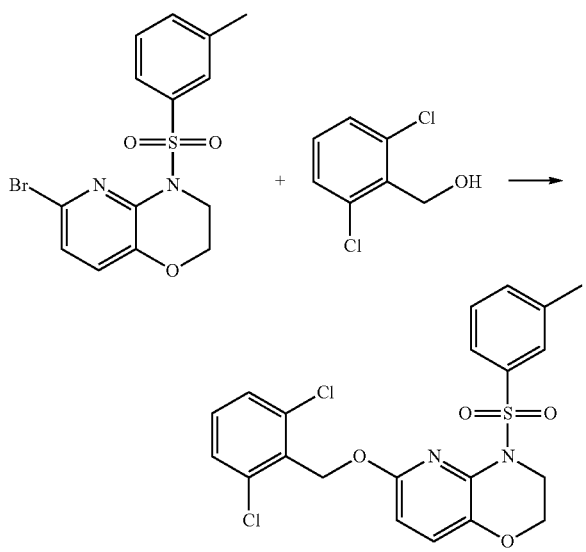

To 6-bromo-4-(toluene-3-sulfonyl)-3,4-dihydro-2H-pyrido[3,2-b][1,4]oxazine (50 mg, 140 mmol) in 2,6-dichlorobenzyl alcohol (400 μL) was added CuI (15 mg, 79 mmol), 1,10-phenanthroline (15 mg, 83 mmol), and $Cs_2CO_3$ (70 mg, 210 mmol). The resulting mixture was heated to 130° C. for 2 hours. Next, the reaction mixture was cooled to room temperature and quenched with a small amount of water, then extracted with ethyl acetate. The aqueous phase was discarded and the organic phase was concentrated under reduced pressure. The resulting residue was purified by HPLC to give 6-(2,6-dichloro-benzyloxy)-4-(toluene-3-sulfonyl)-3,4-dihydro-2H-pyrido[3,2b][1,4]oxazine. LCMS (ESI): calc. $C_{21}H_{18}Cl_2N_2O_4S=464$; obs. M+H=465.

Example 6

Synthesis of 6-(1-Phenylethoxy)-4-m-tolylsulfonyl)-3,4-dihydro-2H-pyrido[3,2-b][1,4]oxazine (6)

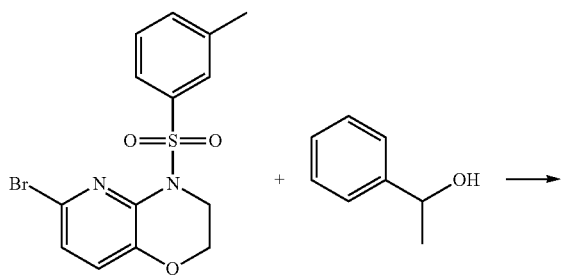

-continued

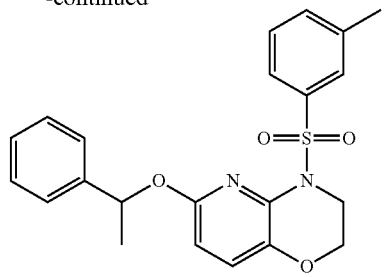

To 6-bromo-4-(toluene-3-sulfonyl)-3,4-dihydro-2H-pyrido[3,2-b][1,4]oxazine (50 mg, 140 mmol) in (d,l)-1-phenylethanol (400 μL) was added CuI (15 mg, 79 mmol), 1,10-phenanthroline (15 mg, 83 mmol), and $Cs_2CO_3$ (70 mg, 210 mmol). The resulting mixture was heated to 130° C. for 2 hours. Next, the reaction mixture was cooled to room temperature and quenched with a small amount of water, then extracted with ethyl acetate. The aqueous phase was discarded and the organic phase was concentrated under reduced pressure. The resulting residue was purified by HPLC to give 6-(1-phenyl-ethoxy)-4-(toluene-3-sulfonyl)-3,4-dihydro-2H-pyrido[3,2-b][1,4]oxazine. LCMS(ESI): calc. $C_{22}H_{22}N_2O_4S=410$; obs. M+H=411.

Example 7

Biological Assays for RORγ Activity

Exemplary compounds from the above Examples were tested for ability to increase RORγ activity using a RORγ-Ligand Binding Domain (LBD) TR-FRET Assay. Assay procedures and results are described below.

Part I—Procedures for RORγ-Ligand Binding Domain TR-FRET Assay

Recombinant, HIS-tagged RORγ-LBD was expressed in SF9 cells using a baculovirus expression system. Cells were lysed and the lysate was used as a source for RORγ-LBD for the assay. A 1:80 dilution of RORγ-LBD lysate in assay buffer (25 mM HEPES pH 7.0, 100 mM NaCl, 0.01% Tween, 0.1% BSA) was prepared and 5 μL was added to each well (RORγ-LBD final concentration ~3 nM). Control wells received lysate from SF9 cells not expressing RORγ-LBD.

Compounds to be tested were diluted to 100× final test concentration in DMSO and further diluted to 4× final test concentration using assay buffer to provide the test compound mixture. An aliquot (5 μL) of the test compound mixture was added to each well.

A 4× stock of biotinylated-LXXLL peptide from SRC1-2 (Biotin-CPSSHSSLTERHKILHRLLQEGSPS) was prepared in assay buffer and a 5 μL aliquot added to each well (450 nM final concentration). A 4× solution of europium tagged anti-HIS antibody (2 nM final concentration) and APC conjugated streptavidin (60 nM final concentration) were prepared and a 5 μL aliquot added to each well.

The final assay mixture was incubated for 4 hours to overnight, and the fluorescence signal was measured on an Envision plate reader: (Excitation filter=340 nm; APC emission=665 nm; Europium emission=615 nm; dichroic mirror=D400/D630; delay time=100 μs, integration time=200 μs).

$EC_{50}$ values for test compounds were calculated from the quotient of the fluorescence signal at 665 nm divided by the fluorescence signal at 615 nm using GraphPad Prism software.

Part III—Results

Compounds 1-6 from the above Examples were tested. Compounds 1-5 were determined to have an $EC_{50}$ less than or equal 15 μM. No promotion of RORγ activity was detected for compound 6 during the assay measuring $EC_{50}$ values less than or equal to 20 μM.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:

1. A compound represented by Formula I:

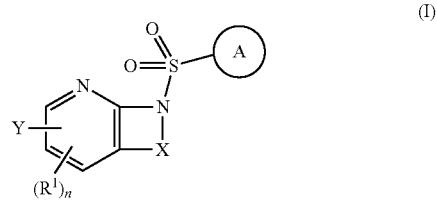

(I)

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkyl, $C_{1-6}$haloalkyl, $C_{1-6}$hydroxyalkyl, $C_{1-6}$alkoxy, $C_{1-6}$haloalkoxy, —N($R^4$)($R^5$), —$CO_2R^6$, —C(O)$R^6$, —CN, —$C_{1-4}$alkylene-$C_{1-4}$alkoxy, —$C_{1-4}$alkylene-N($R^4$)($R^5$), —$C_{1-4}$alkylene-$CO_2R^6$, —O—$C_{1-6}$alkylene-N($R^4$)($R^5$), —N($R^4$)C(O)—$C_{1-6}$alkylene-N($R^4$)($R^5$), —S(O)$_p$$C_{1-6}$alkyl, —$SO_2$N($R^4$)($R^5$), —N($R^4$)$SO_2$($C_{1-6}$alkyl), —C(O)N($R^4$)($R^5$), and —N($R^4$)C(O)N($R^4$)($R^5$);

X is —O—[C($R^6$)($R^7$)]-[C($R^6$)$_2$]-ψ or —O—C($R^6$)$_2$—C($R^6$)($R^7$)—ψ; wherein ψ is a bond to the sulfonamide ring nitrogen atom in Formula I;

Y is —N($R^2$)($R^3$) or —O-aralkyl, wherein said aralkyl is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N($R^4$)($R^5$), —CN, —$CO_2$—$C_{1-6}$alkyl, —C(O)—$C_{1-6}$alkyl, —C(O)N($R^4$)($R^5$), —S(O)$_p$$C_{1-6}$alkyl, —$SO_2$N($R^4$)($R^5$), and —N($R^4$)$SO_2$($C_{1-6}$alkyl);

$R^1$ represents independently for each occurrence hydrogen, halogen, or $C_{1-6}$alkyl;

$R^2$ is —C(O)-aryl, —C(O)-aralkyl, —C(O)—[C($R^6$)$_2$]$_m$-cycloalkyl, —C(O)—[C($R^6$)$_2$]$_m$-heterocyclyl, —C(O)—C$_{1-8}$alkyl, —C(O)—C$_{1-6}$alkylene-C$_{1-6}$alkoxyl, —C(O)—C$_{1-6}$alkylene-cycloalkyl, or —C(O)—C$_{1-6}$alkylene-heterocycloalkyl; each of which is optionally substituted with 1, 2, or 3 substituents independently selected from the group consisting of halogen, hydroxyl, C$_{1-6}$alkoxy, C$_{1-6}$haloalkoxy, C$_{1-6}$alkyl, C$_{1-6}$haloalkyl, —N($R^4$)($R^5$), —CN, —CO$_2$—C$_{1-6}$alkyl, —C(O)—C$_{1-6}$alkyl, —C(O)N($R^4$)($R^5$), —S(O)$_p$C$_{1-6}$alkyl, —SO$_2$N($R^4$)($R^5$), and —N($R^4$)SO$_2$(C$_{1-6}$alkyl);

$R^3$ is hydrogen or C$_{1-6}$alkyl;

$R^4$ and $R^5$ each represent independently for each occurrence hydrogen or C$_{1-6}$alkyl; or $R^4$ and $R^5$ taken together with the nitrogen atom to which they are attached form a 3-7 membered heterocyclic ring;

$R^6$ represents independently for each occurrence hydrogen or C$_{1-6}$alkyl;

$R^7$ is hydrogen, hydroxyl, C$_{1-6}$hydroxyalkyl, C$_{1-6}$alkyl, C$_{1-6}$haloalkyl, —CO$_2$$R^6$, C$_{1-6}$alkylene-CO$_2$$R^6$, C$_{1-4}$hydroxyalkylene-CO$_2$$R^6$, —N($R^4$)($R^5$), C$_{1-6}$alkylene-N($R^4$)($R^5$), C$_{1-6}$hydroxyalkylene-N($R^4$)($R^5$), —N($R^4$)C(O)$R^9$, C$_{1-6}$alkylene-N($R^4$)C(O)$R^9$, C$_{1-6}$alkylene-C(O)N($R^4$)($R^5$), —N($R^4$)CO$_2$—C$_{1-6}$alkyl, or C$_{1-6}$alkylene-N($R^4$)(C(O)N($R^4$)($R^5$); or $R^7$ is heterocycloalkyl or C$_{1-4}$alkylene-heterocycloalkyl, wherein the heterocycloalkyl is optionally substituted with 1, 2, or 3 substituents independently selected from the group consisting of oxo, halogen, hydroxyl, C$_{1-6}$alkyl, C$_{1-6}$haloalkyl, C$_{1-6}$hydroxyalkyl, C$_{1-6}$alkoxy, and C$_{1-6}$haloalkoxy;

$R^8$ is hydrogen, C$_{1-6}$alkyl, or —C(O)—C$_{1-6}$alkyl;

$R^9$ is hydrogen, C$_{1-6}$alkyl, C$_{1-6}$hydroxyalkyl, C$_{1-6}$alkylene-N($R^4$)($R^5$), or C$_{1-6}$alkylene-N($R^4$)C(O)—C$_{1-6}$alkyl;

n is 1 or 2; and m and p each represent independently for each occurrence 0, 1, or 2.

2. The compound of claim 1, wherein A is phenyl optionally substituted with 1, 2, or 3 substituents independently selected from the group consisting of halogen, C$_{1-6}$alkyl, C$_{1-6}$haloalkyl, C$_{1-6}$alkoxy, and C$_{1-6}$haloalkoxy.

3. The compound of claim 1, wherein A is heteroaryl optionally substituted with 1, 2, or 3 substituents independently selected from the group consisting of halogen, C$_{1-6}$alkyl, C$_{1-6}$haloalkyl, C$_{1-6}$alkoxy, and C$_{1-6}$haloalkoxy.

4. The compound of claim 1, wherein X is —O—[C($R^6$)($R^7$)]—[C($R^6$)$_2$]—ψ.

5. The compound of claim 1, wherein Y is —N($R^2$)($R^3$).

6. The compound of claim 5, wherein $R^2$ is —C(O)-aryl or —C(O)-aralkyl; each of which is optionally substituted with 1, 2, or 3 substituents independently selected from the group consisting of halogen, hydroxyl, C$_{1-6}$alkoxy, C$_{1-6}$haloalkoxy, C$_{1-6}$alkyl, and C$_{1-6}$haloalkyl.

7. The compound of claim 5, wherein $R^2$ is —C(O)-phenyl or —C(O)-benzyl; each of which is optionally substituted with 1, 2, or 3 substituents independently selected from the group consisting of halogen, C$_{1-6}$alkyl, and C$_{1-6}$haloalkyl.

8. The compound of claim 1, wherein Y is —O-aralkyl optionally substituted with 1, 2, or 3 substituents independently selected from the group consisting of halogen, hydroxyl, C$_{1-6}$alkoxy, C$_{1-6}$haloalkoxy, C$_{1-6}$alkyl, C$_{1-6}$haloalkyl, —N($R^4$)($R^5$), —CN, —CO$_2$—C$_{1-6}$alkyl, and —C(O)—C$_{1-6}$alkyl.

9. The compound of claim 1, wherein Y is —O-benzyl optionally substituted with 1, 2, or 3 substituents independently selected from the group consisting of halogen, C$_{1-6}$alkyl, and C$_{1-6}$haloalkyl.

10. The compound of claim 6, wherein $R^7$ is hydrogen.

11. The compound of claim 6, wherein $R^7$ is C$_{1-3}$hydroxyalkyl, methyl, ethyl, or C$_{1-3}$alkylene-N(H)C(O)—C$_{1-4}$alkyl.

12. The compound of claim 1, wherein the compound is represented by Formula II:

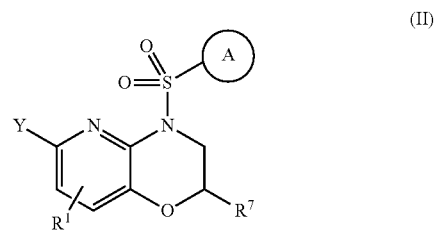

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, C$_{1-6}$alkyl, C$_{1-6}$haloalkyl, C$_{1-6}$hydroxyalkyl, C$_{1-6}$alkoxy, C$_{1-6}$haloalkoxy, —N($R^4$)($R^5$), —CO$_2$$R^6$, —C(O)$R^6$, —CN, —C$_{1-4}$alkylene-C$_{1-4}$alkoxy, and —C$_{1-4}$alkylene-N($R^4$)($R^5$);

Y is —N($R^2$)($R^3$) or —O-aralkyl, wherein said aralkyl is optionally substituted with 1, 2, or 3 substituents independently selected from the group consisting of halogen, hydroxyl, C$_{1-6}$alkoxy, C$_{1-6}$haloalkoxy, C$_{1-6}$alkyl, C$_{1-6}$haloalkyl, —N($R^4$)($R^5$), —CN, —CO$_2$—C$_{1-6}$alkyl, —C(O)—C$_{1-6}$alkyl, —C(O)N($R^4$)($R^5$), —S(O)$_p$C$_{1-6}$alkyl, —SO$_2$N($R^4$)($R^5$), and —N($R^4$)SO$_2$(C$_{1-6}$alkyl);

$R^1$ is hydrogen, halogen, or C$_{1-6}$alkyl;

$R^2$ is —C(O)-aryl, —C(O)-aralkyl, —C(O)—[C($R^6$)$_2$]$_m$-cycloalkyl, —C(O)-[C($R^6$)$_2$]$_m$-heterocyclyl, —C(O)—C$_{1-8}$alkyl, —C(O)—C$_{1-6}$alkylene-C$_{1-6}$alkoxyl, —C(O)—C$_{1-6}$alkylene-cycloalkyl, or —C(O)—C$_{1-6}$alkylene-heterocycloalkyl; each of which is optionally substituted with 1, 2, or 3 substituents independently selected from the group consisting of halogen, hydroxyl, C$_{1-6}$alkoxy, C$_{1-6}$haloalkoxy, C$_{1-6}$alkyl, C$_{1-6}$haloalkyl, —N($R^4$)($R^5$), —CN, —CO$_2$—C$_{1-6}$alkyl, —C(O)—C$_{1-6}$alkyl, —C(O)N($R^4$)($R^5$), —S(O)$_p$C$_{1-6}$alkyl, —SO$_2$N($R^4$)($R^5$), and —N($R^4$)SO$_2$(C$_{1-6}$alkyl);

$R^3$ is hydrogen or C$_{1-6}$alkyl;

$R^4$ and $R^5$ each represent independently for each occurrence hydrogen or C$_{1-6}$alkyl;

or $R^4$ and $R^5$ taken together with the nitrogen atom to which they are attached form a 3-7 membered heterocyclic ring;

$R^6$ represents independently for each occurrence hydrogen or C$_{1-6}$alkyl;

$R^7$ is hydrogen, hydroxyl, C$_{1-6}$hydroxyalkyl, C$_{1-6}$alkyl, C$_{1-6}$haloalkyl, —CO$_2$$R^6$, C$_{1-6}$alkylene-CO$_2$$R^6$, C$_{1-4}$hydroxyalkylene-CO$_2$$R^6$, —N($R^4$)($R^5$), C$_{1-6}$alkylene-N($R^4$)($R^5$), C$_{1-6}$hydroxyalkylene-N($R^4$)($R^5$), —N($R^4$)C(O)$R^9$, C$_{1-6}$alkylene-N($R^4$)C(O)$R^9$, C$_{1-6}$alkylene-C(O)

N(R⁴)(R⁵), —N(R⁴)CO₂—C₁₋₆alkyl, or C₁₋₆alkylene-N(R⁴)(C(O)N(R⁴)(R⁵); or R⁷ is heterocycloalkyl or C₁₋₄alkylene-heterocycloalkyl, wherein the heterocycloalkyl is optionally substituted with 1, 2, or 3 substituents independently selected from the group consisting of oxo, halogen, hydroxyl, C₁₋₆alkyl, C₁₋₆haloalkyl, C₁₋₆hydroxyalkyl, C₁₋₆alkoxy, and C₁₋₆haloalkoxy;

R⁹ is hydrogen, C₁₋₆alkyl, C₁₋₆hydroxyalkyl, C₁₋₆alkylene-N(R⁴)(R⁵), or C₁₋₆alkylene-N(R⁴)C(O)—C₁₋₆alkyl; and m and p each represent independently for each occurrence 0, 1, or 2.

13. The compound of claim 12, wherein A is aryl optionally substituted with 1, 2, or 3 substituents independently selected from the group consisting of halogen, C₁₋₆alkyl, C₁₋₆haloalkyl, C₁₋₆alkoxy, and C₁₋₆haloalkoxy.

14. The compound of claim 12, wherein A is phenyl optionally substituted with 1, 2, or 3 substituents independently selected from the group consisting of halogen, C₁₋₆alkyl, C₁₋₆haloalkyl, C₁₋₆alkoxy, and C₁₋₆haloalkoxy.

15. The compound of claim 12, wherein Y is —N(R²)(R³).

16. The compound of claim 15, wherein R² is —C(O)-aryl or —C(O)-aralkyl; each of which is optionally substituted with 1, 2, or 3 substituents independently selected from the group consisting of halogen, hydroxyl, C₁₋₆alkoxy, C₁₋₆haloalkoxy, C₁₋₆alkyl, and C₁₋₆haloalkyl.

17. The compound of claim 15, wherein R² is —C(O)-phenyl or —C(O)-benzyl; each of which is optionally substituted with 1, 2, or 3 substituents independently selected from the group consisting of halogen, C₁₋₆alkyl, and C₁₋₆haloalkyl.

18. The compound claim 15, wherein R² is represented by:

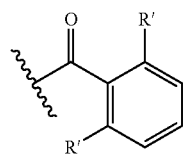

wherein each R' is independently halogen, C₁₋₆alkyl, or C₁₋₆haloalkyl.

19. The compound of claim 15, wherein R² is represented by:

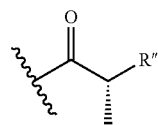

wherein R'' is C₁₋₆alkyl, aryl, or heterocyclyl, each of which is optionally substituted with 1, 2, or 3 substituents independently selected from the group consisting of halogen, hydroxyl, C₁₋₆alkoxy, C₁₋₆haloalkoxy, C₁₋₆alkyl, C₁₋₆haloalkyl, —N(R⁴)(R⁵), —CN, —CO₂—C₁₋₆alkyl, —C(O)—C₁₋₆alkyl, —C(O)N(R⁴)(R⁵), —S(O)ₚC₁₋₆alkyl, —SO₂N(R⁴)(R⁵), and —N(R4)SO₂(C₁₋₆alkyl).

20. The compound of claim 12, wherein Y is —O-aralkyl optionally substituted with 1, 2, or 3 substituents independently selected from the group consisting of halogen, hydroxyl, C₁₋₆alkoxy, C₁₋₆haloalkoxy, C₁₋₆alkyl, C₁₋₆haloalkyl, —N(R⁴)(R⁵), —CN, —CO₂—C₁₋₆alkyl, and —C(O)—C₁₋₆alkyl.

21. The compound of claim 12, wherein Y is —O-benzyl optionally substituted with 1, 2, or 3 substituents independently selected from the group consisting of halogen, C₁₋₆alkyl, and C₁₋₆haloalkyl.

22. The compound of claim 16, wherein R⁷ is hydrogen.

23. The compound of claim 16, wherein R⁷ is C₁₋₆hydroxyalkyl, C₁₋₆alkyl, C₁₋₆alkylene-CO₂R⁶, C₁₋₆alkylene-N(R⁴)(R⁵), or C₁₋₆alkylene-N(R⁴)C(O)R⁹.

24. A compound in Table 2A or 3A below, or a pharmaceutically acceptable salt thereof:

TABLE 2A

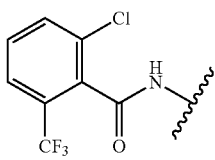

| No. | Y | | Z |
|---|---|---|---|
| II-11 | 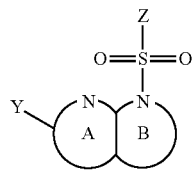 | 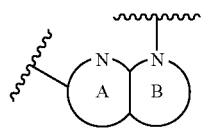 | 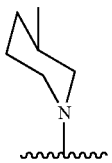 [SMILES: *N1CCCC(C)C1] |

TABLE 2A-continued
| No. | Y | | Z |
|---|---|---|---|
| II-12 | 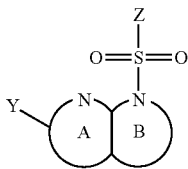 | 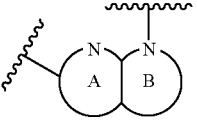 | 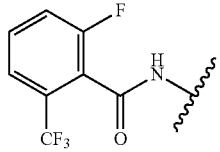 |
| II-13 | 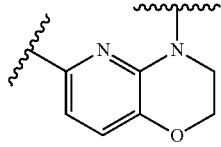 [SMILES: *c1ccc2c(n1)N(*)CCO2] | 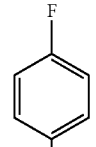 | 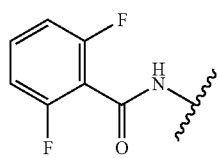 |
| II-14 | 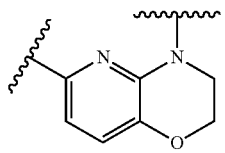 [SMILES: *c1ccc2c(n1)N(*)CCO2] | 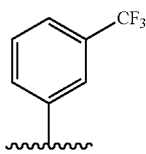 [SMILES: *c1cccc(C(F)(F)F)c1] | 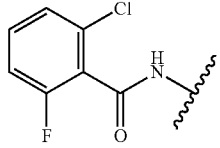 |
| II-15 | 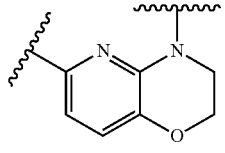 [SMILES: *c1ccc2c(n1)N(*)CCO2] | 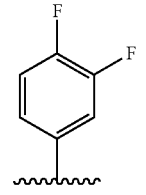 [SMILES: *c1ccc(F)c(F)c1] | 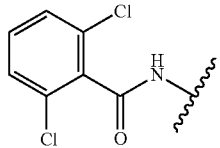 |
| II-16 | 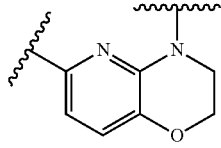 [SMILES: *c1ccc2c(n1)N(*)CCO2] | 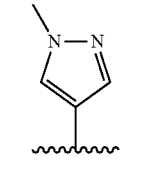 | 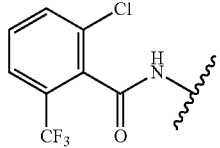 [SMILES: *NC(=O)c1c(Cl)cccc1C(F)(F)F] |
| II-17 | 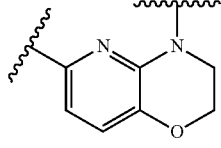 [SMILES: *c1ccc2c(n1)N(*)CCO2] | 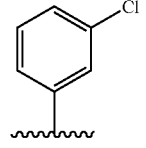 [SMILES: *c1cccc(Cl)c1] | 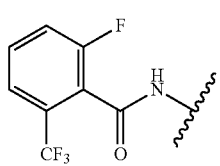 [SMILES: *NC(=O)c1c(F)cccc1C(F)(F)F] |
| II-18 | 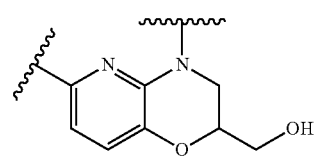 [SMILES: *c1ccc2c(n1)N(*)CC(CO)O2] | 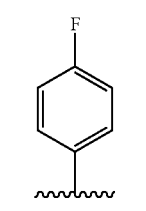 | 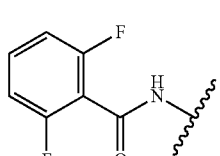 |

TABLE 2A-continued

| No. | Y | | Z |
|---|---|---|---|
| II-19 | 2-Cl, 6-F benzamide | pyrido-oxazine with CH2OH | 3,4-difluorophenyl |
| II-20 | 2,6-dichlorobenzamide | pyrido-oxazine with CH2N(H)C(O)CH3 | 1-methyl-1H-pyrazol-4-yl |
| II-21 | 2-Cl, 6-CF3 benzamide | pyrido-oxazine with CH2N(H)C(O)CH3 | piperidin-1-yl |
| II-22 | 2-F, 6-CF3 benzamide | pyrido-oxazine with CH2N(H)C(O)CH3 | 4-fluorophenyl |
| II-23 | 2,6-difluorobenzamide | pyrido-oxazine with CH3 | 3-(trifluoromethyl)phenyl |
| II-24 | 2-Cl, 6-F benzamide | pyrido-oxazine with CH3 | 3,4-difluorophenyl |
| II-25 | 2,6-dichlorobenzamide | pyrido-oxazine with CH3 | 1-methyl-1H-pyrazol-4-yl |

TABLE 3A

| No. | Compound |
|---|---|
| III-1 | |
| III-2 | |
| III-3 | |
| III-4 | |
| III-5 | |

TABLE 3A-continued

| No. | Compound |
|---|---|
| III-6 | |
| III-7 | |
| III-8 | |
| III-9 | |
| III-10 | |

TABLE 3A-continued

| No. | Compound |
|---|---|
| III-11 | |
| III-12 | |
| III-13 | |
| III-14 | |
| III-15 | |
| III-16 | |
| III-17 | |
| III-18 | |
| III-19 | |
| III-20 | |

TABLE 3A-continued
| No. | Compound |
|---|---|
| III-21 | 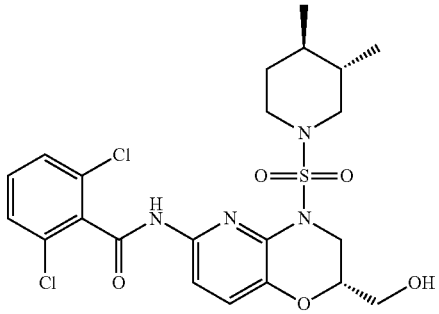 [SMILES: C[C@@H]1CCN(S(=O)(=O)N2C[C@H](CO)Oc3ccc(NC(=O)c4c(Cl)cccc4Cl)nc32)C[C@H]1C] |
| III-22 | 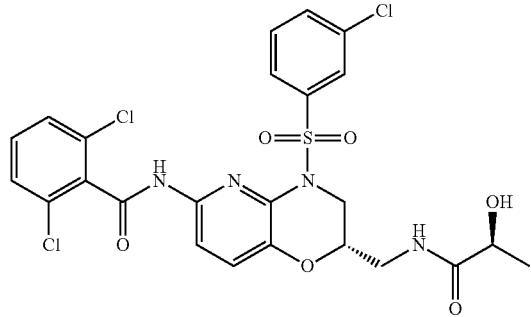 [SMILES: C[C@H](O)C(=O)NC[C@H]1CN(S(=O)(=O)c2cccc(Cl)c2)c2nc(NC(=O)c3c(Cl)cccc3Cl)ccc2O1] |
| III-23 | 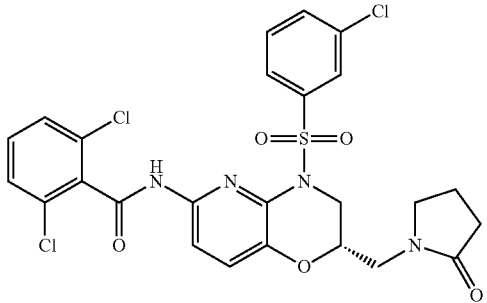 [SMILES: O=C(Nc1ccc2c(n1)N(S(=O)(=O)c1cccc(Cl)c1)C[C@H](CN1CCCC1=O)O2)c1c(Cl)cccc1Cl] |
| III-24 | 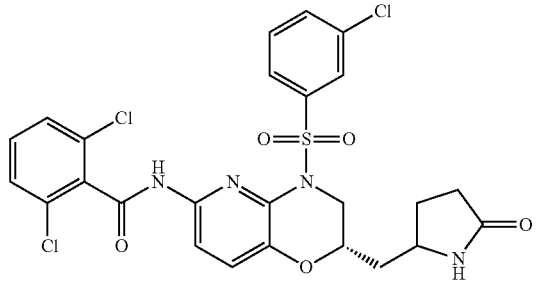 [SMILES: O=C1CCC(C[C@H]2CN(S(=O)(=O)c3cccc(Cl)c3)c3nc(NC(=O)c4c(Cl)cccc4Cl)ccc3O2)N1] |
| III-25 | 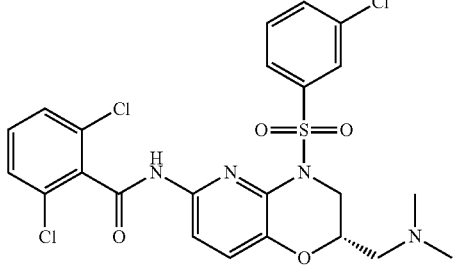 |
| III-26 | 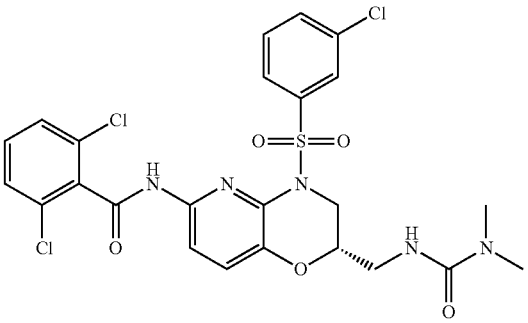 [SMILES: CN(C)C(=O)NC[C@H]1CN(S(=O)(=O)c2cccc(Cl)c2)c2nc(NC(=O)c3c(Cl)cccc3Cl)ccc2O1] |
| III-29 | 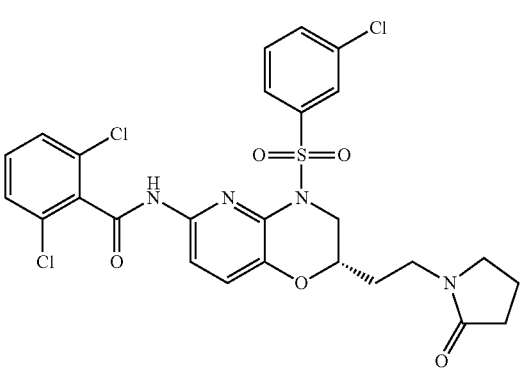 [SMILES: O=C(Nc1ccc2c(n1)N(S(=O)(=O)c1cccc(Cl)c1)C[C@H](CCN1CCCC1=O)O2)c1c(Cl)cccc1Cl] |
| III-30 | 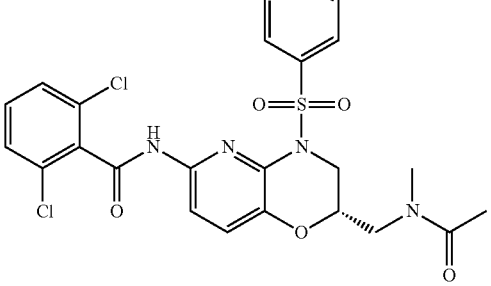 |
| III-31 | 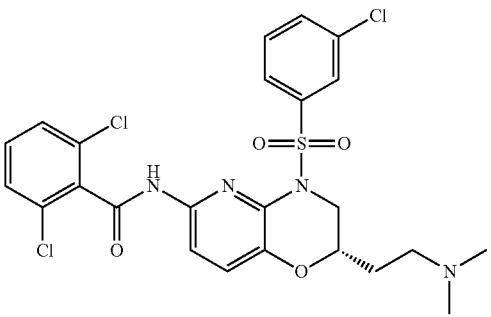 [SMILES: CN(C)CC[C@H]1CN(S(=O)(=O)c2cccc(Cl)c2)c2nc(NC(=O)c3c(Cl)cccc3Cl)ccc2O1] |

TABLE 3A-continued

| No. | Compound |
|---|---|
| III-32 | (2,6-dichlorobenzamide)-N-pyrido-oxazine with 3-chlorobenzenesulfonyl, methyl, CH2OH |
| III-48 | (2,6-dichlorobenzyloxy)-pyrido-oxazine with 3-chlorobenzenesulfonyl, CH2OH |
| III-49 | (2,6-dichlorobenzyloxy)-pyrido-oxazine with 3,5-dimethylpiperidinyl sulfonyl, CH2OH |
| III-51 | (2,6-dichlorobenzyloxy)-pyrido-oxazine with 3-chlorobenzenesulfonyl, CH2NHC(O)CH3 |
| III-52 | (2,6-dichlorobenzyloxy)-pyrido-oxazine with 3,5-dimethylpiperidinyl sulfonyl, CH2NHC(O)CH3 |

25. A pharmaceutical composition comprising a compound of claim 1 and a pharmaceutically acceptable carrier.

26. A method of treating a disorder selected from the group consisting of cancer, bacterial infection, and fungal infection, comprising administering a therapeutically effective amount of a compound of claim 1 to a subject in need thereof to treat the disorder, wherein the cancer is selected from the group consisting of colon cancer, pancreatic cancer, breast cancer, ovarian cancer, prostate cancer, squamous cell carcinoma, basal cell carcinoma, adenocarcinoma, sweat gland carcinoma, sebaceous gland carcinoma, lung cancer, leukemia, bladder cancer, stomach cancer, cervical cancer, testicular cancer, skin cancer, rectal cancer, thyroid cancer, kidney cancer, uterus cancer, espophagus cancer, liver cancer, an acoustic neuroma, oligodendroglioma, meningioma, neuroblastoma, and retinoblastoma.

27. The method of claim 26, wherein the disorder is colon cancer, pancreatic cancer, breast cancer, ovarian cancer, prostate cancer, squamous cell carcinoma, basal cell carcinoma, adenocarcinoma, sweat gland carcinoma, sebaceous gland carcinoma, lung cancer, leukemia, bladder cancer, stomach cancer, cervical cancer, testicular cancer, skin cancer, rectal cancer, thyroid cancer, kidney cancer, uterus cancer, espophagus cancer, liver cancer, an acoustic neuroma, oligodendroglioma, meningioma, neuroblastoma, or retinoblastoma.

28. A method of increasing the amount of IL-17 in a subject, comprising administering to a subject an effective amount of a compound of claim 1 to increase the amount of IL-17 in the subject.

29. The method of claim 26, wherein the subject is a human.

30. A method of promoting the activity of RORγ, comprising exposing a RORγ to an effective amount of a compound of claim 1 to promote the activity of said RORγ.

* * * * *